(12) United States Patent
Gray et al.

(10) Patent No.: US 12,197,448 B2
(45) Date of Patent: Jan. 14, 2025

(54) GAIT-BASED BIOMETRIC DATA ANALYSIS SYSTEM

(71) Applicant: AUTONOMOUS ID CANADA INC., Ottawa (CA)

(72) Inventors: Todd Gray, Ottawa (CA); Vladimir Polotski, Ottawa (CA); Barry Smale, Ottawa (CA); Bernard F. Grisoni, Cordova, TN (US); Erik Mettala, Finksburg, MD (US)

(73) Assignee: AUTONOMOUS ID CANADA INC., Ottawa (CA)

( * ) Notice: Subject to any disclaimer, the term of this patent is extended or adjusted under 35 U.S.C. 154(b) by 930 days.

(21) Appl. No.: 17/107,949

(22) Filed: Nov. 30, 2020

(65) Prior Publication Data

US 2021/0182298 A1  Jun. 17, 2021

Related U.S. Application Data

(60) Continuation-in-part of application No. 15/826,744, filed on Nov. 30, 2017, now Pat. No. 10,885,041, (Continued)

(51) Int. Cl.
*G06F 16/2457* (2019.01)
*A43B 3/34* (2022.01)
(Continued)

(52) U.S. Cl.
CPC .......... *G06F 16/24575* (2019.01); *A43B 3/34* (2022.01); *A61B 5/1038* (2013.01);
(Continued)

(58) Field of Classification Search
CPC ............. G06F 16/24575; G06F 16/248; A43B 3/34; A61B 5/1038; A61B 5/112
See application file for complete search history.

(56) References Cited

U.S. PATENT DOCUMENTS 4,812,976 A   3/1989  Lundy
6,183,425 B1  2/2001  Whalen
(Continued)

FOREIGN PATENT DOCUMENTS

WO   2004021883   3/2004
WO   2004092915   10/2004
WO   2010096907   9/2010

OTHER PUBLICATIONS

Kong, Kyoungchul et al., "A Gait Monitoring System Based on Air Pressure Sensors Embedded in a Shoe", IEEE/ASME Transactions on Mechatronics, vol. 14, No. 3, Jun. 2009. 13 Pages.
(Continued)

*Primary Examiner* — Daniel L Cerioni
(74) *Attorney, Agent, or Firm* — Brion Raffoul

(57) ABSTRACT

Systems and methods for determining a user's health/wellness condition. Gait-based biometric data from a user is gathered using a sensor module. The biometric data is transmitted to a data processing module that compares characteristics of the biometric data with previously obtained baseline biometric data from the same user. Differences between the current data and the baseline data indicate changes in the user's condition. Databases containing kinematic chain models for the user are used to obtain more accurate and more specific indications regarding determined changes in the user's condition. A base kinematic chain model is created for the user when the user first uses the system and current kinematic chain models are generated for each biometric data set gathered. Characteristics of the base and the current kinematic chain models are compared to determine changes in the user's condition.

15 Claims, 9 Drawing Sheets

Related U.S. Application Data which is a division of application No. 14/946,358, filed on Nov. 19, 2015, now Pat. No. 9,864,780, which is a continuation-in-part of application No. 13/939,923, filed on Jul. 11, 2013, now Pat. No. 9,204,797, which is a continuation-in-part of application No. 13/581,633, filed on Dec. 6, 2012, now Pat. No. 9,188,963.

(51) Int. Cl.
    *A61B 5/00*     (2006.01)
    *A61B 5/103*     (2006.01)
    *A61B 5/11*     (2006.01)
    *G06F 16/248*     (2019.01)

(52) U.S. Cl.
    CPC ............ *A61B 5/112* (2013.01); *A61B 5/6807* (2013.01); *G06F 16/248* (2019.01); *A61B 2562/046* (2013.01)

(56) References Cited

U.S. PATENT DOCUMENTS

| | | | |
|---|---|---|---|
| 6,360,597 | B1 | 3/2002 | Hubbard, Jr. |
| 10,716,517 | B1 * | 7/2020 | McNair ................ A61B 5/1123 |
| 2002/0107649 | A1 | 8/2002 | Takiguchi |
| 2004/0228503 | A1 | 11/2004 | Cutler |
| 2005/0288609 | A1 | 12/2005 | Warner |
| 2006/0080551 | A1 | 4/2006 | Mantyjarvi |
| 2006/0287883 | A1 | 12/2006 | Turgiss |
| 2007/0021689 | A1 | 1/2007 | Stergiou |
| 2008/0287832 | A1 | 11/2008 | Terrafranca, Jr. |
| 2009/0058855 | A1 | 3/2009 | Mishra |
| 2010/0324455 | A1 | 12/2010 | Rangel |
| 2011/0282828 | A1 | 11/2011 | Precup |
| 2012/0203573 | A1 * | 8/2012 | Mayer .................. G16H 40/63 705/3 |
| 2012/0086550 | A1 | 12/2012 | LeBlanc |
| 2016/0378950 | A1 * | 12/2016 | Reiner .................. G16H 70/40 705/2 |
| 2017/0098032 | A1 * | 4/2017 | Desai .................... G16B 50/00 |
| 2018/0089280 | A1 * | 3/2018 | Gray ................. G06F 16/24575 |
| 2020/0003643 | A1 * | 1/2020 | Muzaffar ............ A61B 5/6807 |
| 2020/0155035 | A1 * | 5/2020 | Mariani ................ G06V 40/25 |
| 2021/0023719 | A1 * | 1/2021 | Alt ........................ B25J 9/1697 |

OTHER PUBLICATIONS

Yamakawa, Takeshi et al., "Biometric Personal Identification Based on Gait Pattern Using Both Feet Pressure Change", Automation Congress, 2008. WAC 2008. World, pp. 1-6, Sep. 28, 2008-Oct. 2, 2008. 6 Pages.

Huang, Bufu et al., "Gait Modeling for Human Identification", 2007 IEEE International Conference on Robotics and Automation, Roma, Italy, Apr. 10-14, 2007. 6 Pages.

Chedevergne, Fany et al., "Development of a Mechatronical Device to Measure Plantar Pressure for Medical Prevention of Gait Issues", Proceedings of the 2006 IEEE International Conference on Mechatronics and Automation, Jun. 25-28, 2006, Luoyang, China. 5 Pages.

Boulgouris et al., "Multimodal Physiological Biometrics Authentication", Wiley-IEEE, Nov. 2009, Chapter 18. 22 Pages.

Morris, Stacy et al., "Shoe-Integrated Sensor System for Wireless Gait Analysis and Real-Time Feedback", Proceedings of the Second Joint EMBS/BMES Conference, Houston, TX, Oct. 23-26, 2002. 2 Pages.

Gafurov, Davrondzhon et al., "Biometric Gait Authentication Using Accelerometer Sensor", Journal of Computers, vol. 1, No. 7, Oct./Nov. 2006. 9 Pages.

International Searching Authority, International Search Report dated Nov. 3, 2010 on corresponding PCT International Application No. PCT/CA2010/001002. 4 Pages.

Office Action dated Nov. 25, 2015 issued on corresponding Canadian Patent Application No. 2,791,403. 3 Pages.

* cited by examiner

GAIT-BASED BIOMETRIC DATA ANALYSIS SYSTEM

RELATED APPLICATIONS

This application is a Continuation-in-Part of U.S. application Ser. No. 15/826,744 filed on Nov. 30, 2017, which is a Divisional of U.S. Pat. No. 9,864,780 filed Nov. 19, 2015, which is a Continuation-in-Part of U.S. Pat. No. 9,204,797 filed Jul. 11, 2013, which is a Continuation-in-Part of U.S. Pat. No. 9,188,963 filed Dec. 6, 2012.

TECHNICAL FIELD

The present invention relates to a gait based biometric data analysis system used for the detection and isolation of movement and mobility biomarkers and which can be used for the determination of the progression or regression of health, wellness, and fitness.

BACKGROUND

The increase in the use of remote patient monitoring, mobile healthcare, and user discrete analytical fields have highlighted some shortcomings of current personal and population-based analytics systems as well as the effects of generally prescribed pharmacological and therapeutic treatments after diagnosis.

Analytical systems generally come in a number of categories. Data, text, and imaging systems use large installed or network-based hardware and software platforms which, when used, diagnoses the user's condition using well-known techniques and methods. Less cumbersome and intrusive analytical systems and methods include question and answers done orally or written, which measure temperature, weight, pulse rate, as well as a plethora of other biological and physiological indicators, including through the experienced eye of a practitioner, clinician, therapist or surgeon specialist. These indicators are used when searching for signs of health, fitness level, and disease. The ancient medicinal art of reflexology is one historical effort focused on the correlation between disease pathology and the feet. Adverse reactions to prescribed pharmacological and therapeutic treatments of disease are known to adversely affect a person's stride, balance, weight, joints, tendons, and ligaments and, as a consequence, that person's gait as well.

The above noted analytical systems have their drawbacks. Specifically, current techniques may involve extremely large and use controlled or proprietary software algorithms. They are also fundamentally reliant on the quality and efficacy of the data input. Similarly, question and answers obtained orally or in written form are area specific, limited in scope and use, and require more active participation and knowledge from the user. In addition, current techniques are such that the experienced eye of the practitioner, clinician, therapist or surgeon only lasts as long as a patient's visit to the clinic/health facility. These and other current systems have been seen as too invasive, too cumbersome for some people to use, limited in scope, limited in reliability and utility of data, or simply too complicated to understand.

There is therefore a need for an analytical system that is neither invasive nor linear in scope and use and which provides access to quality and reliable data gathered by convenient user-worn devices.

SUMMARY

The present invention provides systems and methods for determining a user's health/wellness condition. Gait-based biometric data from a user is gathered using a sensor module. The biometric data is transmitted to a data processing module that compares characteristics of the biometric data with previously obtained baseline biometric data from the same user. Differences between the current data and the baseline data indicate changes in the user's condition. Databases containing kinematic chain models for the user are used to obtain more accurate and more specific indications regarding determined changes in the user's condition. A base kinematic chain model is created for the user when the user first uses the system and current kinematic chain models are generated for each biometric data set gathered. Characteristics of the base data and the current kinematic chain models are compared to determine changes in the user's condition.

In a first aspect, the present invention provides a system for determining a change in a user's condition, the system comprising:
  at least one sensor module comprising at least one sensor for gathering gait-based biometric data from said user, said sensor module being in a single device having at least two sensors;
  a data storage module for storing data relating to baseline data, said baseline data being derived from said gait-based biometric data gathered from said at least one sensor module when said user first uses said system;
  a data processing module for receiving data from said sensor module, said data processing module being for comparing characteristics of said baseline data with characteristics of said data received from said sensor module;
  at least one database in communication with said data processing module, said at least one database containing data relating to a base kinematic chain model specific to said user, said base kinematic chain model being derived from said baseline data;
  wherein
  said data processing module derives a current kinematic chain model from said data received from said at least one sensor module;
  said data processing module compares characteristics of said current kinematic chain model with characteristics of said base kinematic chain model;
  a change in said user's condition is indicated when said characteristics of said data received from said at least one sensor module are not within predetermined limits of said characteristics of said baseline data.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
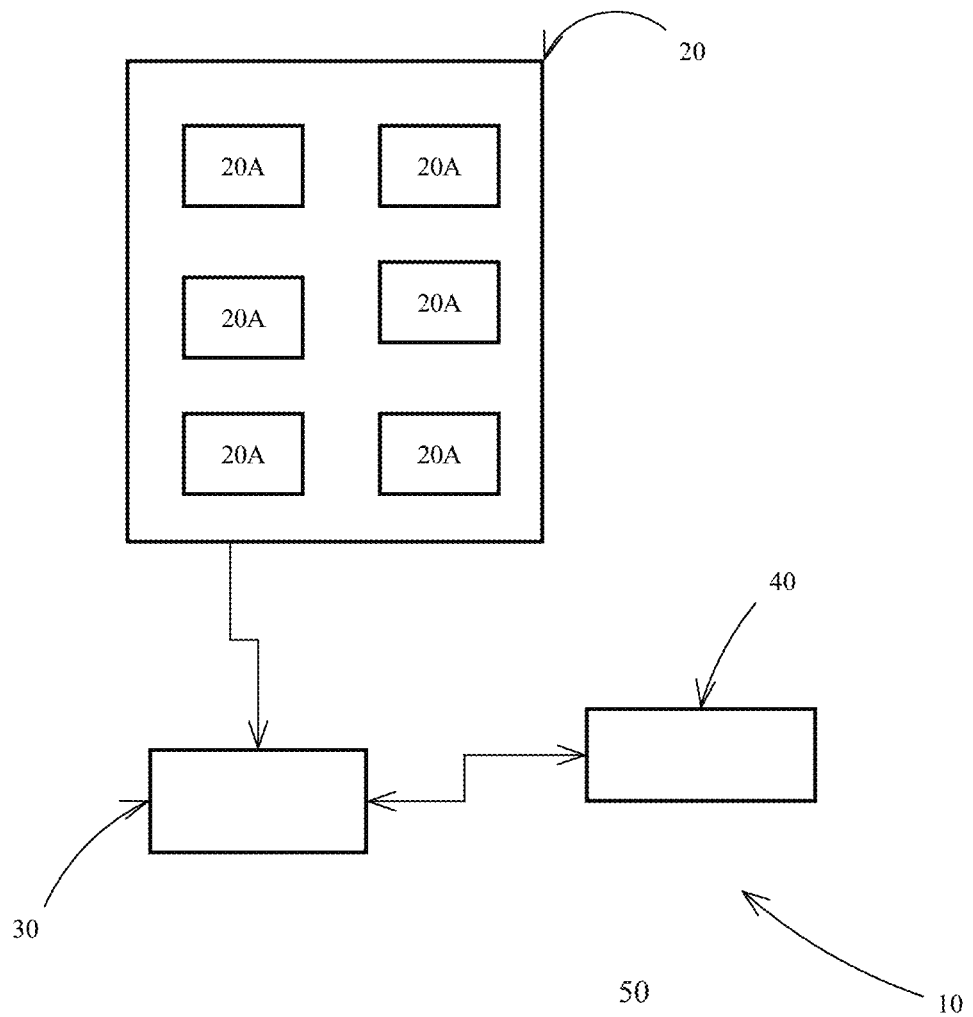
FIG. 1 is a block diagram of the system according to one aspect of the invention.

In one aspect, the present invention can be used for the detection of known pathological conditions associated with disease states and for the detection of the effects of prescribed pharmacological and therapeutic treatments.

In another aspect, the present invention provides analytical systems and methods for the assessment of movement, balance, weight and mobility based on user gait. As well, the present invention allows for intelligent pattern matching to assess kinematic chain models spanning all 26 bones and 31 joints in each foot and ankle, up through the lower leg, upper leg, pelvis, sacral vertebrae, and lumbar vertebrae. These kinematic chain models describe nominal gait, supination and pronation, and excessive supination and excessive pronation of the foot. In addition, research has demonstrated shared disease patterns useful for the detection of diabetes, Alzheimer's, and Parkinson's disease among other ailments, sicknesses, and injuries. Each of these patterns has a direct correlation to a range of sport injuries conditions such as concussion, head trauma, as well as neurological ailments and orthopedics. A sensor module with multiple sensors is placed inside a user's shoe and biometric data is gathered from the sensors when the user takes a step, walks, runs, jumps, dances, or shuffles. The data extracted from regions using groups of pressure sensors, groups of thermal sensors, and other sensor types is used to generate loops as the various sets of data are plotted against each other to form a loop-based biometric of a user. The loops generated from the data are then compared against stored loops previously obtained from known individuals having nominal function or specific identified diseases, injury or sickness and loop data recorded and annotated to indicate specific pathologies associated with the progression or regression of the disease, sickness or injury state, as well as other characteristic data extrapolated from the loops. Based on the results of the comparison, the user's movement, weight and other mobility characteristics are assessed using predetermined indicators in conjunction with analytical input from distributed databases and with the input of each user's specific characteristic data from which other data can be extrapolated.

It should be clear that, using the biometric data, it can be determined whether the user has increased activity and performance of basic movement functions, i.e., shuffling, walking, running, dancing, jumping, or whether the user has the proper fitting insole insert and, if not, recommendations can be made. As a result of this analysis, recommendations can be made to the user with the recommendations being focused on directing changes in their gait to thereby lead to a more optimal kinematic skeletal performance. Similarly, the data gathered can be used to determine whether the footwear the user is using is of a proper fit or whether recommendations for alternative footwear types and models is warranted. As well, the data and the system can be used to determine whether the user has a specific condition or ailment, whether a specific condition or ailment is worsening, or whether a specific condition or ailment is improving. These results can be presented for use by attending physicians as disease or injury detection indicators, or subsequently, as disease or injury progression indicators.

In one embodiment, the user's biometric data is, preferably, previously extracted from his gait. The previously gathered data, and the plotted loops derived therefrom, can be used as a baseline for the user. Subsequent biometric data sets gathered from the user can then be compared against the baseline. Depending on the comparison results, a range of analyses can be performed to determine changes in the user's condition. Such changes can include progression or regression of a user's movement and/or mobility. Data gathered from the general population can be used to establish any correlation between a person's changing gait as he or she progresses or regresses in a specific health and fitness condition. Treatment effects of prescribed pharmacological and/or therapeutic remedies can also be determined using the baseline biometric data from the user as the user progresses in his or her daily programs and treatment. Periodic gathering of the user's biometric data can be used to track and monitor the effects of the treatment on the user's gait to establish any causal link between the treatment regime and the user's gait and other gait-based characteristics such as weight and load bearing weight. Such links and the specific effects of the fitness program or treatment regime can then be used to further heighten the effectiveness of shoe-based biometric data gathering devices as diagnostic tools. In addition to the above, the diagnostic tools can be supplemented by a network of distributed databases that have pathomechanical movement and mobility data including kinematic models of the human skeleton spanning all 26 bones and 31 joints in each foot and ankle, up through the lower leg, upper leg, pelvis, sacral vertebrae, and lumbar vertebrae. Such data, in conjunction with data received from an insole and with a user's specific characteristics, can be used to narrow down a suitable diagnosis for the user's pathomechanical abnormality. Such network of distributed databases storing a population of movement and mobility data and related characteristic data such as foot shape, foot type, standing weight and posture can be used to narrow down gait-based movement and mobility biomarkers associated with a range of performance, human ailments, injury and disease.

To assist in the implementation of the present invention, kinematic models of the human skeleton have been formed as constructs. In the present invention, the kinematic models are defined using Denavit-Hartenberg conventions, and the dynamic models are defined using the Jacobian conventions.

For the models used in the present invention, geometry is applied to the analysis of the movement of multi-degree of freedom kinematic chains that form the structure of skeletal systems. The emphasis on geometry means that the links are modeled as rigid bodies and joints are assumed to provide pure rotation or translation.

The kinematics models used within the present invention can be stored within a network of distributed databases and these models map the relationship between the dimensions and connectivity of kinematic chains and the position, velocity and acceleration of each of the links in the skeletal system in order to assess and approximate movement and to interpret forces and torques. The relationship between mass and inertia properties, motion, and the associated forces and torques may be analyzed using the network of distributed databases as part of skeletal dynamics.

A further aspect of the systems according to the present invention encodes established pathomechanical kinematic models specific to disease pathologies, injury and sickness. These models are stored and used within a network of distributed databases and can be used in the comparison of characteristic loop data input from the gait-based biometric device and the kinematic data models stored within the network of distributed databases.

The present invention also provides systems and methods that relate to a mathematical formalism that accurately specifies the position of each joint, the velocity of each joint, and the acceleration of each joint. When a joint is prismatic, then the velocity is a linear velocity and the acceleration is a linear acceleration. When a joint is rotational, then the velocity is a rotational velocity, and the acceleration is a rotational acceleration.

In order to provide these definitions, the present invention systematically provides and identification of the joint kinematics for the feet, lower legs, upper legs, pelvis, spine, shoulders and arms. Historically, kinematic models of the human skeleton have been formed as abstractions. In the current invention, the kinematic models are defined using Denavit-Hartenberg conventions, and the dynamic models are defined using the Jacobian conventions.

The present invention, in one aspect, provides systems and methods relating to an intelligent analytical system which uses user discrete characteristic data acquired from wearable and other mobile devices. The system has biometric authenticated data integrity, allows for personalized, group or population-based analysis of characteristic data and is not vulnerable to legacy computing systems, power failures, or unauthorized system access. The system, especially the server connected to multiple health or fitness-based databases, has the facility and learning capacity to assess and analyze a user's unique biometric loop signature data and other characteristics extrapolated from such loop signature data such as step count, step and stride length, stride to stride variability, center of force at any time interval for comparison against stored user data and kinematic chain models describing nominal gait, supination and pronation, and excessive supination and excessive pronation of the foot. The analytical system has the capability for targeted analysis of groupings of populated data characteristics such as gender, nationality, age, height, weight, foot shape such as Germanic or Celtic, foot type such as high arch or flat arch, posture, health and fitness. This analysis may be performed for research in movement and mobility biomarkers.

The present invention, in another aspect, provides the specification of a mathematical formalism that accurately specifies the position of each joint, the velocity of each joint, and the acceleration of each joint. When a joint is prismatic, then the velocity is a linear velocity and the acceleration is a linear acceleration. When a joint is rotational, then the velocity is a rotational velocity, and the acceleration is a rotational acceleration.

In order to provide these definitions, the invention systematically identifies the joint kinematics for the feet, lower legs, upper legs, pelvis, spine, shoulders and arms. Historically, kinematic models of the human skeleton have been formed as abstractions. In the current invention, the kinematic models are defined using Denavit-Hartenberg conventions, and the dynamic models are defined using the Jacobean conventions. The invention supports a number of skeletal joint types, including:

Pivot joints enable side-to-side motion. A pivot joint provides for rotation around only one axis. One bone rotates around another within a concave ring formed in the second bone. This ring is lined with a ligament to make the movement smooth. A pivot joint is what enables the neck to rotate to the Left and right and the forearm to make a rotating motion.

Hinge joints enable the bending of limbs. Hinge joints make it possible for limbs to flex and extend along only one axis. The bones fit together perfectly, one convex and the other concave. Elbows, fingers and toes are hinge joints. Certain hinge joints are more complicated to provide limited motion in other directions and are referred to as modified hinge joints. Multiple bones meet at the knee and ankle joints, making them more complex. The resulting structure allows for slight rotation of the knee and circular movement of the ankle.

Ball and Socket Joints enable complex rotation. Ball and socket joints are the most mobile, allowing a wide range of motion. These are the shoulder and hip joints. The bones in these joints fit together with a spherical bone sitting inside another bone that has a concave depression. This structure allows for bending and circular movement as well as rotation of the limb.

Condyloid joints enable joint twisting and bending. Condyloid or ellipsoidal joints are ball and socket joints that are elliptical rather than round, allowing bending and circular movement but rendering rotation impossible. This provides movement in two planes: bending and flexing as a hinge joint as well as a certain amount of rotation. These joints are found in the wrist and the base of the index finger.

Saddle joints are uniquely shaped and provide specifically constrained range of motion. Saddle joints are similar to condyloid joints, but the connecting bones are shaped more like interlocking saddles. This allows for a greater range of motion than hinge joints but does not allow complete rotation like ball and socket joints provide. The thumb is the best example of this.

Gliding Joints support the smooth slipping or sliding of two flat bones against each other and can freely glide past each other in any direction. Gliding joints are found in wrists, ankles and the spine.

Synovial joints enable the human body to move. These complicated connectors make it possible to move from place to place and to eat, work, and play. More than simply places where bones connect, they are a complicated assembly of bone, cartilage and fluid, held together with ligaments and tendons that connect to the muscles that make motion possible.

The spine pays a distinct role in the formation of Gait and is constrained by the inherent range of motion in each of the spinal joints.

Referring to FIG. 1, a block diagram of one embodiment of the present invention is illustrated. As can be seen, the system 10 includes a sensor module 20 coupled to a data processing module 30 and which may receive data from a storage module 40. In broad terms, the sensor module 20, having multiple sensors 20A, generates biometric data from the sensors (biometric data based on the user's gait) which is then sent to the data processing module 30. The data processing module 30 then processes the biometric data and retrieves signature data from the storage module 40. The signature data comprises data that was previously gathered from the user who is currently being diagnosed. The data processing module then compares the signature data with the biometric data gathered from the multiple sensors. If there are differences between the newly gathered data and the previously gathered data, the data processing module then determines if the differences are in line with known patterns which would indicate progression or regression of known user conditions of disease, sickness or injury. This conclusion would be based on gait-based biometric data which would indicate an improvement or decline in health and fitness or new health conditions.

As well, the system includes a communications module 50 that is coupled to the data processing module 30. The communications module 50 sends and/or receives communications regarding the comparison between the signature data and the data gathered from the sensors. The communications module 50 sends the data gathered to the data processing module 30 such that further data processing is performed remote from the user and/or the sensor module 20. The further data processing may be performed by a personal mobile device or by a server remote from the user's location and coupled to a network of distributed databases. By off-loading most of the post biometric authentication processing to a personal mobile device or to the remote server, the insole system does not need much processing capability. In one implementation, the sensor module simply operates as a data gathering device and all data processing is performed remote from the sensor module and/or the user. The data gathered by the sensor module may be transmitted to the data processing module for processing and/or to a database for later processing or to be part of one or more data sets.

It should be noted that the sensor module 20 has multiple sensors which gather data regarding a person's gait as well as other discrete user characteristics such as weight, step count, stride length, stride to stride variability, centre of force, applied force, cadence and lateral distance between the feet. In one embodiment, the sensor module is an insole positioned inside the user's shoe, with the insole having multiple discrete force sensors that detect the amount of force or pressure exerted on a section or region of the insole. With multiple regions on the insole and at least one sensor positioned on each region, a user's gait can be profiled as being the amount of pressure that the user exerts on each region over time as the user takes a step and correlated with embedded accelerometer and gyroscope data derived from the chip based computing module housed within the insole apparatus. A variant of this sensor module would have at least one strain gauge positioned such that the pressure exerted on each of the multiple regions of the foot are detected by the gauge with each region corresponding to a section of the strain gauge. With such an arrangement, each section of the strain gauge thus acts as a different discrete sensor and correlated with embedded accelerometer and gyroscope data derived from the chip-based computing module housed within the insole apparatus.

It should be noted that, in one embodiment, two insoles are used per user. This way, gait data may be gathered for each user foot. Data gathered from the user's left foot may be processed differently from data gathered from the user's right foot. The data gathered from each foot may then be combined to determine characteristics such as, for example, step count, cadence, velocity, centre of force, load bearing weight, standing weight and stride length. Alternatively, another embodiment only uses a single insole such that only one set of data is gathered per user. While the description below relates to a single insole, for a two-insole embodiment, both insoles would be similar to one another and would, preferably, each conform to the description and principles outlined below.

Figure 2A:
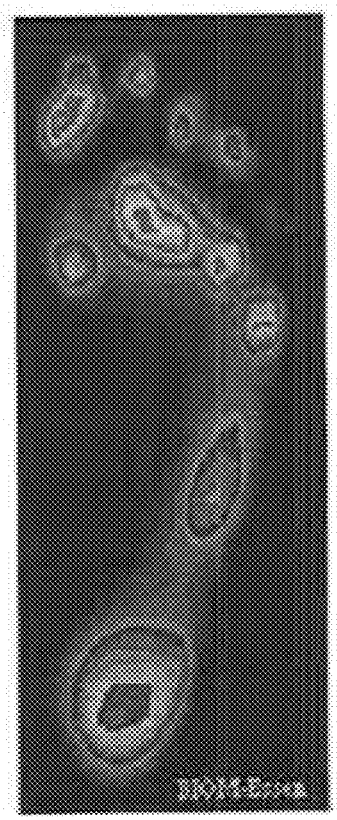
FIG. 2A is an image illustrating the different forces applied by a human foot as it takes a step.
Figure 2B:
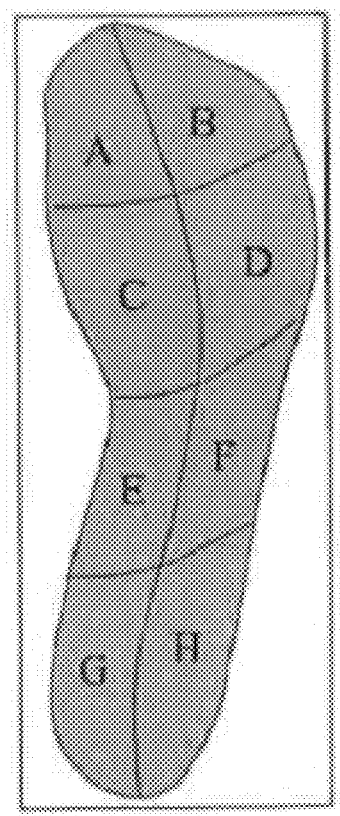
FIG. 2B is a diagram illustrating different zones on an insole with at least one sensor placement per zone according to one embodiment of another aspect of the invention.

Referring to FIGS. 2A and 2B, a schematic illustration of a number of discrete pressure zones on an insole is illustrated. FIG. 2A shows an imprint of a human foot and the unique pressure points for a specific person. FIG. 2B illustrates the location of 8 specific pressure zones or areas on one embodiment of a pressure sensing insole. Each zone in FIG. 2B has a pressure sensing pad or a number of sensors assigned to it such that the pressure exerted on each zone can be measured. A variant of this sensor module would have, instead of discrete sensor pads at each zone, a single strain gauge positioned as described above.

In the above embodiment, each sensor in the sensor module produces a signal linearly proportional to the force being applied to the sensor. Preferably, each sensor or zone would have a data channel dedicated to its readings for transmitting those readings to the data processing module. Alternatively, in one implementation, the readings can be time division multiplexed on to a single data line from the sensor module to the data processing module. In this implementation, the data is passed through a single A/D converter to produce multiplexed channels, one for each sensor. Of course, while there are eight zones in FIG. 2B, other variants may have more than or less than eight zones.

Regarding the data stream produced when the user is walking, in one embodiment, each sensor produces several hundred samples equating to approximately ten steps taken by the user. This data stream is then saved and examined by the data processing module and the actual step points are determined. Each step is identified, and the saved data stream resampled at a precise rate of approximately 100 samples per step.

It should be noted that multiple parameters regarding the user's gait can be extracted from the data produced by the sensor module depending on the type of sensors used in the sensor module. These parameters can then be used as points of comparison with the signature (or characteristic) data mentioned above. Some of these parameters may be:

Actual forces
Relative (normalized) forces.
Ratios between the peak forces in the eight sensor zones
Relative timing between forces on each sensor (strike and release sequence)
Average rate of change of force on each sensor zone
Maximum rate of change of force on each sensor zone
Frequency spectrum of the waveform from each sensor (ratio of values of harmonics derived from a Fourier transform)
Heel strike and toe lift off impact forces in the three axes.
Data waveform shape matching (waveform shape matching)

The parameters extracted from the data stream may then be compared directly or indirectly with the signature data noted above.

In one comparison scheme, the parameters extracted are used to derive a shape or loop, the characteristics of which can the compared with characteristics of a signature loop or shape. The use of a loop or shape allows for an indirect comparison between the data read by the sensor module and the signature or characteristic data. As well, it allows for more complex comparison schemes and for easier use of tolerances in the comparison.

For this comparison scheme, data from two different sensors are read by the data processing module. The two data sets (one from a first sensor and a second from a second sensor) are correlated with one another to synchronize the readings. This is done so that the data readings are synchronized in their time indices. Once synchronized, readings taken at approximately the same time index are matched with one another. Thus the result is that a data reading from sensor A taken at time t1 is mated with a data reading from sensor B taken at time t1. The mating step results in a set of pairs of data readings from two different sensors.

It should be noted that a preferable preliminary step to the correlation step is that of applying a low pass filter to both sets of data. Such a low pass filter would remove the low frequency components of the signals and would provide cleaner and easier to process signals.

As an example of the processing performed on the data streams received from the sensor modules, FIGS. 3-8 are provided to aid in the understanding of the process. Prior to any processing, data streams are first received from all of the sensors for a given fixed duration. For each sensor, the data stream for the given duration is saved by the data processing module. The resulting waveform for each sensor is then partitioned to determine discrete steps taken by the user. If the sensors are force/pressure sensors, this partitioning may be done by searching for peaks and valleys in the waveform. Each peak would denote a maximum force applied to the sensor and each valley would denote a minimum (if not absence) of force. Each step can then be seen as two valleys with a peak in between, representing the user's foot in the air, the actual step, and then user lifting his/her foot again. Alternatively, depending on how the system is configured, each step might be seen as two peaks bookending a valley.

Figure 3:
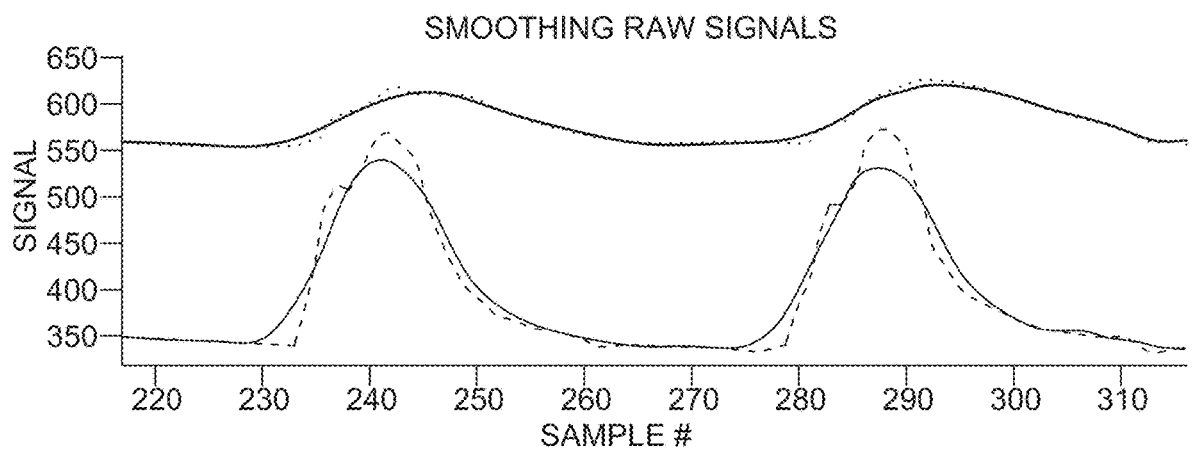
FIG. 3 illustrates raw data waveforms and data waveforms after a low pass filter has been applied.

Referring to FIG. 3, two raw data streams is shown at the bottom of the plot. After a low pass filter is applied to the signals, the smoother waveforms are shown at the top half of FIG. 3. From FIG. 3, one can see maximum force applied to the force pads for the two steps captured by the waveforms.

Once the discrete steps have been delineated in the data received from each of the sensors, each step for each sensor is then resampled to arrive at a predetermined number of data samples for each step. For the resampling, each sample is for a predetermined time frame and at a predetermined point in time in the current step. As an example, if each step lasts approximately 0.1 sec and 100 samples per step are desired, then the first sample is taken at the first one thousandth of a second in the waveform and the second sample is taken at the second one thousandth of a second and so on and so forth. This method essentially synchronizes all the samples such that it would be simple to determine all samples (from all the sensor readings) taken at the first one thousandth of a second or all samples taken at the first fiftieth one thousandths of a second as the relevant samples would all be similarly time indexed.

Once the different data waveforms from the different sensors have been synchronized, any two of the sensors and the data they produced can be selected for comparison with the signature data noted above and which may be stored in the data storage module. Depending on the configuration of the system, the signature or characteristic data stored in the data storage module may take numerous forms. In one example, multiple data sets/pairs (either filtered or as raw data) from the user may be stored so that a signature loop may be derived from the signature data whenever the characteristics of that signature loop are required. For this example, all the data pairs from all sensors would be stored so that any two sensors may be selected. Alternatively, the specific characteristics of the signature loop may be stored as the signature or characteristic data if one wanted to dispense with determining the signature loop every time a comparison needs to be made. As another alternative, only the data relating to the average signature loop derived from the user may be stored as signature data. Of course, if multiple sensors are to be used, then most possible average signature loops from the user data would be stored.

In one other alternative, all the raw data (either filtered or not) from the user's steps may be stored as signature data. Such a configuration would allow for the greatest amount of flexibility as the system could randomly select any two of the sensors to be used and the signature data from the user would be available for those two sensors. As noted above, this configuration would require that the signature loop be calculated every time a comparison is required. The signature data may, if desired, be stored in encrypted format.

Once two of the sensors are selected from the sensors available in the sensor module (in this example the sensor module has 8 sensors, one for each of the eight zones illustrated in FIG. 2B), the resampled data for those two sensors are then mated with one another. This means that each time indexed sampling will have two points of data, one for the first sensor and another for the other sensor. These pairs of sensor readings can thus be used to create a characteristic loop. As an example, if sensors A and B are used and n denotes an index, then A[n] denotes the nth sampled reading from the waveform received from sensor A for a specific step. Similarly, B [n] is the nth sampled reading from the waveform received from sensor B for the same specific step. {A[n], B[n]} thus constitutes a data pair for the nth reading for that particular step. Plotting all the data pairs for a particular step, with readings from one sensor being on one axis and readings from the other sensor on the axis, results in an angled loop-like plot (see FIGS. 4-8 as examples). For pressure/force readings, this is not surprising as the force exerted by the foot in a particular step increases to a maximum and then decreases to as minimum as the person increases the weight on the place on the foot and then removes that weight as the step progresses.

Figure 4:
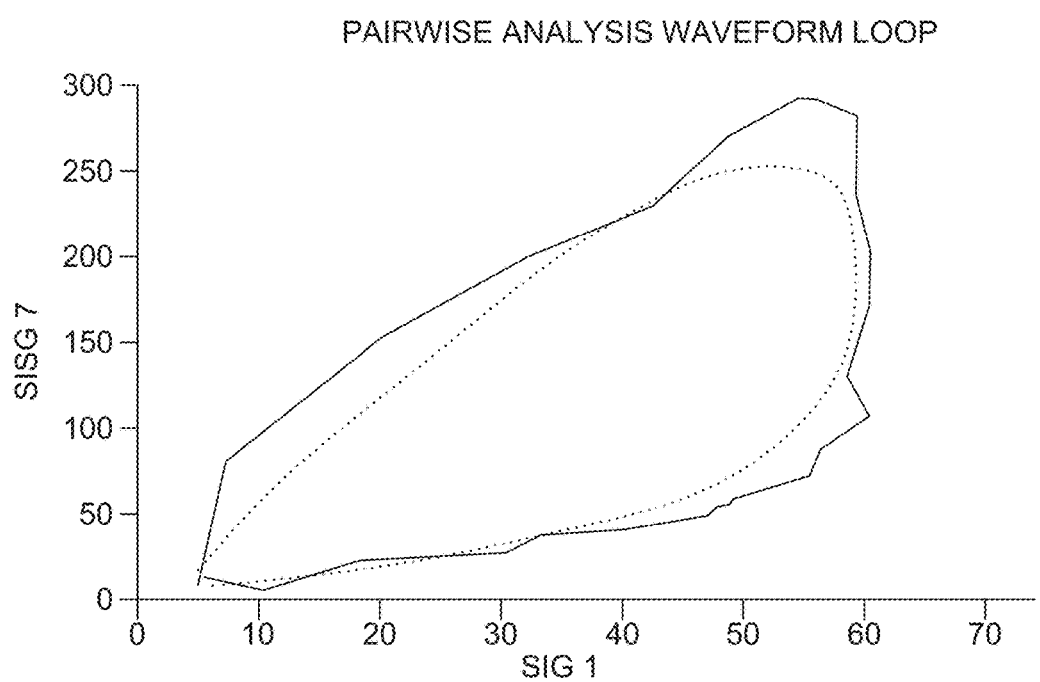
FIG. 4 illustrates loops plotted using raw data and filtered data.

Once the data pairs have been created, a plot of the resulting loop can be made. As noted above, FIG. 3 shows the waveforms for two signals—the lower waveform being the raw data stream waveforms for 2 signals and the upper waveforms for the same 2 signals after a low pass filter has been applied. FIG. 4 shows a plot of the two sets of waveforms in FIG. 3. One loop in FIG. 4 is derived from the raw signal waveforms in FIG. 3 while the other loop is derived from the low pass filtered waveform in FIG. 3. As can be seen in FIG. 4, a smoother loop is produced by the low-pass filtered signals.

It should be noted that the x-axis in FIG. 4 contains the values gathered from the first sensor selected while the y-axis contains the values gathered from the second selected sensor. It should be noted that while the embodiment discussed uses only a pair of sensors, the concept is applicable for 3, 4, or any number of sensors. If data from 3 sensors were used, then, instead of a 2D loop, a 3D loop may be created as a characteristic loop.

Figure 5:
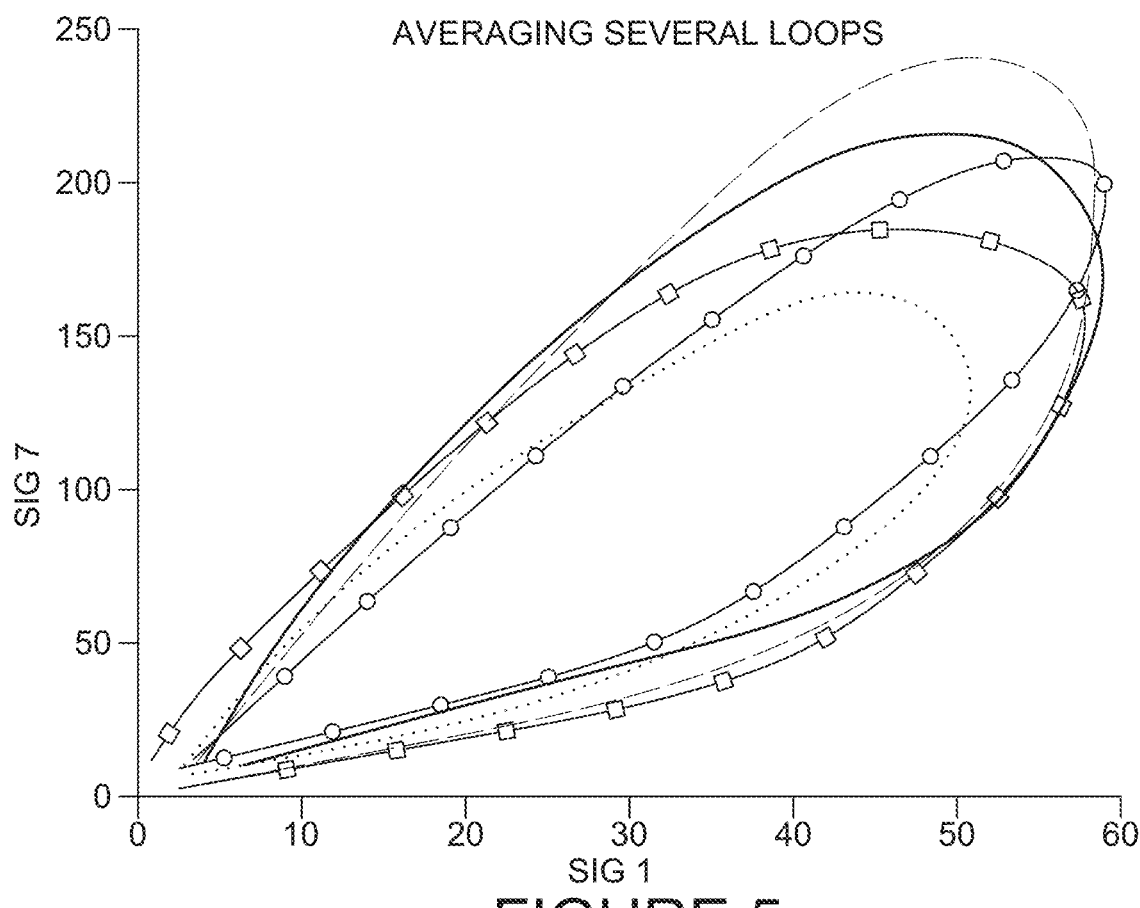
FIG. 5 illustrates a number of characteristics for different sets of data from the same user, as well as an average characteristic loop derived from the other loops.

It should be noted that a loop can be formed for each one of the steps captured by the sensors. An averaged loop can be derived from the various loops formed from all the steps captured by the sensors. Referring to FIG. 5, the various loops from the various steps can be seen on the plot. An average loop (see darker loop in FIG. 5) is derived from all the loops captured using the low pass filtered waveforms. Multiple methods may be used to determine the average loop. However, in one embodiment, the points for the average loop are derived by averaging the various readings for each particular time index. As such, if the data pairs are as (An[i],Bn[i]) with An[i] denoting the nth reading for sensor A at time index i and Bn[i] denoting the nth reading for sensor B at time index i, then to derive the data reading for sensor A for the average loop for time index i, one merely averages all the An[i] where n=1, 2, 3, etc., etc. Similarly, for data reading for sensor B for the average loop for time index i, one merely averages all the Bn[i] where n=1, 2, 3, etc., etc. By doing this for all the multiple time indices, an average loop is derived from all the characteristic loops.

Figure 6:
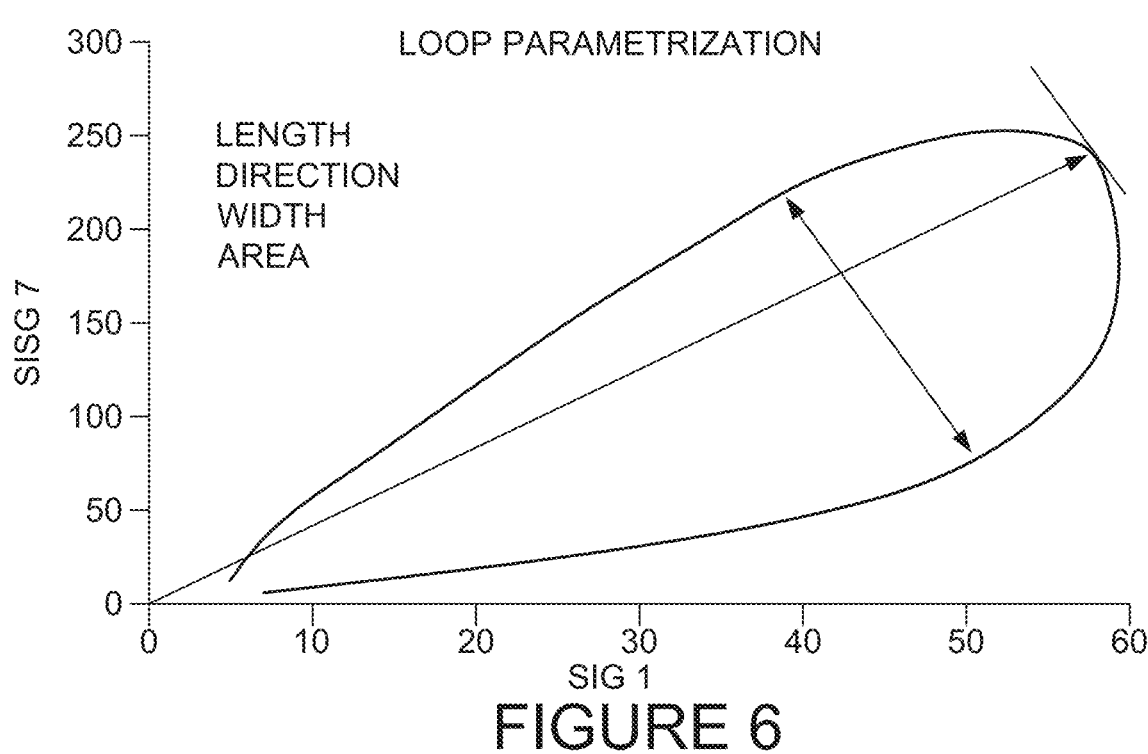
FIG. 6 illustrates the different characteristics which may be derived from the characteristic loops.

Once the average loop has been derived, the characteristics of that average loop can be determined. Referring to FIG. 6, some of the characteristics of the average loop can be seen. The length of the loop (measured from the origin), the width of the widest part of the loop, and the area occupied by the loop are just some of the characteristics which may be determined from the loop. As well, the direction of the loop (whether it develops in a clockwise or anti-clockwise manner) may also be seen as a characteristic of the loop. Another possible characteristic of the loop may be the angle between a ray from the origin to the farthest point of the loop and one of the axes of the plot. Additional characteristics of these loops may, of course, be used depending on the configuration of the system.

Figure 7:
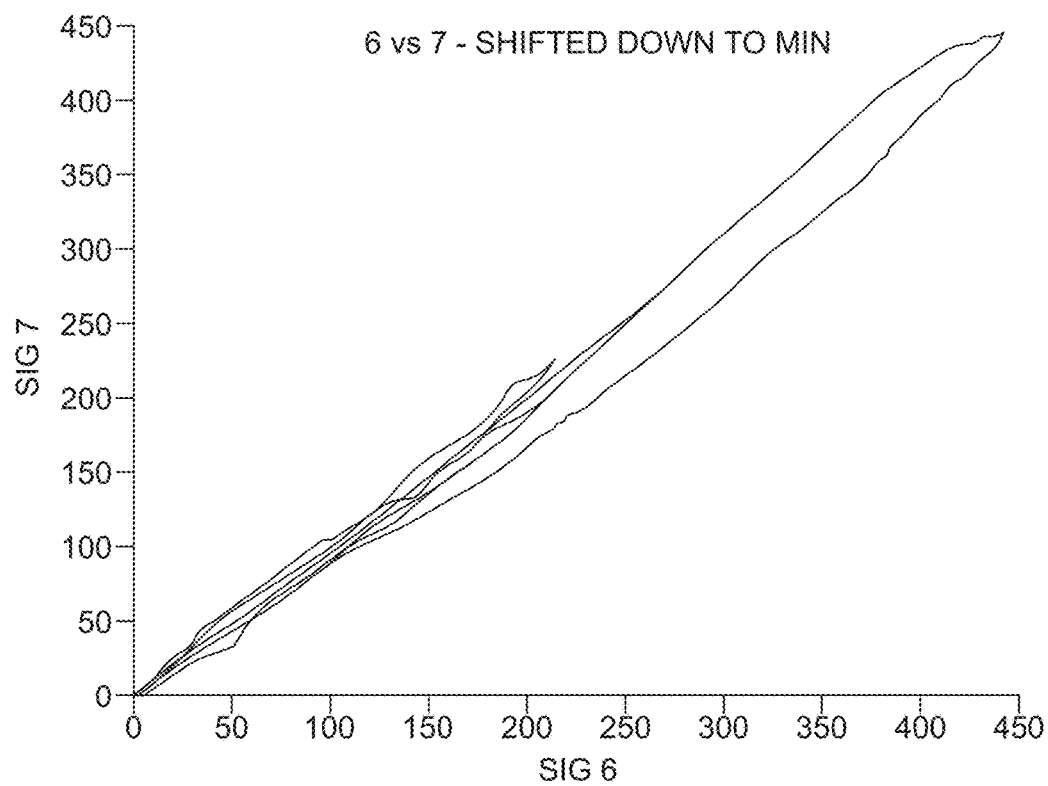
FIG. 7 illustrates characteristic loops using highly correlated data.

As another example of possible loops, FIG. 7 shows loops resulting from highly correlated data from the sensors. Such highly correlated data may produce loops that, at first glance, may not be overly useful. However, even such lopsided loops may yield useful characteristics. As an example, the amplitude from the furthest point may be used for an initial assessment of static of dynamic weight distribution.

Once the average loop for the steps captured by the sensors is determined, the characteristics for this average loop can be derived. Once derived, the same process is applied to the signature data stored in the storage module. The characteristics for the resulting signature loop (from the signature data) are then compared to the characteristics of the average loop from the data acquired from the sensors.

Figure 8:
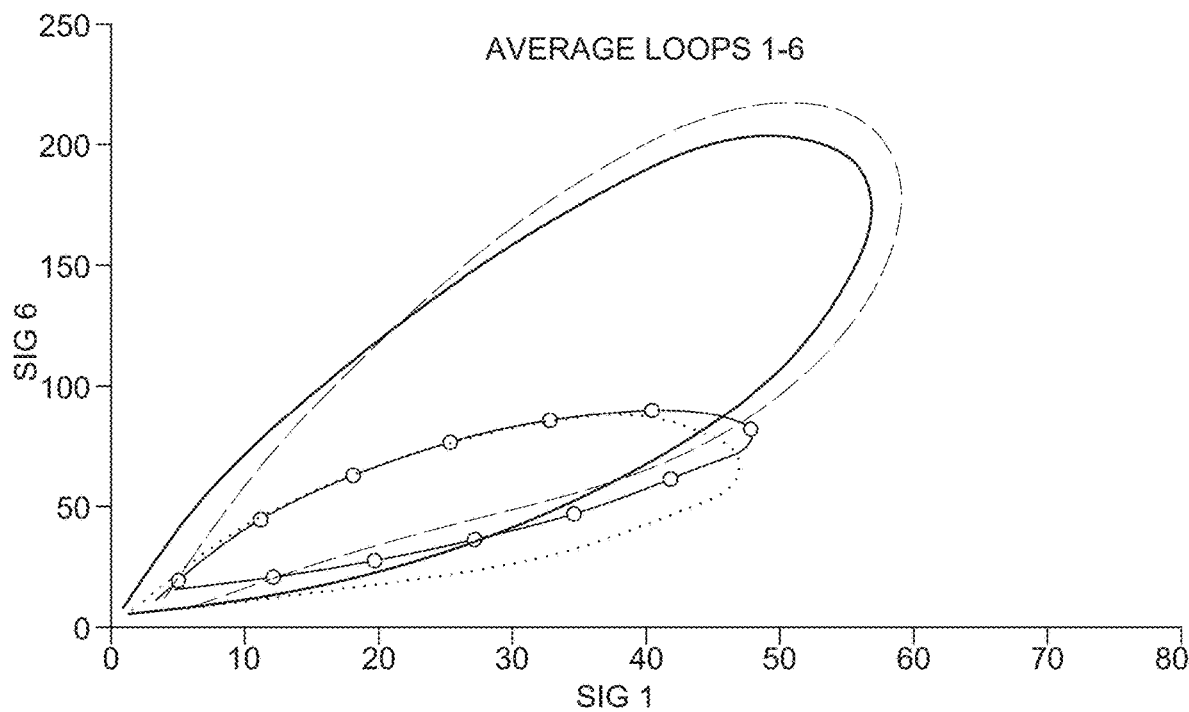
FIG. 8 shows average characteristic loops for different users.

Referring to FIG. 8, a comparison of two average loops from the gait of two individuals is illustrated. As can be seen, the characteristics of the two loops are quite different. One loop is clearly larger (more area), longer (length of loop), and wider (width at widest of the loops) than the other loop. It should be noted that custom tolerances can be applied to the comparison. Depending on the tolerance applied, the comparison can be successful (the characteristics match within the tolerances) or unsuccessful (even within the tolerances, there is no match). It should be noted that, as noted above, comparisons can be made for loops from a single user with data taken at different times. As an example, a user may have gait data taken at a first use of the system. Later gait data sets can then be taken for the same user at subsequent uses of the system. The loops derived from the initial gait data set and the subsequent gait data sets can then be compared to determine how a particular fitness program, treatment regimen, or physical condition has positively or negatively affected that user's gait over time.

Regarding tolerances, these can be preprogrammed into the system and can be determined when the signature data is gathered. As an example, a tolerance of 15% may be acceptable for some users while a tolerance of only 5% may be acceptable. This means that if the calculated characteristic of the average loop is within 15% of the calculated characteristic of the signature loop, then a match is declared. A match would indicate that there is no relevant difference between the loops being compared. Similarly, if a tolerance of only 5% is used, then if the calculated characteristic of the average loop is within 5% of the calculated characteristic of the signature loop, then a match is declared. Of course, if the calculated characteristic of the average loop is not within the preprogrammed tolerance of the calculated characteristic of the signature loop, then a non-match is declared. A non-match would indicate that there is a relevant difference between the loops being compared. A match may indicate that, for example, a fitness program, treatment regimen, or condition has not affected a user's gait between the time the first set of gait data was gathered to the time the second set of gait data was gathered. A non-match may, of course, indicate that the fitness program, treatment regimen, or condition has affected the user's gait.

It should also be noted that, in addition to the tolerances noted above, the system may use a graduated system of matches or matching. This would mean that a level of confidence may be assigned to each match, a high level of confidence being an indication that there is a higher likelihood that there is a match between the two sets of data derived from the average loop and the signature loop. A match can then be declared once the level of confidence assigned is higher than a predetermined level. A non-match can similarly be declared once the level of confidence is lower than a predetermined level. A level of indecision can be declared when the level of confidence is between the two pre-set levels for match and non-match. If a set of data falls within the gray area or an area of indecision between the two pre-set levels, then more data can be retrieved from the sensors and this data can be processed as above to arrive at a determination of a match or a non-match.

It should further be noted that, as an alternative, instead of matching or not matching two loops derived from a user's gait data, the amount of difference between the two loops can be determined. A significant difference between the characteristics of the two loops, preferably derived from data gathered from the same user using the same sensors in the sensor module at different times, would indicate a change of some sort. A significant difference between such two loops would indicate a significant change from the time the first data set was gathered to the time the second data set was gathered. As noted above, this could indicate that a fitness program, treatment regimen, or condition was having an effect on the user's gait. It may also indicate that a user's physical or medical condition is either progressing or regressing. The characteristics for which a difference may be found may, as noted above, include the size of the loops, the angle of the loops to one of the axes of the plot, the perimeter of the loops, the area covered by the loops, as well as other characteristics. A tolerance may, of course, be built into the comparison subroutine. As an example, if the tolerance is set at 2%, if a characteristic of two loops are within 1% (i.e. less than 2%) of each other (e.g. the sizes of the two loops) then no difference is concluded.

For greater clarity, the difference between two loops may be quantified and, depending on how great the differences are, alarms or other steps may be taken. As an example, if the area of a loop derived from a user's initial data set is compared with the area of a loop derived from a data set gathered a few months later, the differences may be significant. If there is no appreciable difference, then one can conclude that no change has occurred in the user's condition. If, on the other hand, the second data set has a much larger area (e.g. 25% greater area than the area covered by the loop from the first data set), this may indicate that the user is walking slower or that the user is placing more pressure on his feet with each step. Depending on the user's physical condition, this may indicate a progression (getting worse) or a regression (getting better) of that condition. It may also indicate that a fitness program or treatment regimen being used may or may not be effective. A threshold may thus be programmed so that if the difference in value of a characteristic being compared between two loops exceeds a specific amount or percentage, an alarm may be activated.

Refined comparison of gait data to existing gait models can also be performed. Kinematic and dynamic models are developed by specifying kinematic models of the joints contributing to ambulation, including the phalanges, metatarsals, tarsals, tibia/fibula, femur, pelvis, spinal vertebrae, and arm motion. Loop data is translated into pressure indicators, where pressure is propagated through the kinematic model.

The kinematic data is expressed as joint position and joint angles for every bone that participates in ambulation.

Dynamic joint data is modeled using a Jacobian matrix of partial differential equations of the joint velocities and joint accelerations for each joint that participates in ambulation. With the kinematic and dynamic models, comparisons of current data, registration data, and nominal data can be conducted to confirm that a user's performance has not altered from a known state.

In addition, kinematic and dynamic joint data comparisons can be made to known gait models, such as those derived from particular diseases and their unique gait data observed and collected from known patient observations. Models derived from these observations are compared by position in X, Y, Z, linear velocity in X', Y', Z', linear acceleration in X", Y", Z", where prismatic or sliding joints are observed. In the case of rotational joints, the joint positions in $\theta_x$, $\theta_y$, and $\theta_z$, joint velocities, in $\omega x$, $\omega y$, and $\omega z$, and joint accelerations in $\alpha_x$, $\alpha_y$, and $\alpha_z$ are used.

In addition, the coordinate reference frame for each of the 187 joints in the analytical system configuration is expressed below. This analytical system configuration represents shuffling, walking, running, jumping, or dancing behaviour. As well, the configuration may be used to represent biomarkers for disease detection, biomarkers for disease progression or regression, injury, sickness and/or side effects of prescribed pharmacologies. The description of each of the 187 joints and the Jacobian matrices for each joint as provided below.

Joint 1 connects the Right Foot, $1^{st}$ Toe, Hallux, Distal Phalange to the Right Foot, $1^{st}$ Toe, Proximal Phalange. The $d_1$ link length of the Hallux runs collinear with the hallux centroid running from the Hallux base to the tip of the $1^{st}$ Proximal Phalange along the X axis. The matrices for this joint are:

$$A_1 = \begin{bmatrix} \cos\theta_1 & -\sin\theta_1 & 0 & 0 \\ \sin\theta_1 & \cos\theta_1 & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_1 \\ 0 & 0 & 0 & 1 \end{bmatrix} \begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_1 & -\sin\alpha_1 & 0 \\ 0 & \sin\alpha_1 & \cos\alpha_1 & 0 \\ 0 & 0 & 0 & 1 \end{bmatrix}$$

$$A_1 = \begin{bmatrix} \cos\theta_1 & -\sin\theta_1\cos\alpha_1 & \sin\theta_1\sin\alpha_1 & a_1\cos\theta_1 \\ \sin\theta_1 & \cos\theta_1\cos\alpha_1 & -\cos\theta_1\sin\alpha_1 & a_1\sin\theta_1 \\ 0 & \sin\alpha_1 & \cos\alpha_1 & d_1 \\ 0 & 0 & 0 & 1 \end{bmatrix}$$

Joint 2 connects the Right foot, $2^{nd}$ toe, Distal Phalange to the Right foot $2^{nd}$ toe Middle Phalange. The $d_2$ link length of the $2^{nd}$ Distal Phalange runs collinear with the $2^{nd}$ Distal Phalange centroid running from the $2^{nd}$ Distal Phalange base to the tip of the $2^{nd}$ Middle Phalange along the X axis. The matrices for this joint are:

$$A_2 = \begin{bmatrix} \cos\theta_2 & -\sin\theta_2 & 0 & 0 \\ \sin\theta_2 & \cos\theta_2 & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_2 \\ 0 & 0 & 0 & 1 \end{bmatrix} \begin{bmatrix} 1 & 0 & 0 & a_2 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_2 & -\sin\alpha_2 & 0 \\ 0 & \sin\alpha_2 & \cos\alpha_2 & 0 \\ 0 & 0 & 0 & 1 \end{bmatrix}$$

$$A_2 = \begin{bmatrix} \cos\theta_2 & -\sin\theta_2\cos\alpha_2 & \sin\theta_2\sin\alpha_2 & a_2\cos\theta_2 \\ \sin\theta_2 & \cos\theta_2\cos\alpha_2 & -\cos\theta_2\sin\alpha_2 & a_1\sin\theta_2 \\ 0 & \sin\alpha_2 & \cos\alpha_2 & d_2 \\ 0 & 0 & 0 & 1 \end{bmatrix}$$

Joint 3 connects the Right foot, $3^{rd}$ toe, Distal Phalange to the Right foot, $3^{rd}$ toe Middle Phalange. The $d_3$ link length of the $3^{rd}$ Distal Phalange runs collinear with the $3^{rd}$ Distal Phalange centroid running from the $3^{rd}$ Distal Phalange base to the tip of the $3^{rd}$ Middle Phalange along the X axis. The matrices for this joint are:

$$A_3 = \begin{bmatrix} \cos\theta_3 & -\sin\theta_3 & 0 & 0 \\ \sin\theta_3 & \cos\theta_3 & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_3 \\ 0 & 0 & 0 & 1 \end{bmatrix} \begin{bmatrix} 1 & 0 & 0 & a_3 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_3 & -\sin\alpha_3 & 0 \\ 0 & \sin\alpha_3 & \cos\alpha_3 & 0 \\ 0 & 0 & 0 & 1 \end{bmatrix}$$

$$A_3 = \begin{bmatrix} \cos\theta_3 & -\sin\theta_3\cos\alpha_3 & \sin\theta_3\sin\alpha_3 & a_2\cos\theta_3 \\ \sin\theta_3 & \cos\theta_3\cos\alpha_3 & -\cos\theta_3\sin\alpha_3 & a_1\sin\theta_3 \\ 0 & \sin\alpha_3 & \cos\alpha_3 & d_3 \\ 0 & 0 & 0 & 1 \end{bmatrix}$$

Joint 4 connects the Right foot, $4^{th}$ toe, Distal Phalange to the Right foot, $4^{th}$ toe, Middle Phalange. The $d_4$ link length of the $4^{th}$ Distal Phalange runs collinear with the $4^{th}$ Distal Phalange centroid running from the $4^{th}$ Distal Phalange base to the tip of the $4^{th}$ Middle Phalange along the X axis.

$$A_4 = \begin{bmatrix} \cos\theta_4 & -\sin\theta_4 & 0 & 0 \\ \sin\theta_4 & \cos\theta_4 & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_4 \\ 0 & 0 & 0 & 1 \end{bmatrix} \begin{bmatrix} 1 & 0 & 0 & a_4 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_4 & -\sin\alpha_4 & 0 \\ 0 & \sin\alpha_4 & \cos\alpha_4 & 0 \\ 0 & 0 & 0 & 1 \end{bmatrix}$$

-continued $$A_4 = \begin{bmatrix} \cos\theta_4 & -\sin\theta_4\cos\alpha_4 & \sin\theta_4\sin\alpha_4 & a_4\cos\theta_4 \\ \sin\theta_4 & \cos\theta_4\cos\alpha_4 & -\cos\theta_4\sin\alpha_4 & a_4\sin\theta_4 \\ 0 & \sin\alpha_4 & \cos\alpha_4 & d_4 \\ 0 & 0 & 0 & 1 \end{bmatrix}$$

Joint 5 connects the Right foot, $5^{th}$ toe, Distal Phalange to the Right foot, $5^{th}$ toe, Middle Phalange. The $d_5$ link length of the $5^{th}$ Distal Phalange runs collinear with the $5^{th}$ Distal Phalange centroid running from the $5^{th}$ Distal Phalange base to the tip of the $5^{th}$ Middle Phalange along the X axis. The matrices for this joint are as follows:

$$A_5 = \begin{bmatrix} \cos\theta_5 & -\sin\theta_5 & 0 & 0 \\ \sin\theta_5 & \cos\theta_5 & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_5 \\ 0 & 0 & 0 & 1 \end{bmatrix}\begin{bmatrix} 1 & 0 & 0 & a_5 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_5 & -\sin\alpha_5 & 0 \\ 0 & \sin\alpha_5 & \cos\alpha_5 & 0 \\ 0 & 0 & 0 & 1 \end{bmatrix}$$

$$A_5 = \begin{bmatrix} \cos\theta_5 & -\sin\theta_5\cos\alpha_5 & \sin\theta_5\sin\alpha_5 & a_5\cos\theta_5 \\ \sin\theta_5 & \cos\theta_5\cos\alpha_5 & -\cos\theta_5\sin\alpha_5 & a_5\sin\theta_5 \\ 0 & \sin\alpha_5 & \cos\alpha_5 & d_5 \\ 0 & 0 & 0 & 1 \end{bmatrix}$$

Joint 6 connects the Right foot, $2^{nd}$ toe, Middle Phalange to the Right foot, $2^{nd}$ toe, Proximal Phalange. The $d_7$ link length of the $2^{nd}$ Middle Phalange runs collinear with the $2^{nd}$ Middle Phalange centroid running from the $2^{nd}$ Middle Phalange base to the tip of the $2^{nd}$ Proximal Phalange along the X axis.

$$A_6 = \begin{bmatrix} \cos\theta_6 & -\sin\theta_6 & 0 & 0 \\ \sin\theta_6 & \cos\theta_6 & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_6 \\ 0 & 0 & 0 & 1 \end{bmatrix}\begin{bmatrix} 1 & 0 & 0 & a_6 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_6 & -\sin\alpha_6 & 0 \\ 0 & \sin\alpha_6 & \cos\alpha_6 & 0 \\ 0 & 0 & 0 & 1 \end{bmatrix}$$

$$A_6 = \begin{bmatrix} \cos\theta_6 & -\sin\theta_6\cos\alpha_6 & \sin\theta_6\sin\alpha_6 & a_6\cos\theta_6 \\ \sin\theta_6 & \cos\theta_6\cos\alpha_6 & -\cos\theta_6\sin\alpha_6 & a_6\sin\theta_6 \\ 0 & \sin\alpha_6 & \cos\alpha_6 & d_6 \\ 0 & 0 & 0 & 1 \end{bmatrix}$$

Joint 7 connects the right foot, $3^{rd}$ toe, Middle Phalange to Right foot, $3^{rd}$ toe, Proximal Phalange. The $d_7$ link length of the $3^{rd}$ Middle Phalange runs collinear with the $3^{rd}$ Middle Phalange centroid running from the $3^{rd}$ Middle Phalange base to the tip of the $3^{rd}$ Proximal Phalange along the X axis.

$$A_7 = \begin{bmatrix} \cos\theta_7 & -\sin\theta_7 & 0 & 0 \\ \sin\theta_7 & \cos\theta_7 & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_7 \\ 0 & 0 & 0 & 1 \end{bmatrix}\begin{bmatrix} 1 & 0 & 0 & a_1 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_7 & -\sin\alpha_7 & 0 \\ 0 & \sin\alpha_7 & \cos\alpha_7 & 0 \\ 0 & 0 & 0 & 1 \end{bmatrix}$$

$$A_7 = \begin{bmatrix} \cos\theta_7 & -\sin\theta_7\cos\alpha_7 & \sin\theta_7\sin\alpha_7 & a_7\cos\theta_7 \\ \sin\theta_7 & \cos\theta_7\cos\alpha_7 & -\cos\theta_7\sin\alpha_7 & a_7\sin\theta_7 \\ 0 & \sin\alpha_7 & \cos\alpha_7 & d_7 \\ 0 & 0 & 0 & 1 \end{bmatrix}$$

Joint 8 connects the Right foot, $4^{th}$ toe, Middle Phalange to the Right foot, $4^{th}$ toe, Proximal Phalange. The $d_8$ link length of the $4^{th}$ Middle Phalange runs collinear with the $4^{th}$ Proximal Phalange centroid running from the $4^{th}$ Middle Phalange base to the tip of the $4^{th}$ Proximal Phalange along the X axis.

$$A_8 = \begin{bmatrix} \cos\theta_8 & -\sin\theta_8 & 0 & 0 \\ \sin\theta_8 & \cos\theta_8 & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_8 \\ 0 & 0 & 0 & 1 \end{bmatrix}\begin{bmatrix} 1 & 0 & 0 & a_8 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_8 & -\sin\alpha_8 & 0 \\ 0 & \sin\alpha_8 & \cos\alpha_8 & 0 \\ 0 & 0 & 0 & 1 \end{bmatrix}$$

$$A_8 = \begin{bmatrix} \cos\theta_8 & -\sin\theta_8\cos\alpha_8 & \sin\theta_8\sin\alpha_8 & a_8\cos\theta_8 \\ \sin\theta_8 & \cos\theta_8\cos\alpha_8 & -\cos\theta_8\sin\alpha_8 & a_8\sin\theta_8 \\ 0 & \sin\alpha_8 & \cos\alpha_8 & d_8 \\ 0 & 0 & 0 & 1 \end{bmatrix}$$

Joint 9 connects the Right foot, $5^{th}$ toe, Middle Phalange to the Right foot, $5^{th}$ toe Proximal Phalange. The $d_9$ link length of the $5^{th}$ Middle Phalange runs collinear with the $5^{th}$ Proximal Phalange centroid running from the $5^{th}$ Middle Phalange base to the tip of the $5^{th}$ Proximal Phalange along the X axis.

$$A_9 = \begin{bmatrix} \cos\theta_9 & -\sin\theta_9 & 0 & 0 \\ \sin\theta_9 & \cos\theta_9 & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_9 \\ 0 & 0 & 0 & 1 \end{bmatrix}\begin{bmatrix} 1 & 0 & 0 & a_9 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_9 & -\sin\alpha_9 & 0 \\ 0 & \sin\alpha_9 & \cos\alpha_9 & 0 \\ 0 & 0 & 0 & 1 \end{bmatrix}$$

$$A_9 = \begin{bmatrix} \cos\theta_9 & -\sin\theta_9\cos\alpha_9 & \sin\theta_9\sin\alpha_9 & a_9\cos\theta_9 \\ \sin\theta_9 & \cos\theta_9\cos\alpha_9 & -\cos\theta_9\sin\alpha_9 & a_9\sin\theta_9 \\ 0 & \sin\alpha_9 & \cos\alpha_9 & d_9 \\ 0 & 0 & 0 & 1 \end{bmatrix}$$

Joint 10 connects the Right foot $1^{st}$ toe Proximal Phalange to the Right foot, $1^{st}$ toe Metatarsal. The $d_{10}$ link length of the $1^{st}$ Proximal Phalange runs collinear with the $1^{st}$ Proximal Phalange centroid running from the $1^{st}$ Proximal Phalange base to the tip of the $1^{st}$ Metatarsal along the X axis.

$$A_{10} = \begin{bmatrix} \cos\theta_{10} & -\sin\theta_{10} & 0 & 0 \\ \sin\theta_{10} & \cos\theta_{10} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{10} \\ 0 & 0 & 0 & 1 \end{bmatrix} \begin{bmatrix} 1 & 0 & 0 & a_{10} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{10} & -\sin\alpha_{10} & 0 \\ 0 & \sin\alpha_{10} & \cos\alpha_{10} & 0 \\ 0 & 0 & 0 & 1 \end{bmatrix}$$

$$A_{10} = \begin{bmatrix} \cos\theta_{10} & -\sin\theta_{10}\cos\alpha_{10} & \sin\theta_{10}\sin\alpha_{10} & a_{10}\cos\theta_{10} \\ \sin\theta_{10} & \cos\theta_{10}\cos\alpha_{10} & -\cos\theta_{10}\sin\alpha_{10} & a_{10}\sin\theta_{10} \\ 0 & \sin\alpha_{10} & \cos\alpha_{10} & d_{10} \\ 0 & 0 & 0 & 1 \end{bmatrix}$$

Joint 11 connects the Right foot, $2^{nd}$ toe, Proximal Phalange to the Right foot, $2^{nd}$ toe Metatarsal. The $d_{10}$ link length of the $2^{nd}$ Proximal Phalange runs collinear with the $2^{nd}$ Proximal Phalange centroid running from the $2^{nd}$ Proximal Phalange base to the tip of the $2^{nd}$ Metatarsal along the X axis.

$$A_{11} = \begin{bmatrix} \cos\theta_{11} & -\sin\theta_{11} & 0 & 0 \\ \sin\theta_{11} & \cos\theta_{11} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{11} \\ 0 & 0 & 0 & 1 \end{bmatrix} \begin{bmatrix} 1 & 0 & 0 & a_{11} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{11} & -\sin\alpha_{11} & 0 \\ 0 & \sin\alpha_{11} & \cos\alpha_{11} & 0 \\ 0 & 0 & 0 & 1 \end{bmatrix}$$

$$A_{11} = \begin{bmatrix} \cos\theta_{11} & -\sin\theta_{11}\cos\alpha_{11} & \sin\theta_{11}\sin\alpha_{11} & a_{11}\cos\theta_{11} \\ \sin\theta_{11} & \cos\theta_{11}\cos\alpha_{11} & -\cos\theta_{11}\sin\alpha_{11} & a_{11}\sin\theta_{11} \\ 0 & \sin\alpha_{11} & \cos\alpha_{11} & d_{11} \\ 0 & 0 & 0 & 1 \end{bmatrix}$$

Joint 12 connects the Right foot, $3^{rd}$ toe, Proximal Phalange to the Right foot, $3^{rd}$ toe Metatarsal. The $d_{12}$ link length of the $3^{rd}$ Proximal Phalange runs collinear with the $3^{rd}$ Proximal Phalange centroid running from the $3^{rd}$ Proximal Phalange base to the tip of the $3^{rd}$ Metatarsal along the X axis.

$$A_{12} = \begin{bmatrix} \cos\theta_{12} & -\sin\theta_{12} & 0 & 0 \\ \sin\theta_{12} & \cos\theta_{12} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{12} \\ 0 & 0 & 0 & 1 \end{bmatrix} \begin{bmatrix} 1 & 0 & 0 & a_{12} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{12} & -\sin\alpha_{12} & 0 \\ 0 & \sin\alpha_{12} & \cos\alpha_{12} & 0 \\ 0 & 0 & 0 & 1 \end{bmatrix}$$

$$A_{12} = \begin{bmatrix} \cos\theta_{12} & -\sin\theta_{12}\cos\alpha_{12} & \sin\theta_{12}\sin\alpha_{12} & a_{12}\cos\theta_{12} \\ \sin\theta_{12} & \cos\theta_{12}\cos\alpha_{12} & -\cos\theta_{12}\sin\alpha_{12} & a_{12}\sin\theta_{12} \\ 0 & \sin\alpha_{12} & \cos\alpha_{12} & d_{12} \\ 0 & 0 & 0 & 1 \end{bmatrix}$$

Joint 13 connects the Right foot, $4^{th}$ toe Proximal Phalange to the Right foot, $4^{th}$ toe Metatarsal. The $d_{13}$ link length of the $4^{th}$ Proximal Phalange runs collinear with the 4th Proximal Phalange centroid running from the $4^{th}$ Proximal Phalange base to the tip of the $4^{th}$ Metatarsal along the X axis.

$$A_{13} = \begin{bmatrix} \cos\theta_{13} & -\sin\theta_{13} & 0 & 0 \\ \sin\theta_{13} & \cos\theta_{13} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{13} \\ 0 & 0 & 0 & 1 \end{bmatrix} \begin{bmatrix} 1 & 0 & 0 & a_{13} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{13} & -\sin\alpha_{13} & 0 \\ 0 & \sin\alpha_{13} & \cos\alpha_{13} & 0 \\ 0 & 0 & 0 & 1 \end{bmatrix}$$

$$A_{13} = \begin{bmatrix} \cos\theta_{13} & -\sin\theta_{13}\cos\alpha_{13} & \sin\theta_{13}\sin\alpha_{13} & a_{13}\cos\theta_{13} \\ \sin\theta_{13} & \cos\theta_{13}\cos\alpha_{13} & -\cos\theta_{13}\sin\alpha_{13} & a_{13}\sin\theta_{13} \\ 0 & \sin\alpha_{13} & \cos\alpha_{13} & d_{13} \\ 0 & 0 & 0 & 1 \end{bmatrix}$$

Joint 14 connects the Right foot, $5^{th}$ toe Proximal Phalange to the Right foot, $5^{th}$ toe Metatarsal. The $d_{14}$ link length of the $5^{th}$ Proximal Phalange runs collinear with the $5^{th}$ Proximal Phalange centroid running from the $5^{th}$ Proximal Phalange base to the tip of the $5^{th}$ Metatarsal along the X axis.

$$A_{14} = \begin{bmatrix} \cos\theta_{14} & -\sin\theta_{14} & 0 & 0 \\ \sin\theta_{14} & \cos\theta_{14} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{14} \\ 0 & 0 & 0 & 1 \end{bmatrix} \begin{bmatrix} 1 & 0 & 0 & a_{14} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{14} & -\sin\alpha_{14} & 0 \\ 0 & \sin\alpha_{14} & \cos\alpha_{14} & 0 \\ 0 & 0 & 0 & 1 \end{bmatrix}$$

$$A_{14} = \begin{bmatrix} \cos\theta_{14} & -\sin\theta_{14}\cos\alpha_{14} & \sin\theta_{14}\sin\alpha_{14} & a_{14}\cos\theta_{14} \\ \sin\theta_{14} & \cos\theta_{14}\cos\alpha_{14} & -\cos\theta_{14}\sin\alpha_{14} & a_{14}\sin\theta_{14} \\ 0 & \sin\alpha_{14} & \cos\alpha_{14} & d_{14} \\ 0 & 0 & 0 & 1 \end{bmatrix}$$

Joint 15 connects the Right foot, $1^{st}$ toe Metatarsal to the Right foot, $2^{nd}$ toe Metatarsal. The $d_{15}$ link length of the Right big toe Metatarsal runs collinear with the $1^{st}$ Metatarsal centroid running from the $1^{st}$ Metatarsal to the $2^{nd}$ Metatarsal along the Y axis.

$$A_{15} = \begin{bmatrix} \cos\theta_{15} & -\sin\theta_{15} & 0 & 0 \\ \sin\theta_{15} & \cos\theta_{15} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{15} \\ 0 & 0 & 0 & 1 \end{bmatrix} \begin{bmatrix} 1 & 0 & 0 & a_{15} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{15} & -\sin\alpha_{15} & 0 \\ 0 & \sin\alpha_{15} & \cos\alpha_{15} & 0 \\ 0 & 0 & 0 & 1 \end{bmatrix}$$

$$A_{15} = \begin{bmatrix} \cos\theta_{15} & -\sin\theta_{15}\cos\alpha_{15} & \sin\theta_{15}\sin\alpha_{15} & a_{15}\cos\theta_{15} \\ \sin\theta_{15} & \cos\theta_{15}\cos\alpha_{15} & -\cos\theta_{15}\sin\alpha_{15} & a_{15}\sin\theta_{15} \\ 0 & \sin\alpha_{15} & \cos\alpha_{15} & d_{15} \\ 0 & 0 & 0 & 1 \end{bmatrix}$$

Joint 16 connects the Right foot, $2^{nd}$ toe Metatarsal to the Right foot $3^{rd}$ toe Metatarsal. The $d_{16}$ link length of the Right $2^{nd}$ Metatarsal runs collinear with the $2^{nd}$ Metatarsal centroid running from the $2^{nd}$ Metatarsal to the $3^{rd}$ Metatarsal along the Y axis. This is a touch joint of adjacent metatarsals.

$$A_{16} = \begin{bmatrix} \cos\theta_{16} & -\sin\theta_{16} & 0 & 0 \\ \sin\theta_{16} & \cos\theta_{16} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{16} \\ 0 & 0 & 0 & 1 \end{bmatrix} \begin{bmatrix} 1 & 0 & 0 & a_{16} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{16} & -\sin\alpha_{16} & 0 \\ 0 & \sin\alpha_{16} & \cos\alpha_{16} & 0 \\ 0 & 0 & 0 & 1 \end{bmatrix}$$

$$A_{16} = \begin{bmatrix} \cos\theta_{16} & -\sin\theta_{16}\cos\alpha_{16} & \sin\theta_{16}\sin\alpha_{16} & a_{16}\cos\theta_{16} \\ \sin\theta_{16} & \cos\theta_{16}\cos\alpha_{16} & -\cos\theta_{16}\sin\alpha_{16} & a_{16}\sin\theta_{16} \\ 0 & \sin\alpha_{16} & \cos\alpha_{16} & d_{16} \\ 0 & 0 & 0 & 1 \end{bmatrix}$$

Joint 17 connects the Right foot, $3^{rd}$ toe Metatarsal to the Right foot $4^{th}$ toe Metatarsal. The $d_{17}$ link length of the Right $4^{th}$ Metatarsal runs collinear with the $3^{rd}$ Metatarsal centroid running from the $3^{rd}$ Metatarsal to the $3^{rd}$ Metatarsal along the Y axis. This is a touch joint of adjacent metatarsals.

$$A_{17} = \begin{bmatrix} \cos\theta_{17} & -\sin\theta_{17} & 0 & 0 \\ \sin\theta_{17} & \cos\theta_{17} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{17} \\ 0 & 0 & 0 & 1 \end{bmatrix} \begin{bmatrix} 1 & 0 & 0 & a_{17} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{17} & -\sin\alpha_{17} & 0 \\ 0 & \sin\alpha_{17} & \cos\alpha_{17} & 0 \\ 0 & 0 & 0 & 1 \end{bmatrix}$$

$$A_{17} = \begin{bmatrix} \cos\theta_{17} & -\sin\theta_{17}\cos\alpha_{17} & \sin\theta_{17}\sin\alpha_{17} & a_{17}\cos\theta_{17} \\ \sin\theta_{17} & \cos\theta_{17}\cos\alpha_{17} & -\cos\theta_{17}\sin\alpha_{17} & a_{17}\sin\theta_{17} \\ 0 & \sin\alpha_{17} & \cos\alpha_{17} & d_{17} \\ 0 & 0 & 0 & 1 \end{bmatrix}$$

Joint 18 connects the Right foot, 4th toe Metatarsal to the Right foot, $5^{th}$ toe Metatarsal. The $d_{18}$ link length of the Right $4^{th}$ Metatarsal runs collinear with the 4th Metatarsal centroid running from the $4^{th}$ Metatarsal to the 4th Metatarsal along the Y axis. This is a touch joint of adjacent metatarsals.

$$A_{18} = \begin{bmatrix} \cos\theta_{18} & -\sin\theta_{18} & 0 & 0 \\ \sin\theta_{18} & \cos\theta_{18} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{18} \\ 0 & 0 & 0 & 1 \end{bmatrix} \begin{bmatrix} 1 & 0 & 0 & a_{18} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{18} & -\sin\alpha_{18} & 0 \\ 0 & \sin\alpha_{18} & \cos\alpha_{18} & 0 \\ 0 & 0 & 0 & 1 \end{bmatrix}$$

$$A_{18} = \begin{bmatrix} \cos\theta_{18} & -\sin\theta_{18}\cos\alpha_{18} & \sin\theta_{18}\sin\alpha_{18} & a_{18}\cos\theta_{18} \\ \sin\theta_{18} & \cos\theta_{18}\cos\alpha_{18} & -\cos\theta_{18}\sin\alpha_{18} & a_{18}\sin\theta_{18} \\ 0 & \sin\alpha_{18} & \cos\alpha_{18} & d_{18} \\ 0 & 0 & 0 & 1 \end{bmatrix}$$

Joint 19 connects the Right foot, $1^{st}$ toe Metatarsal to the Right foot medial cuneiform. The $d_{19}$ link length of the Right big toe Metatarsal runs collinear with the $1^{st}$ Proximal Phalange centroid running from the $1^{st}$ Proximal Phalange base to the tip of the $1^{st}$ Metatarsal along the X axis.

$$A_{19} = \begin{bmatrix} \cos\theta_{19} & -\sin\theta_{19} & 0 & 0 \\ \sin\theta_{19} & \cos\theta_{19} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{19} \\ 0 & 0 & 0 & 1 \end{bmatrix}$$

$$\begin{bmatrix} 1 & 0 & 0 & a_{19} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{19} & -\sin\alpha_{19} & 0 \\ 0 & \sin\alpha_{19} & \cos\alpha_{19} & 0 \\ 0 & 0 & 0 & 1 \end{bmatrix}$$

$$A_{19} = \begin{bmatrix} \cos\theta_{19} & -\sin\theta_{19}\cos\alpha_{19} & \sin\theta_{19}\sin\alpha_{19} & a_{19}\cos\theta_{19} \\ \sin\theta_{19} & \cos\theta_{19}\cos\alpha_{19} & -\cos\theta_{19}\sin\alpha_{19} & a_{19}\sin\theta_{19} \\ 0 & \sin\alpha_{19} & \cos\alpha_{19} & d_{19} \\ 0 & 0 & 0 & 1 \end{bmatrix}$$

Joint 20 connects the Right foot, $2^{nd}$ toe Metatarsal to Right foot, Medial Cuneiform. The $d_{20}$ link length of the right $2^{nd}$ toe metatarsal runs collinear with the $2^{nd}$ metatarsal centroid running from the $2^{nd}$ Metatarsal base to the tip of the Right Medial Cuneiform along the X axis.

$$A_{20} = \begin{bmatrix} \cos\theta_{20} & -\sin\theta_{20} & 0 & 0 \\ \sin\theta_{20} & \cos\theta_{20} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{20} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{20} & -\sin\alpha_{20} & 0 \\ 0 & \sin\alpha_{20} & \cos\alpha_{20} & 0 \\ 0 & 0 & 0 & 1 \end{bmatrix}$$

$$A_{20} = \begin{bmatrix} \cos\theta_{20} & -\sin\theta_{20}\cos\alpha_{20} & \sin\theta_{20}\sin\alpha_{20} & a_{20}\sin\theta_{20} \\ \sin\theta_{20} & \cos\theta_{20}\cos\alpha_{20} & -\cos\theta_{20}\sin\alpha_{20} & a_{20}\sin\theta_{20} \\ 0 & \sin\alpha_{20} & \cos\alpha_{20} & d_{20} \\ 0 & 0 & 0 & 1 \end{bmatrix}$$

Joint 21 connects the Right foot, $2^{nd}$ toe Metatarsal to the Right foot Intermediate cuneiform. The $d_{21}$ link length of the Right $2^{nd}$ toe Metatarsal runs collinear with the $2^{nd}$ Metatarsal centroid running from the $2^{nd}$ Metatarsal base to the tip of the Right Intermediate Cuneiform along the X axis $$A_{21} = \begin{bmatrix} \cos\theta_{21} & -\sin\theta_{21} & 0 & 0 \\ \sin\theta_{21} & \cos\theta_{21} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{21} \\ 0 & 0 & 0 & 1 \end{bmatrix}$$

$$\begin{bmatrix} 1 & 0 & 0 & a_{21} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{21} & -\sin\alpha_{21} & 0 \\ 0 & \sin\alpha_{21} & \cos\alpha_{21} & 0 \\ 0 & 0 & 0 & 1 \end{bmatrix}$$

$$A_{21} = \begin{bmatrix} \cos\theta_{21} & -\sin\theta_{21}\cos\alpha_{21} & \sin\theta_{21}\sin\alpha_{21} & a_{21}\cos\theta_{21} \\ \sin\theta_{21} & \cos\theta_{21}\cos\alpha_{21} & -\cos\theta_{21}\sin\alpha_{21} & a_{21}\sin\theta_{21} \\ 0 & \sin\alpha_{21} & \cos\alpha_{21} & d_{21} \\ 0 & 0 & 0 & 1 \end{bmatrix}$$

Joint 22 connects the Right foot, $2^{nd}$ toe Metatarsal to the Right foot Lateral Cuneiform. The $d_{22}$ link length of the Right $2^{nd}$ toe Metatarsal runs collinear with the $2^{nd}$ Metatarsal centroid running from the $2^{nd}$ Metatarsal base to the tip of the Right Lateral Cuneiform along the X axis $$A_{22} = \begin{bmatrix} \cos\theta_{22} & -\sin\theta_{22} & 0 & 0 \\ \sin\theta_{22} & \cos\theta_{22} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{22} \\ 0 & 0 & 0 & 1 \end{bmatrix}$$

$$\begin{bmatrix} 1 & 0 & 0 & a_{22} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{22} & -\sin\alpha_{22} & 0 \\ 0 & \sin\alpha_{22} & \cos\alpha_{22} & 0 \\ 0 & 0 & 0 & 1 \end{bmatrix}$$

$$A_{22} = \begin{bmatrix} \cos\theta_{22} & -\sin\theta_{22}\cos\alpha_{22} & \sin\theta_{22}\sin\alpha_{22} & a_{22}\cos\theta_{22} \\ \sin\theta_{22} & \cos\theta_{22}\cos\alpha_{22} & -\cos\theta_{22}\sin\alpha_{22} & a_{22}\sin\theta_{22} \\ 0 & \sin\alpha_{22} & \cos\alpha_{22} & d_{22} \\ 0 & 0 & 0 & 1 \end{bmatrix}$$

Joint 23 connects the Right foot, $3^{rd}$ toe Metatarsal to the Right fool Lateral Cuneiform. The $d_{23}$ link length of the Right $3^{rd}$ Metatarsal runs collinear with the 3rd Metatarsal centroid running from the $3^{rd}$ Metatarsal base to the tip of the Right Lateral Cuneiform along the X axis $$A_{23} = \begin{bmatrix} \cos\theta_{23} & -\sin\theta_{23} & 0 & 0 \\ \sin\theta_{23} & \cos\theta_{23} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{23} \\ 0 & 0 & 0 & 1 \end{bmatrix}$$

$$\begin{bmatrix} 1 & 0 & 0 & a_{23} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{23} & -\sin\alpha_{23} & 0 \\ 0 & \sin\alpha_{23} & \cos\alpha_{23} & 0 \\ 0 & 0 & 0 & 1 \end{bmatrix}$$

$$A_{23} = \begin{bmatrix} \cos\theta_{23} & -\sin\theta_{23}\cos\alpha_{23} & \sin\theta_{23}\sin\alpha_{23} & a_{23}\cos\theta_{23} \\ \sin\theta_{23} & \cos\theta_{23}\cos\alpha_{23} & -\cos\theta_{23}\sin\alpha_{23} & a_{23}\sin\theta_{23} \\ 0 & \sin\alpha_{23} & \cos\alpha_{23} & d_{23} \\ 0 & 0 & 0 & 1 \end{bmatrix}$$

Joint 24 connects the right foot, $4^{th}$ toe metatarsal to the Right foot Lateral Cuneiform. The $d_{24}$ link length of the Right $4^{th}$ Metatarsal runs collinear with the $4^{th}$ Metatarsal centroid running from the $4^{th}$ Metatarsal base to the tip of the Right Lateral Cuneiform along the X axis.

$$A_{24} = \begin{bmatrix} \cos\theta_{24} & -\sin\theta_{24} & 0 & 0 \\ \sin\theta_{24} & \cos\theta_{24} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{24} \\ 0 & 0 & 0 & 1 \end{bmatrix}$$

$$\begin{bmatrix} 1 & 0 & 0 & a_{1} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{24} & -\sin\alpha_{24} & 0 \\ 0 & \sin\alpha_{24} & \cos\alpha_{24} & 0 \\ 0 & 0 & 0 & 1 \end{bmatrix}$$

Joint 25 connects the Right foot, 4th toe Metatarsal to the Right foot cuboid bone. The $d_{25}$ link length of the Right $4^{th}$ Metatarsal runs collinear with the 4th Metatarsal centroid running from the $4^{th}$ Metatarsal base to the tip of the Right Cuboid along the X axis.

$$A_{25} = \begin{bmatrix} \cos\theta_{25} & -\sin\theta_{25} & 0 & 0 \\ \sin\theta_{25} & \cos\theta_{25} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{25} \\ 0 & 0 & 0 & 1 \end{bmatrix}$$

$$\begin{bmatrix} 1 & 0 & 0 & a_{25} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{25} & -\sin\alpha_{25} & 0 \\ 0 & \sin\alpha_{25} & \cos\alpha_{25} & 0 \\ 0 & 0 & 0 & 1 \end{bmatrix}$$

$$A_{25} = \begin{bmatrix} \cos\theta_{25} & -\sin\theta_{25}\cos\alpha_{25} & \sin\theta_{25}\sin\alpha_{25} & a_{25}\cos\theta_{25} \\ \sin\theta_{25} & \cos\theta_{25}\cos\alpha_{25} & -\cos\theta_{25}\sin\alpha_{25} & a_{25}\sin\theta_{25} \\ 0 & \sin\alpha_{25} & \cos\alpha_{25} & d_{25} \\ 0 & 0 & 0 & 1 \end{bmatrix}$$

Joint 26 connects the Right foot, 5th toe Metatarsal to the Right foot cuboid bone. The $d_{26}$ link length of the Right 5th Metatarsal runs collinear with the 5th Metatarsal centroid running from the $5^{th}$ Metatarsal base to the tip of the Right Cuboid along the X axis.

$$A_{26} = \begin{bmatrix} \cos\theta_{26} & -\sin\theta_{26} & 0 & 0 \\ \sin\theta_{26} & \cos\theta_{26} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{26} \\ 0 & 0 & 0 & 1 \end{bmatrix}$$

$$A_{26} = \begin{bmatrix} 1 & 0 & 0 & a_{26} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{26} & -\sin\alpha_{26} & 0 \\ 0 & \sin\alpha_{26} & \cos\alpha_{26} & 0 \\ 0 & 0 & 0 & 1 \end{bmatrix}$$

$$A_{26} = \begin{bmatrix} \cos\theta_{26} & -\sin\theta_{26}\cos\alpha_{26} & \sin\theta_{26}\sin\alpha_{26} & a_{26}\cos\theta_{26} \\ \sin\theta_{26} & \cos\theta_{26}\cos\alpha_{26} & -\cos\theta_{26}\sin\alpha_{26} & a_{26}\sin\theta_{26} \\ 0 & \sin\alpha_{26} & \cos\alpha_{26} & d_{26} \\ 0 & 0 & 0 & 1 \end{bmatrix}$$

Joint 27 connects the Right foot, Medial Cuneiform to the Right foot Intermediate Cuneiform. The $d_{27}$ link length of the Right Medial Cuneiform runs collinear with the Right Medial Cuneiform running from the Right Medial Cuneiform base to the tip of the Right Intermediate Cuneiform along the X axis.

$$A_{27} = \begin{bmatrix} \cos\theta_{27} & -\sin\theta_{27} & 0 & 0 \\ \sin\theta_{27} & \cos\theta_{27} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{27} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{27} & -\sin\alpha_{27} & 0 \\ 0 & \sin\alpha_{27} & \cos\alpha_{27} & 0 \\ 0 & 0 & 0 & 1 \end{bmatrix}$$

$$A_{27} = \begin{bmatrix} \cos\theta_{27} & -\sin\theta_{27}\cos\alpha_{27} & \sin\theta_{27}\sin\alpha_{27} & a_{27}\cos\theta_{27} \\ \sin\theta_{27} & \cos\theta_{27}\cos\alpha_{27} & -\cos\theta_{27}\sin\alpha_{27} & a_{27}\sin\theta_{27} \\ 0 & \sin\alpha_{27} & \cos\alpha_{27} & d_{27} \\ 0 & 0 & 0 & 1 \end{bmatrix}$$

Joint 28 connects the Right foot, Intermediate Cuneiform to the Right foot Lateral Cuneiform. The $d_{28}$ link length of the Right Intermediate Cuneiform runs collinear with Right Intermediate Cuneiform running from the Intermediate Cuneiform base to the tip of the Lateral Cuneiform along the X axis.

$$A_{28} = \begin{bmatrix} \cos\theta_{28} & -\sin\theta_{28} & 0 & 0 \\ \sin\theta_{28} & \cos\theta_{28} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{28} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{28} & -\sin\alpha_{28} & 0 \\ 0 & \sin\alpha_{28} & \cos\alpha_{28} & 0 \\ 0 & 0 & 0 & 1 \end{bmatrix}$$

$$A_{28} = \begin{bmatrix} \cos\theta_{28} & -\sin\theta_{28}\cos\alpha_{28} & \sin\theta_{28}\sin\alpha_{28} & a_{28}\cos\theta_{28} \\ \sin\theta_{28} & \cos\theta_{28}\cos\alpha_{28} & -\cos\theta_{28}\sin\alpha_{28} & a_{28}\sin\theta_{28} \\ 0 & \sin\alpha_{28} & \cos\alpha_{28} & d_{28} \\ 0 & 0 & 0 & 1 \end{bmatrix}$$

Joint 29 connects the Right foot, Lateral Cuneiform to the Right foot Cuboid. The $d_{29}$ link length of the Right Lateral Cuneiform runs collinear with the Right Lateral Cuneiform centroid running from the Lateral Cuneiform base to the tip of the Cuboid along the Y axis.

$$A_{29} = \begin{bmatrix} \cos\theta_{29} & -\sin\theta_{29} & 0 & 0 \\ \sin\theta_{29} & \cos\theta_{29} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{29} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{29} & -\sin\alpha_{29} & 0 \\ 0 & \sin\alpha_{29} & \cos\alpha_{29} & 0 \\ 0 & 0 & 0 & 1 \end{bmatrix}$$

$$A_{29} = \begin{bmatrix} \cos\theta_{29} & -\sin\theta_{29}\cos\alpha_{29} & \sin\theta_{29}\sin\alpha_{29} & a_{29}\cos\theta_{29} \\ \sin\theta_{29} & \cos\theta_{29}\cos\alpha_{29} & -\cos\theta_{29}\sin\alpha_{29} & a_{29}\sin\theta_{29} \\ 0 & \sin\alpha_{29} & \cos\alpha_{29} & d_{29} \\ 0 & 0 & 0 & 1 \end{bmatrix}$$

Joint 30 connects the Right foot, Medial Cuneiform bone to the Right foot Navicular bone. The $d_{30}$ link length of the Right Medial Cuneiform runs collinear with the Right Medial Cuneiform running from the Right Medial Cuneiform base to the tip of the Right Navicular along the X axis.

$$A_{30} = \begin{bmatrix} \cos\theta_{30} & -\sin\theta_{30} & 0 & 0 \\ \sin\theta_{30} & \cos\theta_{30} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{30} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{30} & -\sin\alpha_{30} & 0 \\ 0 & \sin\alpha_{30} & \cos\alpha_{30} & 0 \\ 0 & 0 & 0 & 1 \end{bmatrix}$$

$$A_{30} = \begin{bmatrix} \cos\theta_{30} & -\sin\theta_{30}\cos\alpha_{30} & \sin\theta_{30}\sin\alpha_{30} & a_{30}\cos\theta_{30} \\ \sin\theta_{30} & \cos\theta_{30}\cos\alpha_{30} & -\cos\theta_{30}\sin\alpha_{30} & a_{30}\sin\theta_{30} \\ 0 & \sin\alpha_{30} & \cos\alpha_{30} & d_{30} \\ 0 & 0 & 0 & 1 \end{bmatrix}$$

Joint 31 connects the Right foot, Intermediate Cuneiform bone to the Right foot navicular bone. This joint is both rotational of the Right Intermediate Cuneiform bone about the Right navicular. The $d_{31}$ link length of the Right Intermediate Cuneiform runs collinear with the Right medial Cuneiform running from the Intermediate Cuneiform to the tip of Navicular along the X axis.

$$A_{31} = \begin{bmatrix} \cos\theta_{31} & -\sin\theta_{31} & 0 & 0 \\ \sin\theta_{31} & \cos\theta_{31} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{31} \\ 0 & 0 & 0 & 1 \end{bmatrix}$$

$$\begin{bmatrix} 1 & 0 & 0 & a_{31} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{31} & -\sin\alpha_{31} & 0 \\ 0 & \sin\alpha_{31} & \cos\alpha_{31} & 0 \\ 0 & 0 & 0 & 1 \end{bmatrix}$$

$$A_{31} = \begin{bmatrix} \cos\theta_{31} & -\sin\theta_{31}\cos\alpha_{31} & \sin\theta_{31}\sin\alpha_{31} & a_{31}\cos\theta_{31} \\ \sin\theta_{31} & \cos\theta_{31}\cos\alpha_{31} & -\cos\theta_{31}\sin\alpha_{31} & a_{31}\sin\theta_{31} \\ 0 & \sin\alpha_{31} & \cos\alpha_{31} & d_{31} \\ 0 & 0 & 0 & 1 \end{bmatrix}$$

Joint 32 connects the Right foot, Lateral Cuneiform bone to the Right foot Navicular bone. This joint is both rotational of the Right Lateral Cuneiform bone about the Right Navicular in the X plane, and rotation of the Right Lateral Cuneiform bone about the Right Navicular in the Y plane, in an oblong interface supporting rotational motion in two direction. There is no linear motion in either the X plane or the Y plane in this joint.

$$A_{32} = \begin{bmatrix} \cos\theta_{32} & -\sin\theta_{32} & 0 & 0 \\ \sin\theta_{32} & \cos\theta_{32} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{32} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{32} & -\sin\alpha_{32} & 0 \\ 0 & \sin\alpha_{32} & \cos\alpha_{32} & 0 \\ 0 & 0 & 0 & 1 \end{bmatrix}$$

$$A_{32} = \begin{bmatrix} \cos\theta_{32} & -\sin\theta_{32}\cos\alpha_{32} & \sin\theta_{32}\sin\alpha_{32} & a_{32}\cos\theta_{32} \\ \sin\theta_{32} & \cos\theta_{32}\cos\alpha_{32} & -\cos\theta_{32}\sin\alpha_{32} & a_{32}\sin\theta_{32} \\ 0 & \sin\alpha_{32} & \cos\alpha_{32} & d_{32} \\ 0 & 0 & 0 & 1 \end{bmatrix}$$

Joint 33 connects the right foot, Navicular Cuneiform to the Right foot Cuboid. The $d_{33}$ link length of the right Navicular runs collinear with the Navicular centroid running from the Navicular to the Cuboid along the Y axis.

$$A_{33} = \begin{bmatrix} \cos\theta_{33} & -\sin\theta_{33} & 0 & 0 \\ \sin\theta_{33} & \cos\theta_{33} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{33} \\ 0 & 0 & 0 & 1 \end{bmatrix}$$

$$\begin{bmatrix} 1 & 0 & 0 & a_1 \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{33} & -\sin\alpha_{33} & 0 \\ 0 & \sin\alpha_{33} & \cos\alpha_{33} & 0 \\ 0 & 0 & 0 & 1 \end{bmatrix}$$

$$A_{33} = \begin{bmatrix} \cos\theta_{33} & -\sin\theta_{33}\cos\alpha_{33} & \sin\theta_{33}\sin\alpha_{33} & a_{33}\cos\theta_{33} \\ \sin\theta_{33} & \cos\theta_{33}\cos\alpha_{33} & -\cos\theta_{33}\sin\alpha_{33} & a_{33}\sin\theta_{33} \\ 0 & \sin\alpha_{33} & \cos\alpha_{33} & d_{33} \\ 0 & 0 & 0 & 1 \end{bmatrix}$$

Joint 34 connects the Right foot, Navicular bone to the Right foot Talus bone. This joint is a rotational joint with respect to the Navicular bone and the Talus bone in the Z plane, and it is also a rotational joint with respect to the Navicular bone and the Talus bone in the Y plane. There is no linear lateral motion in this joint, rather, the curved structure of the Talus-Navicular interface is curved, thus supporting only rotation.

$$A_{34} = \begin{bmatrix} \cos\theta_{34} & -\sin\theta_{34} & 0 & 0 \\ \sin\theta_{34} & \cos\theta_{34} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{34} & 1 \end{bmatrix} \begin{bmatrix} 1 & 0 & 0 & a_{34} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{34} & -\sin\alpha_{34} & 0 \\ 0 & \sin\alpha_{34} & \cos\alpha_{34} & 0 \\ 0 & 0 & 0 & 1 \end{bmatrix}$$

$$A_{34} = \begin{bmatrix} \cos\theta_{34} & -\sin\theta_{34}\cos\alpha_{34} & \sin\theta_{34}\sin\alpha_{34} & a_{34}\cos\theta_{34} \\ \sin\theta_{34} & \cos\theta_{34}\cos\alpha_{34} & -\cos\theta_{34}\sin\alpha_{34} & a_{34}\sin\theta_{34} \\ 0 & \sin\alpha_{34} & \cos\alpha_{34} & d_{34} \\ 0 & 0 & 0 & 1 \end{bmatrix}$$

Joint 35 connects the right foot, Cuboid to the Right foot Calcaneus. The $d_{35}$ link length of the Right Calcaneus runs collinear with the Right Cuboid running from the Cuboid base to the tip of the Calcaneus along the X axis.

$$A_{35} = \begin{bmatrix} \cos\theta_{35} & -\sin\theta_{35} & 0 & 0 \\ \sin\theta_{35} & \cos\theta_{35} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{35} \\ 0 & 0 & 0 & 1 \end{bmatrix} \begin{bmatrix} 1 & 0 & 0 & a_1 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{35} & -\sin\alpha_{35} & 0 \\ 0 & \sin\alpha_{35} & \cos\alpha_{35} & 0 \\ 0 & 0 & 0 & 1 \end{bmatrix}$$

$$A_{35} = \begin{bmatrix} \cos\theta_{35} & -\sin\theta_{35}\cos\alpha_{35} & \sin\theta_{35}\sin\alpha_{35} & a_{35}\cos\theta_{35} \\ \sin\theta_{35} & \cos\theta_{35}\cos\alpha_{35} & -\cos\theta_{35}\sin\alpha_{35} & a_{35}\sin\theta_{35} \\ 0 & \sin\alpha_{35} & \cos\alpha_{35} & d_{35} \\ 0 & 0 & 0 & 1 \end{bmatrix}$$

Joint 36 connects the right foot, Talus to the right foot Calcaneus. The $d_{36}$ link length of the right Talus runs collinear with the right Talus running from the Talus to the Calcaneus along the X axis.

$$A_{36} = \begin{bmatrix} \cos\theta_{36} & -\sin\theta_{36} & 0 & 0 \\ \sin\theta_{36} & \cos\theta_{36} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{36} \\ 0 & 0 & 0 & 1 \end{bmatrix} \begin{bmatrix} 1 & 0 & 0 & a_1 \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{36} & -\sin\alpha_{36} & 0 \\ 0 & \sin\alpha_{36} & \cos\alpha_{36} & 0 \\ 0 & 0 & 0 & 1 \end{bmatrix}$$

$$A_{36} = \begin{bmatrix} \cos\theta_{36} & -\sin\theta_{36}\cos\alpha_{36} & \sin\theta_{36}\sin\alpha_{36} & a_{36}\cos\theta_{36} \\ \sin\theta_{36} & \cos\theta_{36}\cos\alpha_{36} & -\cos\theta_{36}\sin\alpha_{36} & a_{36}\sin\theta_{36} \\ 0 & \sin\alpha_{36} & \cos\alpha_{36} & d_{36} \\ 0 & 0 & 0 & 1 \end{bmatrix}$$

Joint 37 connects the Right fibula to the Right Talus bone, this is commonly referred to as the ankle joint. The $d_{37}$ link length of the Right Fibula runs collinear with the right Fibula running from the Fibula base to the Talus along the X axis.

$$A_{37} = \begin{bmatrix} \cos\theta_{37} & -\sin\theta_{37} & 0 & 0 \\ \sin\theta_{37} & \cos\theta_{37} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{37} & 1 \end{bmatrix} \begin{bmatrix} 1 & 0 & 0 & a_{37} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{37} & -\sin\alpha_{37} & 0 \\ 0 & \sin\alpha_{37} & \cos\alpha_{37} & 0 \\ 0 & 0 & 0 & 1 \end{bmatrix}$$

-continued $$A_{37} = \begin{bmatrix} \cos\theta_{37} & -\sin\theta_{37}\cos\alpha_{37} & \sin\theta_{37}\sin\alpha_{37} & a_{37}\cos\theta_{37} \\ \sin\theta_{37} & \cos\theta_{37}\cos\alpha_{37} & -\cos\theta_{37}\sin\alpha_{37} & a_{37}\sin\theta_{37} \\ 0 & \sin\alpha_{37} & \cos\alpha_{37} & d_{37} \\ 0 & 0 & 0 & 1 \end{bmatrix}$$

Joint 38 connects the Right tibia to the Right Talus bone. The $d_{38}$ link length of the Right Tibia runs collinear with the Right Tibia running from the Right Tibia base to the tip of the Right Talus along the X axis.

$$A_{38} = \begin{bmatrix} \cos\theta_{38} & -\sin\theta_{38} & 0 & 0 \\ \sin\theta_{38} & \cos\theta_{38} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{38} & 1 \end{bmatrix} \begin{bmatrix} 1 & 0 & 0 & a_{38} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{38} & -\sin\alpha_{38} & 0 \\ 0 & \sin\alpha_{38} & \cos\alpha_{38} & 0 \\ 0 & 0 & 0 & 1 \end{bmatrix}$$

$$A_{38} = \begin{bmatrix} \cos\theta_{38} & -\sin\theta_{38}\cos\alpha_{38} & \sin\theta_{38}\sin\alpha_{38} & a_{38}\cos\theta_{38} \\ \sin\theta_{38} & \cos\theta_{38}\cos\alpha_{38} & -\cos\theta_{38}\sin\alpha_{38} & a_{38}\sin\theta_{38} \\ 0 & \sin\alpha_{38} & \cos\alpha_{38} & d_{38} \\ 0 & 0 & 0 & 1 \end{bmatrix}$$

Joint 39 connects the Dorsal end of the Right Tibia to the dorsal end of the Right Fibula to form the Right Dorsal Tibiofibular joint. The $d_{39}$ link length of the Right Dorsal Tibia runs collinear with the Right Dorsal Tibia running from the Dorsal Tibia to the Right Dorsal Fibula along the Y axis.

$$A_{39} = \begin{bmatrix} \cos\theta_{39} & -\sin\theta_{39} & 0 & 0 \\ \sin\theta_{39} & \cos\theta_{39} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{39} & 1 \end{bmatrix} \begin{bmatrix} 1 & 0 & 0 & a_{39} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{39} & -\sin\alpha_{39} & 0 \\ 0 & \sin\alpha_{39} & \cos\alpha_{39} & 0 \\ 0 & 0 & 0 & 1 \end{bmatrix}$$

$$A_{37} = \begin{bmatrix} \cos\theta_{37} & -\sin\theta_{37}\cos\alpha_{37} & \sin\theta_{37}\sin\alpha_{37} & a_{37}\cos\theta_{37} \\ \sin\theta_{37} & \cos\theta_{37}\cos\alpha_{37} & -\cos\theta_{37}\sin\alpha_{37} & a_{37}\sin\theta_{37} \\ 0 & \sin\alpha_{37} & \cos\alpha_{37} & d_{37} \\ 0 & 0 & 0 & 1 \end{bmatrix}$$

Joint 40 connects the Proximal end of the Right Tibia to the Proximal end of the Right Fibula to form the Proximal Tibiofibular joint. The $d_{40}$ link length of the Right Proximal Tibia runs collinear with the Right Proximal Tibia running from the Proximal Tibia to the Right Proximal Fibula along the Y axis.

$$A_{40} = \begin{bmatrix} \cos\theta_{40} & -\sin\theta_{40} & 0 & 0 \\ \sin\theta_{40} & \cos\theta_{40} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{40} \\ 0 & 0 & 0 & 1 \end{bmatrix} \begin{bmatrix} 1 & 0 & 0 & a_{40} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{40} & -\sin\alpha_{40} & 0 \\ 0 & \sin\alpha_{40} & \cos\alpha_{40} & 0 \\ 0 & 0 & 0 & 1 \end{bmatrix}$$

$$A_{40} = \begin{bmatrix} \cos\theta_{40} & -\sin\theta_{40}\cos\alpha_{40} & \sin\theta_{40}\sin\alpha_{40} & a_{40}\cos\theta_{40} \\ \sin\theta_{40} & \cos\theta_{40}\cos\alpha_{40} & -\cos\theta_{40}\sin\alpha_{40} & a_{40}\sin\theta_{40} \\ 0 & \sin\alpha_{40} & \cos\alpha_{40} & d_{40} \\ 0 & 0 & 0 & 1 \end{bmatrix}$$

Joint 41 connects the Proximal end of the Tibia with the Distal end of the Femur to create the Right Femorotibial joint. Normal range of motion (ROM) at the knee is considered to be zero (0) degrees of extension (completely straight knee joint) to 135 degrees of flexion (fully bent knee joint). The knee joint is one of the strongest and most important joints in the human body. It enables the lower leg to move relative to the femur while supporting the body's weight. Movements at the knee joint are essential to walking, running, sitting and standing.

The knee is a synovial hinge joint formed between three bones: The Femur, Tibia, and Patella. Two rounded, convex processes (known as condyles) on the Distal end of the Femur meet two rounded, concave condyles at the Proximal end of the Tibia. A special characteristic of the knee that differentiates it from other hinge joints is that it allows a small degree of medial and lateral rotation when it is moderately flexed.

$$A_{41} = \begin{bmatrix} \cos\theta_{41} & -\sin\theta_{41} & 0 & 0 \\ \sin\theta_{41} & \cos\theta_{41} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{41} & 1 \end{bmatrix} \begin{bmatrix} 1 & 0 & 0 & a_{41} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{41} & -\sin\alpha_{41} & 0 \\ 0 & \sin\alpha_{41} & \cos\alpha_{41} & 0 \\ 0 & 0 & 0 & 1 \end{bmatrix}$$

$$A_{41} = \begin{bmatrix} \cos\theta_{41} & -\sin\theta_{41}\cos\alpha_{41} & \sin\theta_{41}\sin\alpha_{41} & a_{41}\cos\theta_{41} \\ \sin\theta_{41} & \cos\theta_{41}\cos\alpha_{41} & -\cos\theta_{41}\sin\alpha_{41} & a_{41}\sin\theta_{41} \\ 0 & \sin\alpha_{41} & \cos\alpha_{41} & d_{41} \\ 0 & 0 & 0 & 1 \end{bmatrix}$$

Joint 42 connects the Right femur Proximal end to the Right pelvis socket, forming the Right hip joint.

$$A_{42} = \begin{bmatrix} \cos\varphi_{42} & -\sin\varphi_{42} & 0 & 0 \\ \sin\varphi_{42} & \cos\varphi_{42} & 0 & 0 \\ 0 & 0 & 1 & 0 \\ 0 & 0 & 0 & 1 \end{bmatrix} \begin{bmatrix} \cos\theta_{42} & 0 & \sin\theta_{42} & 0 \\ 0 & 1 & 0 & 0 \\ -\sin\theta_{42} & 0 & \cos\theta_{42} & 0 \\ 0 & 0 & 0 & 1 \end{bmatrix}$$

$$\begin{bmatrix} 1 & 0 & 0 & 0 \\ 0 & \cos\psi_{42} & -\sin\varphi_{42} & 0 \\ 0 & \sin\varphi_{42} & \cos\varphi_{42} & 0 \\ 0 & 0 & 0 & 1 \end{bmatrix}$$

$$A_{42} = \begin{bmatrix} \cos\theta_{42} & -\sin\theta_{42}\cos\alpha_{42} & \sin\theta_{42}\sin\alpha_{42} & a_{42}\cos\theta_{42} \\ \sin\theta_{42} & \cos\theta_{42}\cos\alpha_{42} & -\cos\theta_{42}\sin\alpha_{42} & a_{42}\sin\theta_{42} \\ 0 & \sin\alpha_{42} & \cos\alpha_{42} & d_{42} \\ 0 & 0 & 0 & 1 \end{bmatrix}$$

Joint 43 connects the Left Foot, 1$^{st}$ Toe, Hallux, Distal Phalange to the Left Foot, 1$^{st}$ Toe, Proximal Phalange. The $d_{43}$ link length of the Hallux Distal Phalange runs collinear with the Hallux centroid running from the Hallux base to the tip of the 1$^{st}$ Proximal Phalange along the X axis.

$$A_{43} = \begin{bmatrix} \cos\theta_{43} & -\sin\theta_{43} & 0 & 0 \\ \sin\theta_{43} & \cos\theta_{43} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{43} \\ 0 & 0 & 0 & 1 \end{bmatrix} \begin{bmatrix} 1 & 0 & 0 & a_{43} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{43} & -\sin\alpha_{43} & 0 \\ 0 & \sin\alpha_{43} & \cos\alpha_{43} & 0 \\ 0 & 0 & 0 & 1 \end{bmatrix}$$

$$A_{43} = \begin{bmatrix} \cos\theta_{43} & -\sin\theta_{43}\cos\alpha_{43} & \sin\theta_{43}\sin\alpha_{43} & a_{43}\cos\theta_{43} \\ \sin\theta_{43} & \cos\theta_{43}\cos\alpha_{43} & -\cos\theta_{43}\sin\alpha_{43} & a_{43}\sin\theta_{43} \\ 0 & \sin\alpha_{43} & \cos\alpha_{43} & d_{43} \\ 0 & 0 & 0 & 1 \end{bmatrix}$$

Joint 44 connects the Left Foot, $2^{nd}$ Toe, Distal Phalange to the Left Foot $2^{nd}$ toe Middle Phalange. The $d_{44}$ link length of the $2^{nd}$ Distal Phalange runs collinear with the Distal Phalange centroid running from the $2^{nd}$ Distal Phalange base to the tip of the $2^{nd}$ Middle Phalange along the X axis.

$$A_{44} = \begin{bmatrix} \cos\theta_{44} & -\sin\theta_{44} & 0 & 0 \\ \sin\theta_{44} & \cos\theta_{44} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{44} \\ 0 & 0 & 0 & 1 \end{bmatrix} \begin{bmatrix} 1 & 0 & 0 & a_{44} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{44} & -\sin\alpha_{44} & 0 \\ 0 & \sin\alpha_{44} & \cos\alpha_{44} & 0 \\ 0 & 0 & 0 & 1 \end{bmatrix}$$

Joint 45 connects the Left foot, $3^{rd}$ toe, Distal Phalange to the Left foot, $3^{rd}$ toe Middle Phalange. The $d_{45}$ link length of the $3^{rd}$ Distal Phalange runs collinear with the $3^{rd}$ Distal Phalange centroid running from the $3^{rd}$ Distal Phalange base to the tip of the $3^{rd}$ Middle Phalange along the X axis.

$$A_{45} = \begin{bmatrix} \cos\theta_{45} & -\sin\theta_{45} & 0 & 0 \\ \sin\theta_{45} & \cos\theta_{45} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{45} \\ 0 & 0 & 0 & 1 \end{bmatrix} \begin{bmatrix} 1 & 0 & 0 & a_{45} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{45} & -\sin\alpha_{45} & 0 \\ 0 & \sin\alpha_{45} & \cos\alpha_{45} & 0 \\ 0 & 0 & 0 & 1 \end{bmatrix}$$

$$A_{45} = \begin{bmatrix} \cos\theta_{45} & -\sin\theta_{45}\cos\alpha_{45} & \sin\theta_{45}\sin\alpha_{45} & a_{45}\cos\theta_{45} \\ \sin\theta_{45} & \cos\theta_{45}\cos\alpha_{45} & -\cos\theta_{45}\sin\alpha_{45} & a_{45}\sin\theta_{45} \\ 0 & \sin\alpha_{45} & \cos\alpha_{45} & d_{45} \\ 0 & 0 & 0 & 1 \end{bmatrix}$$

Joint 46 connects the Left foot, $4^{th}$ toe, Distal Phalange to the Left foot, $4^{th}$ toe, Middle Phalange. The $d_{46}$ link length of the $4^{th}$ Distal Phalange runs collinear with the $4^{th}$ Distal Phalange centroid running from the $4^{th}$ Distal Phalange base to the tip of the $4^{th}$ Middle Phalange along the X axis.

$$A_{46} = \begin{bmatrix} \cos\theta_{46} & -\sin\theta_{46} & 0 & 0 \\ \sin\theta_{46} & \cos\theta_{46} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{46} \\ 0 & 0 & 0 & 1 \end{bmatrix} \begin{bmatrix} 1 & 0 & 0 & a_{46} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{46} & -\sin\alpha_{46} & 0 \\ 0 & \sin\alpha_{46} & \cos\alpha_{46} & 0 \\ 0 & 0 & 0 & 1 \end{bmatrix}$$

$$A_{46} = \begin{bmatrix} \cos\theta_{46} & -\sin\theta_{46}\cos\alpha_{46} & \sin\theta_{46}\sin\alpha_{46} & a_{46}\cos\theta_{46} \\ \sin\theta_{46} & \cos\theta_{46}\cos\alpha_{46} & -\cos\theta_{46}\sin\alpha_{46} & a_{46}\sin\theta_{46} \\ 0 & \sin\alpha_{46} & \cos\alpha_{46} & d_{46} \\ 0 & 0 & 0 & 1 \end{bmatrix}$$

Joint 47 connects the Left foot, $5^{th}$ toe, Distal Phalange to the Left foot, $5^{th}$ toe, Middle Phalange. The $d_{47}$ link length of the $5^{th}$ Distal Phalange runs collinear with the $4^{th}$ Distal Phalange centroid running from the $5^{th}$ Distal Phalange base to the tip of the $5^{th}$ Middle Phalange along the X axis.

$$A_{47} = \begin{bmatrix} \cos\theta_{47} & -\sin\theta_{47} & 0 & 0 \\ \sin\theta_{47} & \cos\theta_{47} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{47} \\ 0 & 0 & 0 & 1 \end{bmatrix} \begin{bmatrix} 1 & 0 & 0 & a_{47} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{47} & -\sin\alpha_{47} & 0 \\ 0 & \sin\alpha_{47} & \cos\alpha_{47} & 0 \\ 0 & 0 & 0 & 1 \end{bmatrix}$$

$$A_{47} = \begin{bmatrix} \cos\theta_{47} & -\sin\theta_{47}\cos\alpha_{47} & \sin\theta_{47}\sin\alpha_{47} & a_{47}\cos\theta_{47} \\ \sin\theta_{47} & \cos\theta_{47}\cos\alpha_{47} & -\cos\theta_{47}\sin\alpha_{47} & a_{47}\sin\theta_{47} \\ 0 & \sin\alpha_{47} & \cos\alpha_{47} & d_{47} \\ 0 & 0 & 0 & 1 \end{bmatrix}$$

Joint 48 connects the Left foot, $2^{nd}$ toe, Middle Phalange to the Left foot, $2^{nd}$ toe, Proximal Phalange. The $d_{48}$ link length of the $2^{nd}$ Middle Phalange runs collinear with the $2^{nd}$ Proximal Phalange centroid running from the $2^{nd}$ Middle Phalange base to the tip of the $2^{nd}$ Proximal Phalange along the X axis.

$$A_{48} = \begin{bmatrix} \cos\theta_{48} & -\sin\theta_{48} & 0 & 0 \\ \sin\theta_{48} & \cos\theta_{48} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{48} \\ 0 & 0 & 0 & 1 \end{bmatrix} \begin{bmatrix} 1 & 0 & 0 & a_{48} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{48} & -\sin\alpha_{48} & 0 \\ 0 & \sin\alpha_{48} & \cos\alpha_{48} & 0 \\ 0 & 0 & 0 & 1 \end{bmatrix}$$

$$A_{48} = \begin{bmatrix} \cos\theta_{48} & -\sin\theta_{48}\cos\alpha_{48} & \sin\theta_{48}\sin\alpha_{48} & a_{48}\cos\theta_{48} \\ \sin\theta_{48} & \cos\theta_{48}\cos\alpha_{48} & -\cos\theta_{48}\sin\alpha_{48} & a_{48}\sin\theta_{48} \\ 0 & \sin\alpha_{48} & \cos\alpha_{48} & d_{48} \\ 0 & 0 & 0 & 1 \end{bmatrix}$$

Joint 49 connects the Left foot, $3^{rd}$ toe, Middle Phalange to the Left foot, $3^{rd}$ toe, Proximal Phalange. The $d_{49}$ link length of the $3^{rd}$ Middle Phalange runs collinear with the $3^{rd}$ Middle Phalange centroid running from the $3^{rd}$ Middle Phalange base to the tip of the $3^{rd}$ Proximal Phalange along the X axis.

$$A_{49} = \begin{bmatrix} \cos\theta_{49} & -\sin\theta_{49} & 0 & 0 \\ \sin\theta_{49} & \cos\theta_{49} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{49} \\ 0 & 0 & 0 & 1 \end{bmatrix} \begin{bmatrix} 1 & 0 & 0 & a_{49} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{49} & -\sin\alpha_{49} & 0 \\ 0 & \sin\alpha_{49} & \cos\alpha_{49} & 0 \\ 0 & 0 & 0 & 1 \end{bmatrix}$$

$$A_{49} = \begin{bmatrix} \cos\theta_{49} & -\sin\theta_{49}\cos\alpha_{49} & \sin\theta_{49}\sin\alpha_{49} & a_{49}\cos\theta_{49} \\ \sin\theta_{49} & \cos\theta_{49}\cos\alpha_{49} & -\cos\theta_{49}\sin\alpha_{49} & a_{49}\sin\theta_{49} \\ 0 & \sin\alpha_{49} & \cos\alpha_{49} & d_{49} \\ 0 & 0 & 0 & 1 \end{bmatrix}$$

Joint 50 connects the Left foot, $4^{th}$ toe, Middle Phalange to the Left foot, $4^{th}$ toe, Proximal Phalange. The $d_8$ link length of the $4^{th}$ Middle Phalange runs collinear with the $4^{th}$ Middle Phalange centroid running from the $4^{th}$ Middle Phalange base to the tip of the $4^{th}$ Proximal Phalange along the X axis.

$$A_{50} = \begin{bmatrix} \cos\theta_{50} & -\sin\theta_{50} & 0 & 0 \\ \sin\theta_{50} & \cos\theta_{50} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{50} \\ 0 & 0 & 0 & 1 \end{bmatrix} \begin{bmatrix} 1 & 0 & 0 & a_{50} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{50} & -\sin\alpha_{50} & 0 \\ 0 & \sin\alpha_{50} & \cos\alpha_{50} & 0 \\ 0 & 0 & 0 & 1 \end{bmatrix}$$

$$A_{50} = \begin{bmatrix} \cos\theta_{50} & -\sin\theta_{50}\cos\alpha_{50} & \sin\theta_{50}\sin\alpha_{50} & a_{50}\cos\theta_{50} \\ \sin\theta_{50} & \cos\theta_{50}\cos\alpha_{50} & -\cos\theta_{43}\sin\alpha_{50} & a_{50}\sin\theta_{50} \\ 0 & \sin\alpha_{50} & \cos\alpha_{50} & d_{50} \\ 0 & 0 & 0 & 1 \end{bmatrix}$$

Joint 51 connects the Left foot, $5^{th}$ toe, Middle Phalange to the Left foot, $5^{th}$ toe Proximal Phalange. The $d_{51}$ link length of the $5^{th}$ Middle Phalange runs collinear with the $5^{th}$ Proximal Phalange centroid running from the $5^{th}$ Middle Phalange base to the tip of the $5^{th}$ Proximal Phalange along the X axis.

$$A_{51} = \begin{bmatrix} \cos\theta_{51} & -\sin\theta_{51} & 0 & 0 \\ \sin\theta_{51} & \cos\theta_{51} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{51} \\ 0 & 0 & 0 & 1 \end{bmatrix} \begin{bmatrix} 1 & 0 & 0 & a_{51} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{51} & -\sin\alpha_{51} & 0 \\ 0 & \sin\alpha_{51} & \cos\alpha_{51} & 0 \\ 0 & 0 & 0 & 1 \end{bmatrix}$$

$$A_{51} = \begin{bmatrix} \cos\theta_{51} & -\sin\theta_{51}\cos\alpha_{51} & \sin\theta_{51}\sin\alpha_{51} & a_{51}\cos\theta_{51} \\ \sin\theta_{51} & \cos\theta_{51}\cos\alpha_{51} & -\cos\theta_{51}\sin\alpha_{51} & a_{51}\sin\theta_{51} \\ 0 & \sin\alpha_{51} & \cos\alpha_{51} & d_{51} \\ 0 & 0 & 0 & 1 \end{bmatrix}$$

Joint 52 connects the Left foot $1^{st}$ toe Proximal Phalange to the Left foot, $1^{st}$ toe Metatarsal. The $d_{52}$ link length of the $1^{st}$ Proximal Phalange runs collinear with the $1^{st}$ Proximal Phalange centroid running from the $1^{st}$ Proximal Phalange base to the tip of the $1^{st}$ Metatarsal along the X axis.

$$A_{52} = \begin{bmatrix} \cos\theta_{52} & -\sin\theta_{52} & 0 & 0 \\ \sin\theta_{52} & \cos\theta_{52} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{52} \\ 0 & 0 & 0 & 1 \end{bmatrix} \begin{bmatrix} 1 & 0 & 0 & a_{52} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{52} & -\sin\alpha_{52} & 0 \\ 0 & \sin\alpha_{52} & \cos\alpha_{52} & 0 \\ 0 & 0 & 0 & 1 \end{bmatrix}$$

$$A_{52} = \begin{bmatrix} \cos\theta_{52} & -\sin\theta_{52}\cos\alpha_{52} & \sin\theta_{52}\sin\alpha_{52} & a_{52}\cos\theta_{52} \\ \sin\theta_{52} & \cos\theta_{52}\cos\alpha_{52} & -\cos\theta_{52}\sin\alpha_{52} & a_{52}\sin\theta_{52} \\ 0 & \sin\alpha_{52} & \cos\alpha_{52} & d_{52} \\ 0 & 0 & 0 & 1 \end{bmatrix}$$

Joint 53 connects the Left foot, $2^{nd}$ toe, Proximal Phalange to the Left foot, $2^{nd}$ toe Metatarsal. The $d_{53}$ link length of the $2^{nd}$ Proximal Phalange runs collinear with the $2^{nd}$ Proximal Phalange centroid running from the $2^{nd}$ Proximal Phalange base to the tip of the $2^{nd}$ Metatarsal along the X axis.

$$A_{53} = \begin{bmatrix} \cos\theta_{53} & -\sin\theta_{53} & 0 & 0 \\ \sin\theta_{53} & \cos\theta_{53} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{53} \\ 0 & 0 & 0 & 1 \end{bmatrix} \begin{bmatrix} 1 & 0 & 0 & a_{53} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{53} & -\sin\alpha_{53} & 0 \\ 0 & \sin\alpha_{53} & \cos\alpha_{53} & 0 \\ 0 & 0 & 0 & 1 \end{bmatrix}$$

$$A_{53} = \begin{bmatrix} \cos\theta_{53} & -\sin\theta_{53}\cos\alpha_{53} & \sin\theta_{53}\sin\alpha_{53} & a_{53}\cos\theta_{53} \\ \sin\theta_{53} & \cos\theta_{53}\cos\alpha_{53} & -\cos\theta_{53}\sin\alpha_{53} & a_{53}\sin\theta_{53} \\ 0 & \sin\alpha_{53} & \cos\alpha_{53} & d_{53} \\ 0 & 0 & 0 & 1 \end{bmatrix}$$

Joint 54 connects the Left foot, $3^{rd}$ toe, Proximal Phalange to the Left foot, $3^{rd}$ toe Metatarsal. The $d_{54}$ link length of the $3^{rd}$ Proximal Phalange runs collinear with the $3^{rd}$ Proximal Phalange centroid running from the $3^{rd}$ Proximal Phalange base to the tip of the $3^{rd}$ Metatarsal along the X axis.

$$A_{54} = \begin{bmatrix} \cos\theta_{54} & -\sin\theta_{54} & 0 & 0 \\ \sin\theta_{54} & \cos\theta_{54} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{54} \\ 0 & 0 & 0 & 1 \end{bmatrix} \begin{bmatrix} 1 & 0 & 0 & a_{54} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{54} & -\sin\alpha_{54} & 0 \\ 0 & \sin\alpha_{54} & \cos\alpha_{54} & 0 \\ 0 & 0 & 0 & 1 \end{bmatrix}$$

$$A_{54} = \begin{bmatrix} \cos\theta_{54} & -\sin\theta_{54}\cos\alpha_{54} & \sin\theta_{54}\sin\alpha_{54} & a_{54}\cos\theta_{54} \\ \sin\theta_{54} & \cos\theta_{54}\cos\alpha_{54} & -\cos\theta_{54}\sin\alpha_{54} & a_{54}\sin\theta_{54} \\ 0 & \sin\alpha_{54} & \cos\alpha_{54} & d_{54} \\ 0 & 0 & 0 & 1 \end{bmatrix}$$

Joint 55 connects the Left foot, $4^{th}$ toe Proximal Phalange to the Left foot $4^{th}$ toe Metatarsal. The $d_{55}$ link length of the $4^{th}$ Proximal Phalange runs collinear with the $4^{th}$ Proximal Phalange centroid running from the $4^{th}$ Proximal Phalange base to the tip of the $4^{th}$ Metatarsal along the X axis.

$$A_{55} = \begin{bmatrix} \cos\theta_{55} & -\sin\theta_{55} & 0 & 0 \\ \sin\theta_{55} & \cos\theta_{55} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{55} \\ 0 & 0 & 0 & 1 \end{bmatrix} \begin{bmatrix} 1 & 0 & 0 & a_{55} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{55} & -\sin\alpha_{55} & 0 \\ 0 & \sin\alpha_{55} & \cos\alpha_{55} & 0 \\ 0 & 0 & 0 & 1 \end{bmatrix}$$

$$A_{55} = \begin{bmatrix} \cos\theta_{55} & -\sin\theta_{55}\cos\alpha_{55} & \sin\theta_{55}\sin\alpha_{55} & a_{55}\cos\theta_{55} \\ \sin\theta_{55} & \cos\theta_{55}\cos\alpha_{55} & -\cos\theta_{55}\sin\alpha_{55} & a_{55}\sin\theta_{55} \\ 0 & \sin\alpha_{55} & \cos\alpha_{55} & d_{55} \\ 0 & 0 & 0 & 1 \end{bmatrix}$$

Joint 56 connects the Left foot, $5^{th}$ toe Proximal Phalange to the Left foot $5^{th}$ toe Metatarsal. The $d_{56}$ link length of the $5^{th}$ Proximal Phalange runs collinear with the $5^{th}$ Proximal Phalange centroid running from the $5^{th}$ Proximal Phalange base to the tip of the $5^{th}$ Metatarsal along the X axis.

$$A_{56} = \begin{bmatrix} \cos\theta_{56} & -\sin\theta_{56} & 0 & 0 \\ \sin\theta_{56} & \cos\theta_{56} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{56} \\ 0 & 0 & 0 & 1 \end{bmatrix} \begin{bmatrix} 1 & 0 & 0 & a_{56} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{56} & -\sin\alpha_{56} & 0 \\ 0 & \sin\alpha_{56} & \cos\alpha_{56} & 0 \\ 0 & 0 & 0 & 1 \end{bmatrix}$$

$$A_{56} = \begin{bmatrix} \cos\theta_{56} & -\sin\theta_{56}\cos\alpha_{56} & \sin\theta_{56}\sin\alpha_{56} & a_{56}\cos\theta_{56} \\ \sin\theta_{56} & \cos\theta_{56}\cos\alpha_{56} & -\cos\theta_{56}\sin\alpha_{56} & a_{56}\sin\theta_{56} \\ 0 & \sin\alpha_{56} & \cos\alpha_{56} & d_{56} \\ 0 & 0 & 0 & 1 \end{bmatrix}$$

Joint 57 connects the Left foot, $1^{st}$ toe Metatarsal to the Left foot, $2^{nd}$ toe Metatarsal. The $d_{57}$ link length of the Left big toe Metatarsal runs collinear with the $1^{st}$ Metatarsal centroid running from the $1^{st}$ Metatarsal to the $2^{nd}$ Metatarsal along the Y axis. This is a touch joint of adjacent metatarsals.

$$A_{57} = \begin{bmatrix} \cos\theta_{57} & -\sin\theta_{57} & 0 & 0 \\ \sin\theta_{57} & \cos\theta_{57} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{57} \\ 0 & 0 & 0 & 1 \end{bmatrix} \begin{bmatrix} 1 & 0 & 0 & a_{57} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{57} & -\sin\alpha_{57} & 0 \\ 0 & \sin\alpha_{57} & \cos\alpha_{57} & 0 \\ 0 & 0 & 0 & 1 \end{bmatrix}$$

$$A_{57} = \begin{bmatrix} \cos\theta_{57} & -\sin\theta_{57}\cos\alpha_{57} & \sin\theta_{57}\sin\alpha_{57} & a_{57}\cos\theta_{57} \\ \sin\theta_{57} & \cos\theta_{57}\cos\alpha_{57} & -\cos\theta_{57}\sin\alpha_{57} & a_{57}\sin\theta_{57} \\ 0 & \sin\alpha_{57} & \cos\alpha_{57} & d_{57} \\ 0 & 0 & 0 & 1 \end{bmatrix}$$

Joint 58 connects the Left foot, $2^{nd}$ toe Metatarsal to the Left foot $3^{rd}$ toe Metatarsal. The $d_{23}$ link length of the Left $2^{nd}$ Metatarsal runs collinear with the $2^{nd}$ Metatarsal centroid running from the $2^{nd}$ Metatarsal to the $3^{rd}$ Metatarsal along the Y axis. This is a touch joint of adjacent metatarsals.

$$A_{58} = \begin{bmatrix} \cos\theta_{58} & -\sin\theta_{58} & 0 & 0 \\ \sin\theta_{58} & \cos\theta_{58} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{58} \\ 0 & 0 & 0 & 1 \end{bmatrix} \begin{bmatrix} 1 & 0 & 0 & a_{58} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{58} & -\sin\alpha_{58} & 0 \\ 0 & \sin\alpha_{58} & \cos\alpha_{58} & 0 \\ 0 & 0 & 0 & 1 \end{bmatrix}$$

$$A_{58} = \begin{bmatrix} \cos\theta_{58} & -\sin\theta_{58}\cos\alpha_{58} & \sin\theta_{58}\sin\alpha_{58} & a_{58}\cos\theta_{58} \\ \sin\theta_{58} & \cos\theta_{58}\cos\alpha_{58} & -\cos\theta_{58}\sin\alpha_{58} & a_{58}\sin\theta_{58} \\ 0 & \sin\alpha_{58} & \cos\alpha_{58} & d_{58} \\ 0 & 0 & 0 & 1 \end{bmatrix}$$

Joint 59 connects the Left foot, $3^{rd}$ toe Metatarsal to the Left foot, $4^{th}$ toe Metatarsal. The $d_{59}$ link length of the Left $4^{th}$ Metatarsal runs collinear with the $3^{rd}$ Metatarsal centroid running from the $3^{rd}$ Metatarsal to the $3^{rd}$ Metatarsal along the X axis. This is a touch joint of adjacent metatarsals.

$$A_{59} = \begin{bmatrix} \cos\theta_{59} & -\sin\theta_{59} & 0 & 0 \\ \sin\theta_{59} & \cos\theta_{59} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{59} \\ 0 & 0 & 0 & 1 \end{bmatrix} \begin{bmatrix} 1 & 0 & 0 & a_{59} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{59} & -\sin\alpha_{59} & 0 \\ 0 & \sin\alpha_{59} & \cos\alpha_{59} & 0 \\ 0 & 0 & 0 & 1 \end{bmatrix}$$

$$A_{59} = \begin{bmatrix} \cos\theta_{59} & -\sin\theta_{59}\cos\alpha_{59} & \sin\theta_{59}\sin\alpha_{59} & a_{59}\cos\theta_{59} \\ \sin\theta_{59} & \cos\theta_{59}\cos\alpha_{59} & -\cos\theta_{59}\sin\alpha_{59} & a_{59}\sin\theta_{59} \\ 0 & \sin\alpha_{59} & \cos\alpha_{59} & d_{59} \\ 0 & 0 & 0 & 1 \end{bmatrix}$$

Joint 60 connects the Left foot, 4th toe Metatarsal to the Left foot $5^{th}$ toe Metatarsal. The $d_{60}$ link length of the Left $4^{th}$ Metatarsal runs collinear with the $4^{th}$ Metatarsal centroid running from the $4^{th}$ Metatarsal to the $5^{th}$ Metatarsal along the Y axis. This is a touch joint of adjacent metatarsals.

$$A_{60} = \begin{bmatrix} \cos\theta_{60} & -\sin\theta_{60} & 0 & 0 \\ \sin\theta_{60} & \cos\theta_{60} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{60} \\ 0 & 0 & 0 & 1 \end{bmatrix} \begin{bmatrix} 1 & 0 & 0 & a_{60} \\ 0 & 1 & 0 & 0 \\ 0 & 0 & 1 & 0 \\ 0 & 0 & 0 & 1 \end{bmatrix}$$

-continued $$A_{60} = \begin{bmatrix} 1 & 0 & 0 & 0 \\ 0 & \cos\alpha_{60} & -\sin\alpha_{60} & 0 \\ 0 & \sin\alpha_{60} & \cos\alpha_{60} & 0 \\ 0 & 0 & 0 & 1 \end{bmatrix}$$

$$A_{60} = \begin{bmatrix} \cos\theta_{60} & -\sin\theta_{60}\cos\alpha_{60} & \sin\theta_{60}\sin\alpha_{60} & a_{60}\cos\theta_{60} \\ \sin\theta_{60} & \cos\theta_{60}\cos\alpha_{60} & -\cos\theta_{60}\sin\alpha_{60} & a_{60}\sin\theta_{60} \\ 0 & \sin\alpha_{60} & \cos\alpha_{60} & d_{60} \\ 0 & 0 & 0 & 1 \end{bmatrix}$$

Joint 61 connects the Left foot, $1^{st}$ toe Metatarsal to the Left foot Medial Cuneiform. The $d_{61}$ link length of the Left big toe Metatarsal runs collinear with the $1^{st}$ Metatarsal centroid running from the $1^{st}$ Metatarsal base to the tip of the $1^{st}$ Medial Cuneiform along the X axis.

$$A_{61} = \begin{bmatrix} \cos\theta_{61} & -\sin\theta_{61} & 0 & 0 \\ \sin\theta_{61} & \cos\theta_{61} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{61} \\ 0 & 0 & 0 & 1 \end{bmatrix} \begin{bmatrix} 1 & 0 & 0 & a_{61} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{61} & -\sin\alpha_{61} & 0 \\ 0 & \sin\alpha_{61} & \cos\alpha_{61} & 0 \\ 0 & 0 & 0 & 1 \end{bmatrix}$$

$$A_{61} = \begin{bmatrix} \cos\theta_{61} & -\sin\theta_{61}\cos\alpha_{61} & \sin\theta_{61}\sin\alpha_{61} & a_{61}\cos\theta_{61} \\ \sin\theta_{61} & \cos\theta_{61}\cos\alpha_{61} & -\cos\theta_{61}\sin\alpha_{61} & a_{61}\sin\theta_{61} \\ 0 & \sin\alpha_{61} & \cos\alpha_{61} & d_{61} \\ 0 & 0 & 0 & 1 \end{bmatrix}$$

Joint 62 connects the Left foot, $2^{nd}$ toe Metatarsal to the Left foot Medial Cuneiform. The $d_{62}$ link length of the Left big toe Metatarsal runs collinear with the $2^{nd}$ Metatarsal centroid running from the $2^{nd}$ Metatarsal base to the tip of the $2^{nd}$ Medial Cuneiform along the X axis.

$$A_{62} = \begin{bmatrix} \cos\theta_{62} & -\sin\theta_{62} & 0 & 0 \\ \sin\theta_{62} & \cos\theta_{62} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{62} \\ 0 & 0 & 0 & 1 \end{bmatrix} \begin{bmatrix} 1 & 0 & 0 & a_{62} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{62} & -\sin\alpha_{62} & 0 \\ 0 & \sin\alpha_{62} & \cos\alpha_{62} & 0 \\ 0 & 0 & 0 & 1 \end{bmatrix}$$

$$A_{62} = \begin{bmatrix} \cos\theta_{62} & -\sin\theta_{62}\cos\alpha_{62} & \sin\theta_{62}\sin\alpha_{62} & a_{62}\cos\theta_{62} \\ \sin\theta_{62} & \cos\theta_{62}\cos\alpha_{62} & -\cos\theta_{62}\sin\alpha_{62} & a_{62}\sin\theta_{62} \\ 0 & \sin\alpha_{62} & \cos\alpha_{62} & d_{62} \\ 0 & 0 & 0 & 1 \end{bmatrix}$$

Joint 63 connects the Left foot, $2^{nd}$ toe Metatarsal to the Left foot Intermediate Cuneiform. The $d_{63}$ link length of the Left $2^{nd}$ Metatarsal runs collinear with the Left Intermediate Cuneiform centroid running from the $2^{nd}$ Metatarsal base to the tip of the Left Intermediate Cuneiform along the X axis $$A_{63} = \begin{bmatrix} \cos\theta_{63} & -\sin\theta_{63} & 0 & 0 \\ \sin\theta_{63} & \cos\theta_{63} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{63} \\ 0 & 0 & 0 & 1 \end{bmatrix} \begin{bmatrix} 1 & 0 & 0 & a_{63} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{63} & -\sin\alpha_{63} & 0 \\ 0 & \sin\alpha_{63} & \cos\alpha_{63} & 0 \\ 0 & 0 & 0 & 1 \end{bmatrix}$$

$$A_{63} = \begin{bmatrix} \cos\theta_{63} & -\sin\theta_{63}\cos\alpha_{63} & \sin\theta_{63}\sin\alpha_{63} & a_{63}\cos\theta_{63} \\ \sin\theta_{63} & \cos\theta_{63}\cos\alpha_{63} & -\cos\theta_{63}\sin\alpha_{63} & a_{63}\sin\theta_{63} \\ 0 & \sin\alpha_{63} & \cos\alpha_{63} & d_{63} \\ 0 & 0 & 0 & 1 \end{bmatrix}$$

Joint 64 connects the Left foot, $2^{nd}$ toe Metatarsal to the Left foot Lateral Cuneiform. The $d_{64}$ link length of the Left big toe Metatarsal runs collinear with the $2^{nd}$ Metatarsal centroid running from the $2^{nd}$ Metatarsal base to the tip of the Left Lateral Cuneiform along the X axis.

$$A_{64} = \begin{bmatrix} \cos\theta_{64} & -\sin\theta_{64} & 0 & 0 \\ \sin\theta_{64} & \cos\theta_{64} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{64} \\ 0 & 0 & 0 & 1 \end{bmatrix} \begin{bmatrix} 1 & 0 & 0 & a_{64} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{64} & -\sin\alpha_{64} & 0 \\ 0 & \sin\alpha_{64} & \cos\alpha_{64} & 0 \\ 0 & 0 & 0 & 1 \end{bmatrix}$$

$$A_{64} = \begin{bmatrix} \cos\theta_{64} & -\sin\theta_{64}\cos\alpha_{64} & \sin\theta_{64}\sin\alpha_{64} & a_{64}\cos\theta_{64} \\ \sin\theta_{64} & \cos\theta_{64}\cos\alpha_{64} & -\cos\theta_{64}\sin\alpha_{64} & a_{64}\sin\theta_{64} \\ 0 & \sin\alpha_{64} & \cos\alpha_{64} & d_{64} \\ 0 & 0 & 0 & 1 \end{bmatrix}$$

Joint 65 connects the Left foot, $3^{rd}$ toe Metatarsal to the Left foot Lateral Cuneiform. The $d_{65}$ link length of the Left $3^{rd}$ Metatarsal runs collinear with the $3^{rd}$ Metatarsal centroid running from the $3^{rd}$ Metatarsal base to the tip of the $3^{rd}$ Lateral Cuneiform along the X axis.

$$A_{65} = \begin{bmatrix} \cos\theta_{65} & -\sin\theta_{65} & 0 & 0 \\ \sin\theta_{65} & \cos\theta_{65} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{65} \\ 0 & 0 & 0 & 1 \end{bmatrix} \begin{bmatrix} 1 & 0 & 0 & a_{65} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{65} & -\sin\alpha_{65} & 0 \\ 0 & \sin\alpha_{65} & \cos\alpha_{65} & 0 \\ 0 & 0 & 0 & 1 \end{bmatrix}$$

$$A_{65} = \begin{bmatrix} \cos\theta_{65} & -\sin\theta_{65}\cos\alpha_{65} & \sin\theta_{65}\sin\alpha_{65} & a_{65}\cos\theta_{65} \\ \sin\theta_{65} & \cos\theta_{65}\cos\alpha_{65} & -\cos\theta_{65}\sin\alpha_{65} & a_{65}\sin\theta_{65} \\ 0 & \sin\alpha_{65} & \cos\alpha_{65} & d_{65} \\ 0 & 0 & 0 & 1 \end{bmatrix}$$

Joint 66 connects the left foot, $4^{th}$ toe Metatarsal to the left fool Lateral Cuneiform. The $d_{66}$ link length of the left $4^{th}$ Metatarsal runs collinear with the $4^{th}$ Metatarsal centroid running from the $4^{th}$ Metatarsal base to the tip of the Lateral Cuneiform along the X axis.

$$A_{66} = \begin{bmatrix} \cos\theta_{66} & -\sin\theta_{66} & 0 & 0 \\ \sin\theta_{66} & \cos\theta_{66} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{66} \\ 0 & 0 & 0 & 1 \end{bmatrix} \begin{bmatrix} 1 & 0 & 0 & a_{66} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{66} & -\sin\alpha_{66} & 0 \\ 0 & \sin\alpha_{66} & \cos\alpha_{66} & 0 \\ 0 & 0 & 0 & 1 \end{bmatrix}$$

$$A_{66} = \begin{bmatrix} \cos\theta_{66} & -\sin\theta_{66}\cos\alpha_{66} & \sin\theta_{66}\sin\alpha_{66} & a_{66}\cos\theta_{66} \\ \sin\theta_{66} & \cos\theta_{66}\cos\alpha_{66} & -\cos\theta_{66}\sin\alpha_{66} & a_{66}\sin\theta_{66} \\ 0 & \sin\alpha_{66} & \cos\alpha_{66} & d_{66} \\ 0 & 0 & 0 & 1 \end{bmatrix}$$

Joint 67 connects the Left foot, 4th toe Metatarsal to the Left foot Cuboid bone. The $d_{67}$ link length of the Left $4^{th}$ Metatarsal runs collinear with the 4th Metatarsal centroid running from the $4^{th}$ Metatarsal base to the tip of the Left Cuboid along the X axis.

$$A_{67} = \begin{bmatrix} \cos\theta_{67} & -\sin\theta_{67} & 0 & 0 \\ \sin\theta_{67} & \cos\theta_{67} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{67} \\ 0 & 0 & 0 & 1 \end{bmatrix} \begin{bmatrix} 1 & 0 & 0 & a_{67} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{67} & -\sin\alpha_{67} & 0 \\ 0 & \sin\alpha_{67} & \cos\alpha_{67} & 0 \\ 0 & 0 & 0 & 1 \end{bmatrix}$$

$$A_{67} = \begin{bmatrix} \cos\theta_{67} & -\sin\theta_{67}\cos\alpha_{67} & \sin\theta_{67}\sin\alpha_{67} & a_{67}\cos\theta_{67} \\ \sin\theta_{67} & \cos\theta_{67}\cos\alpha_{67} & -\cos\theta_{67}\sin\alpha_{67} & a_{67}\sin\theta_{67} \\ 0 & \sin\alpha_{67} & \cos\alpha_{67} & d_{67} \\ 0 & 0 & 0 & 1 \end{bmatrix}$$

Joint 68 connects the Left foot, 5th toe Metatarsal to the Left foot Cuboid bone. The $d_{68}$ link length of the Left 5th Metatarsal runs collinear with the 5th Metatarsal centroid running from the $5^{th}$ Metatarsal base to the tip of the Left Cuboid along the X axis.

$$A_{68} = \begin{bmatrix} \cos\theta_{68} & -\sin\theta_{68} & 0 & 0 \\ \sin\theta_{68} & \cos\theta_{68} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{68} \\ 0 & 0 & 0 & 1 \end{bmatrix} \begin{bmatrix} 1 & 0 & 0 & a_{68} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{68} & -\sin\alpha_{68} & 0 \\ 0 & \sin\alpha_{68} & \cos\alpha_{68} & 0 \\ 0 & 0 & 0 & 1 \end{bmatrix}$$

-continued $$A_{68} = \begin{bmatrix} \cos\theta_{68} & -\sin\theta_{68}\cos\alpha_{68} & \sin\theta_{68}\sin\alpha_{68} & a_{68}\cos\theta_{68} \\ \sin\theta_{68} & \cos\theta_{68}\cos\alpha_{68} & -\cos\theta_{68}\sin\alpha_{68} & a_{68}\sin\theta_{68} \\ 0 & \sin\alpha_{68} & \cos\alpha_{68} & d_{68} \\ 0 & 0 & 0 & 1 \end{bmatrix}$$

Joint 69 connects the Left foot, Medial Cuneiform bone to the Left foot Intermediate Cuneiform bone. The $d_{69}$ link length of the Left Medial Cuneiform runs collinear with the Left Medial Cuneiform running from the Medial Cuneiform to the Left Intermediate Cuneiform along the Y axis.

$$A_{69} = \begin{bmatrix} \cos\theta_{69} & -\sin\theta_{69} & 0 & 0 \\ \sin\theta_{69} & \cos\theta_{69} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{69} \\ 0 & 0 & 0 & 1 \end{bmatrix} \begin{bmatrix} 1 & 0 & 0 & a_{69} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{69} & -\sin\alpha_{69} & 0 \\ 0 & \sin\alpha_{69} & \cos\alpha_{69} & 0 \\ 0 & 0 & 0 & 1 \end{bmatrix}$$

$$A_{69} = \begin{bmatrix} \cos\theta_{69} & -\sin\theta_{69}\cos\alpha_{69} & \sin\theta_{69}\sin\alpha_{69} & a_{69}\cos\theta_{69} \\ \sin\theta_{69} & \cos\theta_{69}\cos\alpha_{69} & -\cos\theta_{69}\sin\alpha_{69} & a_{69}\sin\theta_{69} \\ 0 & \sin\alpha_{69} & \cos\alpha_{69} & d_{69} \\ 0 & 0 & 0 & 1 \end{bmatrix}$$

Joint 70 connects the left foot, Intermediate Cuneiform to the Left foot Lateral Cuneiform. The $d_{70}$ link length of the left Intermediate Cuneiform runs collinear with left Intermediate Cuneiform running from the Left Intermediate Cuneiform to the Lateral Cuneiform along the Y axis.

$$A_{70} = \begin{bmatrix} \cos\theta_{70} & -\sin\theta_{70} & 0 & 0 \\ \sin\theta_{70} & \cos\theta_{70} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{70} \\ 0 & 0 & 0 & 1 \end{bmatrix} \begin{bmatrix} 1 & 0 & 0 & a_{70} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{70} & -\sin\alpha_{70} & 0 \\ 0 & \sin\alpha_{70} & \cos\alpha_{70} & 0 \\ 0 & 0 & 0 & 1 \end{bmatrix}$$

$$A_{70} = \begin{bmatrix} \cos\theta_{70} & -\sin\theta_{70}\cos\alpha_{70} & \sin\theta_{70}\sin\alpha_{70} & a_{70}\cos\theta_{70} \\ \sin\theta_{70} & \cos\theta_{70}\cos\alpha_{70} & -\cos\theta_{70}\sin\alpha_{70} & a_{70}\sin\theta_{70} \\ 0 & \sin\alpha_{70} & \cos\alpha_{70} & d_{70} \\ 0 & 0 & 0 & 1 \end{bmatrix}$$

Joint 71 connects the Left foot, Lateral Cuneiform to the left foot Cuboid. The $d_{71}$ link length of the Left Lateral Cuneiform runs collinear with the Left Lateral Cuneiform centroid running from the Left Lateral Cuneiform base to the tip of the Left Cuboid along the X axis.

$$A_{71} = \begin{bmatrix} \cos\theta_{71} & -\sin\theta_{71} & 0 & 0 \\ \sin\theta_{71} & \cos\theta_{71} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{71} \\ 0 & 0 & 0 & 1 \end{bmatrix} \begin{bmatrix} 1 & 0 & 0 & a_{71} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{71} & -\sin\alpha_{71} & 0 \\ 0 & \sin\alpha_{71} & \cos\alpha_{71} & 0 \\ 0 & 0 & 0 & 1 \end{bmatrix}$$

$$A_{71} = \begin{bmatrix} \cos\theta_{71} & -\sin\theta_{71}\cos\alpha_{71} & \sin\theta_{71}\sin\alpha_{71} & a_{71}\cos\theta_{71} \\ \sin\theta_{71} & \cos\theta_{71}\cos\alpha_{71} & -\cos\theta_{71}\sin\alpha_{71} & a_{71}\sin\theta_{71} \\ 0 & \sin\alpha_{71} & \cos\alpha_{71} & d_{71} \\ 0 & 0 & 0 & 1 \end{bmatrix}$$

Joint 72 connects the Left foot, Medial Cuneiform bone to the Left foot Navicular bone. The $d_{70}$ link length of the Left Medial Cuneiform runs collinear with the Left Medial Cuneiform running from the Left Medial Cuneiform base to the tip of the Navicular along the X axis.

$$A_{72} = \begin{bmatrix} \cos\theta_{72} & -\sin\theta_{72} & 0 & 0 \\ \sin\theta_{72} & \cos\theta_{72} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{72} \\ 0 & 0 & 0 & 1 \end{bmatrix} \begin{bmatrix} 1 & 0 & 0 & a_{72} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{72} & -\sin\alpha_{72} & 0 \\ 0 & \sin\alpha_{72} & \cos\alpha_{72} & 0 \\ 0 & 0 & 0 & 1 \end{bmatrix}$$

$$A_{72} = \begin{bmatrix} \cos\theta_{72} & -\sin\theta_{72}\cos\alpha_{72} & \sin\theta_{72}\sin\alpha_{72} & a_{72}\cos\theta_{72} \\ \sin\theta_{72} & \cos\theta_{72}\cos\alpha_{72} & -\cos\theta_{72}\sin\alpha_{72} & a_{72}\sin\theta_{72} \\ 0 & \sin\alpha_{72} & \cos\alpha_{72} & d_{72} \\ 0 & 0 & 0 & 1 \end{bmatrix}$$

Joint 73 connects the Left foot, Intermediate Cuneiform bone to the Left foot Navicular bone. This joint is both rotational of the Left Intermediate Cuneiform bone about the Left Navicular. The $d_{73}$ link length of the Left Intermediate Cuneiform runs collinear with the Left Intermediate Cuneiform running from the Left Intermediate Cuneiform base to the tip of the Left Navicular along the X axis.

$$A_{73} = \begin{bmatrix} \cos\theta_{73} & -\sin\theta_{73} & 0 & 0 \\ \sin\theta_{73} & \cos\theta_{73} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{73} \\ 0 & 0 & 0 & 1 \end{bmatrix} \begin{bmatrix} 1 & 0 & 0 & a_{73} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{73} & -\sin\alpha_{73} & 0 \\ 0 & \sin\alpha_{73} & \cos\alpha_{73} & 0 \\ 0 & 0 & 0 & 1 \end{bmatrix}$$

$$A_{73} = \begin{bmatrix} \cos\theta_{73} & -\sin\theta_{73}\cos\alpha_{73} & \sin\theta_{73}\sin\alpha_{73} & a_{73}\cos\theta_{73} \\ \sin\theta_{73} & \cos\theta_{73}\cos\alpha_{73} & -\cos\theta_{73}\sin\alpha_{73} & a_{73}\sin\theta_{73} \\ 0 & \sin\alpha_{73} & \cos\alpha_{73} & d_{73} \\ 0 & 0 & 0 & 1 \end{bmatrix}$$

Joint 74 connects the Left foot, lateral Cuneiform bone to the Left foot Navicular bone. This joint is both rotational of the Left lateral Cuneiform bone about the Left Navicular in the X plane, and rotation of the Left lateral Cuneiform bone about the Left Navicular in the Y plane, in an oblong interface supporting rotational motion in two direction. There is no linear motion in either the X plane or the Y plane in this joint.

$$A_{74} = \begin{bmatrix} \cos\theta_{74} & -\sin\theta_{74} & 0 & 0 \\ \sin\theta_{74} & \cos\theta_{74} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{74} \\ 0 & 0 & 0 & 1 \end{bmatrix} \begin{bmatrix} 1 & 0 & 0 & a_{74} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{74} & -\sin\alpha_{74} & 0 \\ 0 & \sin\alpha_{74} & \cos\alpha_{74} & 0 \\ 0 & 0 & 0 & 1 \end{bmatrix}$$

$$A_{74} = \begin{bmatrix} \cos\theta_{74} & -\sin\theta_{74}\cos\alpha_{74} & \sin\theta_{74}\sin\alpha_{74} & a_{74}\cos\theta_{74} \\ \sin\theta_{74} & \cos\theta_{74}\cos\alpha_{74} & -\cos\theta_{74}\sin\alpha_{74} & a_{74}\sin\theta_{74} \\ 0 & \sin\alpha_{74} & \cos\alpha_{74} & d_{74} \\ 0 & 0 & 0 & 1 \end{bmatrix}$$

Joint 75 connects the Left foot, Navicular to the Left foot Cuboid. The $d_{75}$ link length of the Left Navicular runs collinear with the Left Navicular centroid running from the Left Navicular to the Cuboid along the Y axis.

$$A_{75} = \begin{bmatrix} \cos\theta_{75} & -\sin\theta_{75} & 0 & 0 \\ \sin\theta_{75} & \cos\theta_{75} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{75} \\ 0 & 0 & 0 & 1 \end{bmatrix} \begin{bmatrix} 1 & 0 & 0 & a_{75} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{75} & -\sin\alpha_{75} & 0 \\ 0 & \sin\alpha_{75} & \cos\alpha_{75} & 0 \\ 0 & 0 & 0 & 1 \end{bmatrix}$$

$$A_{75} = \begin{bmatrix} \cos\theta_{75} & -\sin\theta_{75}\cos\alpha_{75} & \sin\theta_{75}\sin\alpha_{75} & a_{75}\cos\theta_{75} \\ \sin\theta_{75} & \cos\theta_{75}\cos\alpha_{75} & -\cos\theta_{75}\sin\alpha_{75} & a_{75}\sin\theta_{75} \\ 0 & \sin\alpha_{75} & \cos\alpha_{75} & d_{75} \\ 0 & 0 & 0 & 1 \end{bmatrix}$$

Joint 76 connects the Left foot, Navicular bone to the Left foot Talus bone. This joint is a rotational joint with respect to the Navicular bone and the Talus bone in the Z plane and is also a rotational joint with respect to the Navicular bone and the Talus bone in the Y plane. There is no linear lateral motion in this joint, rather, the curved structure of the Talus-Navicular interface is curved, thus supporting only rotation.

$$A_{76} = \begin{bmatrix} \cos\theta_{76} & -\sin\theta_{76} & 0 & 0 \\ \sin\theta_{76} & \cos\theta_{76} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{76} \\ 0 & 0 & 0 & 1 \end{bmatrix} \begin{bmatrix} 1 & 0 & 0 & a_{76} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{76} & -\sin\alpha_{76} & 0 \\ 0 & \sin\alpha_{76} & \cos\alpha_{76} & 0 \\ 0 & 0 & 0 & 1 \end{bmatrix}$$

$$A_{76} = \begin{bmatrix} \cos\theta_{76} & -\sin\theta_{76}\cos\alpha_{76} & \sin\theta_{76}\sin\alpha_{76} & a_{76}\cos\theta_{76} \\ \sin\theta_{76} & \cos\theta_{76}\cos\alpha_{76} & -\cos\theta_{76}\sin\alpha_{76} & a_{76}\sin\theta_{76} \\ 0 & \sin\alpha_{76} & \cos\alpha_{76} & d_{76} \\ 0 & 0 & 0 & 1 \end{bmatrix}$$

Joint 77 connects the Left foot, Cuboid to the Left foot Calcaneus. The $d_{77}$ link length of the Left Calcaneus runs collinear with the Left Cuboid running from the Left Cuboid base to the tip of the Left Calcaneus along the X axis.

$$A_{77} = \begin{bmatrix} \cos\theta_{77} & -\sin\theta_{77} & 0 & 0 \\ \sin\theta_{77} & \cos\theta_{77} & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_{77} \\ 0 & 0 & 0 & 1 \end{bmatrix}\begin{bmatrix} 1 & 0 & 0 & a_{77} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{77} & -\sin\alpha_{77} & 0 \\ 0 & \sin\alpha_{77} & \cos\alpha_{77} & 0 \\ 0 & 0 & 0 & 1 \end{bmatrix}$$

$$A_{77} = \begin{bmatrix} \cos\theta_{77} & -\sin\theta_{77}\cos\alpha_{77} & \sin\theta_{77}\sin\alpha_{77} & a_{77}\cos\theta_{77} \\ \sin\theta_{77} & \cos\theta_{77}\cos\alpha_{77} & -\cos\theta_{77}\sin\alpha_{77} & a_{77}\sin\theta_{77} \\ 0 & \sin\alpha_{77} & \cos\alpha_{77} & d_{77} \\ 0 & 0 & 0 & 1 \end{bmatrix}$$

Joint 78 connects the Left foot, Talus to the left foot Calcaneus. The $d_{78}$ link length of the left Talus runs collinear with the left Talus running from the Talus to the Calcaneus along the Y axis.

$$A_{78} = \begin{bmatrix} \cos\theta_{78} & -\sin\theta_{78} & 0 & 0 \\ \sin\theta_{78} & \cos\theta_{78} & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_{78} \\ 0 & 0 & 0 & 1 \end{bmatrix}\begin{bmatrix} 1 & 0 & 0 & a_{78} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{78} & -\sin\alpha_{78} & 0 \\ 0 & \sin\alpha_{78} & \cos\alpha_{78} & 0 \\ 0 & 0 & 0 & 1 \end{bmatrix}$$

$$A_{78} = \begin{bmatrix} \cos\theta_{78} & -\sin\theta_{78}\cos\alpha_{78} & \sin\theta_{78}\sin\alpha_{78} & a_{78}\cos\theta_{78} \\ \sin\theta_{78} & \cos\theta_{78}\cos\alpha_{78} & -\cos\theta_{78}\sin\alpha_{78} & a_{78}\sin\theta_{78} \\ 0 & \sin\alpha_{78} & \cos\alpha_{78} & d_{78} \\ 0 & 0 & 0 & 1 \end{bmatrix}$$

Joint 79 connects the Left Fibula to the Left Talus bone, this is commonly referred to as the ankle joint. The $d_{79}$ link length of the Left Fibula runs collinear with the Left Fibula running from the Fibula base to the Talus along the X axis.

$$A_{79} = \begin{bmatrix} \cos\theta_{79} & -\sin\theta_{79} & 0 & 0 \\ \sin\theta_{79} & \cos\theta_{79} & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_{79} \\ 0 & 0 & 0 & 1 \end{bmatrix}\begin{bmatrix} 1 & 0 & 0 & a_{79} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{79} & -\sin\alpha_{79} & 0 \\ 0 & \sin\alpha_{79} & \cos\alpha_{79} & 0 \\ 0 & 0 & 0 & 1 \end{bmatrix}$$

$$A_{79} = \begin{bmatrix} \cos\theta_{79} & -\sin\theta_{79}\cos\alpha_{79} & \sin\theta_{79}\sin\alpha_{79} & a_{79}\cos\theta_{79} \\ \sin\theta_{79} & \cos\theta_{79}\cos\alpha_{79} & -\cos\theta_{79}\sin\alpha_{79} & a_{79}\sin\theta_{79} \\ 0 & \sin\alpha_{79} & \cos\alpha_{79} & d_{79} \\ 0 & 0 & 0 & 1 \end{bmatrix}$$

Joint 80 connects the Left tibia to the Left talus bone. The $d_{80}$ link length of the Left Tibia runs collinear with the Left Tibia running from the Fibula base to the Talus along the X axis.

$$A_{80} = \begin{bmatrix} \cos\theta_{80} & -\sin\theta_{80} & 0 & 0 \\ \sin\theta_{80} & \cos\theta_{80} & 0 & 0 \\ 0 & 0 & 1 & 0 \\ 0 & 0 & 0 & 1 \end{bmatrix}\begin{bmatrix} 1 & 0 & 0 & 0 \\ 0 & 1 & 0 & 0 \\ 0 & 0 & 1 & d_{80} \\ 0 & 0 & 0 & 1 \end{bmatrix}\begin{bmatrix} 1 & 0 & 0 & a_{80} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{80} & -\sin\alpha_{80} & 0 \\ 0 & \sin\alpha_{80} & \cos\alpha_{80} & 0 \\ 0 & 0 & 0 & 1 \end{bmatrix}$$

$$A_{80} = \begin{bmatrix} \cos\theta_{80} & -\sin\theta_{80}\cos\alpha_{80} & \sin\theta_{80}\sin\alpha_{80} & a_{80}\cos\theta_{80} \\ \sin\theta_{80} & \cos\theta_{80}\cos\alpha_{80} & -\cos\theta_{80}\sin\alpha_{80} & a_{80}\sin\theta_{80} \\ 0 & \sin\alpha_{80} & \cos\alpha_{80} & d_{80} \\ 0 & 0 & 0 & 1 \end{bmatrix}$$

Joint 81 connects the Dorsal end of the Left Tibia to the Dorsal end of the Left Fibula to form the Dorsal Tibiofibular joint. The $d_{81}$ link length of the Left Doral Tibia runs collinear with the Left Dorsal Tibia running from the Dorsal Tibia to the Left Dorsal Fibula along the Y axis.

$$A_{81} = \begin{bmatrix} \cos\theta_{81} & -\sin\theta_{81} & 0 & 0 \\ \sin\theta_{81} & \cos\theta_{81} & 0 & 0 \\ 0 & 0 & 1 & d_{81} \\ 0 & 0 & 0 & 1 \end{bmatrix}\begin{bmatrix} 1 & 0 & 0 & 0 \\ 0 & 1 & 0 & 0 \\ 0 & 0 & 1 & d_{81} \\ 0 & 0 & 0 & 1 \end{bmatrix}\begin{bmatrix} 1 & 0 & 0 & a_{81} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{81} & -\sin\alpha_{81} & 0 \\ 0 & \sin\alpha_{81} & \cos\alpha_{81} & 0 \\ 0 & 0 & 0 & 1 \end{bmatrix}$$

$$A_{81} = \begin{bmatrix} \cos\theta_{81} & -\sin\theta_{81}\cos\alpha_{81} & \sin\theta_{81}\sin\alpha_{81} & a_{81}\cos\theta_{81} \\ \sin\theta_{81} & \cos\theta_{81}\cos\alpha_{81} & -\cos\theta_{81}\sin\alpha_{81} & a_{81}\sin\theta_{81} \\ 0 & \sin\alpha_{81} & \cos\alpha_{81} & d_{81} \\ 0 & 0 & 0 & 1 \end{bmatrix}$$

Joint 82 connects the Proximal end of the Left Tibia to the Proximal end of the Left Fibula to form the Proximal Tibiofibular joint. The $d_{82}$ link length of the Left Proximal Tibia runs collinear with the Left Proximal Tibia running from the Proximal Tibia to the Left Proximal Fibula along the Y axis.

$$A_{82} = \begin{bmatrix} \cos\theta_{82} & -\sin\theta_{82} & 0 & 0 \\ \sin\theta_{82} & \cos\theta_{82} & 0 & 0 \\ 0 & 0 & 1 & d_{82} \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{82} & 1 \end{bmatrix} \begin{bmatrix} 1 & 0 & 0 & a_{82} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{82} & -\sin\alpha_{82} & 0 \\ 0 & \sin\alpha_{82} & \cos\alpha_{82} & 0 \\ 0 & 0 & 0 & 1 \end{bmatrix}$$

$$A_{82} = \begin{bmatrix} \cos\theta_{82} & -\sin\theta_{82}\cos\alpha_{82} & \sin\theta_{82}\sin\alpha_{82} & a_{82}\cos\theta_{82} \\ \sin\theta_{82} & \cos\theta_{82}\cos\alpha_{82} & -\cos\theta_{82}\sin\alpha_{82} & a_{82}\sin\theta_{82} \\ 0 & \sin\alpha_{82} & \cos\alpha_{82} & d_{82} \\ 0 & 0 & 0 & 1 \end{bmatrix}$$

Joint 83 connects the Proximal end of the Tibia with the Distal end of the Femur to create the Left Femorotibial joint. Normal range of motion (ROM) at the knee is considered to be zero (0) degrees of extension (completely straight knee joint) to 135 degrees of flexion (fully bent knee joint). The knee joint is one of the strongest and most important joints in the human body. It enables the lower leg to move relative to the femur while supporting the body's weight. Movements at the knee joint are essential to walking, running, sitting and standing. The knee is a synovial hinge joint formed between three bones: the Femur, Tibia, and Patella. Two rounded convex processes (known as condyles) on the Distal end of the Femur meet two rounded, concave condyles at the Proximal end of the Tibia. A special characteristic of the knee that differentiates it from other hinge joints is that it allows a small degree of medial and lateral rotation when it is moderately flexed.

$$A_{83} = \begin{bmatrix} \cos\theta_{83} & -\sin\theta_{83} & 0 & 0 \\ \sin\theta_{83} & \cos\theta_{83} & 0 & 0 \\ 0 & 0 & 1 & d_{83} \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ 0 & 0 & d_{83} & 1 \end{bmatrix} \begin{bmatrix} 1 & 0 & 0 & a_{83} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{83} & -\sin\alpha_{83} & 0 \\ 0 & \sin\alpha_{83} & \cos\alpha_{83} & 0 \\ 0 & 0 & 0 & 1 \end{bmatrix}$$

$$A_{83} = \begin{bmatrix} \cos\theta_{83} & -\sin\theta_{83}\cos\alpha_{83} & \sin\theta_{83}\sin\alpha_{83} & a_{83}\cos\theta_{83} \\ \sin\theta_{83} & \cos\theta_{83}\cos\alpha_{83} & -\cos\theta_{83}\sin\alpha_{83} & a_{83}\sin\theta_{83} \\ 0 & \sin\alpha_{83} & \cos\alpha_{83} & d_{83} \\ 0 & 0 & 0 & 1 \end{bmatrix}$$

Joint 84 connects the Left femur Proximal end to the Left pelvis socket, forming the Left hip joint.

$$A_{84} = \begin{bmatrix} \cos\varphi_{84} & -\sin\varphi_{84} & 0 & 0 \\ \sin\varphi_{84} & \cos\varphi_{84} & 0 & 0 \\ 0 & 0 & 1 & d_{84} \\ 0 & 0 & 0 & 1 \end{bmatrix} \begin{bmatrix} \cos\theta_{84} & 0 & \sin\theta_{84} & 0 \\ 0 & 1 & 0 & 0 \\ -\sin\theta_{84} & 0 & \cos\theta_{84} & 0 \\ 0 & 0 & 0 & 1 \end{bmatrix}$$

$$\begin{bmatrix} 1 & 0 & 0 & 0 \\ 0 & \cos\psi_{84} & -\sin\psi_{84} & 0 \\ 0 & \sin\psi_{84} & \cos\psi_{84} & 0 \\ 0 & 0 & 0 & 1 \end{bmatrix}$$

$$A_{84} = \begin{bmatrix} \cos\theta_{84} & -\sin\theta_{84}\cos\alpha_{84} & \sin\theta_{84}\sin\alpha_{84} & a_{84}\cos\theta_{84} \\ \sin\theta_{84} & \cos\theta_{84}\cos\alpha_{84} & -\cos\theta_{84}\sin\alpha_{84} & a_{84}\sin\theta_{84} \\ 0 & \sin\alpha_{84} & \cos\alpha_{84} & d_{84} \\ 0 & 0 & 0 & 1 \end{bmatrix}$$

Joint 85 connects the $0^{th}$ Cervical Vertebra to the $1^{st}$ Cervical Vertebra and is known as the occipito-atlanto joint. The C1 Vertebra is also known as the Atlas. The occipito-atlanto joint is a synovial joint whose main purpose is to bend forward and backward. It is formed by paired occipital condyles and superior articular facets of the atlas. The $d_{85}$ link length of the C0 vertebra runs collinear with the C0 vertebra running from the head of the C1 vertebra to the base of the skull along the X axis.

$$A_{85} = \begin{bmatrix} \cos\varphi_{85} & -\sin\varphi_{85} & 0 & 0 \\ \sin\varphi_{85} & \cos\varphi_{85} & 0 & 0 \\ 0 & 0 & 1 & d_{85} \\ 0 & 0 & 0 & 1 \end{bmatrix} \begin{bmatrix} \cos\theta_{85} & 0 & \sin\theta_{85} & 0 \\ 0 & 1 & 0 & 0 \\ -\sin\theta_{85} & 0 & \cos\theta_{85} & 0 \\ 0 & 0 & 0 & 1 \end{bmatrix}$$

$$\begin{bmatrix} 1 & 0 & 0 & 0 \\ 0 & \cos\psi_{85} & -\sin\psi_{85} & 0 \\ 0 & \sin\psi_{85} & \cos\psi_{85} & 0 \\ 0 & 0 & 0 & 1 \end{bmatrix}$$

$$A_{85} = \begin{bmatrix} \cos\theta_{85} & -\sin\theta_{85}\cos\alpha_{85} & \sin\theta_{85}\sin\alpha_{85} & a_{85}\cos\theta_{85} \\ \sin\theta_{85} & \cos\theta_{85}\cos\alpha_{85} & -\cos\theta_{85}\sin\alpha_{85} & a_{85}\sin\theta_{85} \\ 0 & \sin\alpha_{85} & \cos\alpha_{85} & d_{85} \\ 0 & 0 & 0 & 1 \end{bmatrix}$$

Joint 86 connects the $1^{st}$ Cervical Vertebra to the $2^{nd}$ Cervical Vertebra. This is also termed the Axis. 50% of the rotation enabled by the C0 through C7 vertebra is realized by this joint alone. The range of rotation is 50 degrees to each side. The $d_{86}$ link length of the C1 vertebra runs collinear with the C1 vertebra running from the top of the C2 vertebra to the base of the C1 vertebra along the X axis.

$$A_{86} = \begin{bmatrix} \cos\varphi_{86} & -\sin\varphi_{86} & 0 & 0 \\ \sin\varphi_{86} & \cos\varphi_{86} & 0 & 0 \\ 0 & 0 & 1 & d_{86} \\ 0 & 0 & 0 & 1 \end{bmatrix} \begin{bmatrix} \cos\theta_{86} & 0 & \sin\theta_{86} & 0 \\ 0 & 1 & 0 & 0 \\ -\sin\theta_{86} & 0 & \cos\theta_{86} & 0 \\ 0 & 0 & 0 & 1 \end{bmatrix}$$

$$\begin{bmatrix} 1 & 0 & 0 & 0 \\ 0 & \cos\psi_{86} & -\sin\psi_{86} & 0 \\ 0 & \sin\psi_{86} & \cos\psi_{86} & 0 \\ 0 & 0 & 0 & 1 \end{bmatrix}$$

$$A_{86} = \begin{bmatrix} \cos\theta_{86} & -\sin\theta_{86}\cos\alpha_{86} & \sin\theta_{86}\sin\alpha_{86} & a_{86}\cos\theta_{86} \\ \sin\theta_{86} & \cos\theta_{86}\cos\alpha_{86} & -\cos\theta_{86}\sin\alpha_{86} & a_{86}\sin\theta_{86} \\ 0 & \sin\alpha_{86} & \cos\alpha_{86} & d_{86} \\ 0 & 0 & 0 & 1 \end{bmatrix}$$

Joint 87 connects the $2^{nd}$ Cervical Vertebra to the $3^{rd}$ Cervical Vertebra. The C2-C3 joint provides movement of the chin toward the chest (flexion) and the backward movement of the head (extension). The $d_{87}$ link length of the C2 vertebra runs collinear with the C2 vertebra running from the top of the C3 vertebra to the base of the C2 vertebra along the X axis.

$$A_{87} = \begin{bmatrix} \cos\varphi_{87} & -\sin\varphi_{87} & 0 & 0 \\ \sin\varphi_{87} & \cos\varphi_{87} & 0 & 0 \\ 0 & 0 & 1 & d_{87} \\ 0 & 0 & 0 & 1 \end{bmatrix} \begin{bmatrix} \cos\theta_{87} & 0 & \sin\theta_{87} & 0 \\ 0 & 1 & 0 & 0 \\ -\sin\theta_{87} & 0 & \cos\theta_{87} & 0 \\ 0 & 0 & 0 & 1 \end{bmatrix}$$

$$\begin{bmatrix} 1 & 0 & 0 & 0 \\ 0 & \cos\psi_{87} & -\sin\varphi_{87} & 0 \\ 0 & \sin\varphi_{87} & \cos\varphi_{87} & 0 \\ 0 & 0 & 0 & 1 \end{bmatrix}$$

$$A_{87} = \begin{bmatrix} \cos\theta_{87} & -\sin\theta_{87}\cos\alpha_{87} & \sin\theta_{87}\sin\alpha_{87} & a_{87}\cos\theta_{87} \\ \sin\theta_{87} & \cos\theta_{87}\cos\alpha_{87} & -\cos\theta_{87}\sin\alpha_{87} & a_{87}\sin\theta_{87} \\ 0 & \sin\alpha_{87} & \cos\alpha_{87} & d_{87} \\ 0 & 0 & 0 & 1 \end{bmatrix}$$

Joint 88 connects the 3$^{rd}$ Cervical Vertebra to the 4$^{th}$ Cervical Vertebra. The $d_{88}$ link length of the C3 vertebra runs collinear with the C3 vertebra running from the head of the C4 vertebra to the base of the C3 vertebra along the X axis.

$$A_{88} = \begin{bmatrix} \cos\varphi_{88} & -\sin\varphi_{88} & 0 & 0 \\ \sin\varphi_{88} & \cos\varphi_{88} & 0 & 0 \\ 0 & 0 & 1 & d_{88} \\ 0 & 0 & 0 & 1 \end{bmatrix} \begin{bmatrix} \cos\theta_{88} & 0 & \sin\theta_{88} & 0 \\ 0 & 1 & 0 & 0 \\ -\sin\theta_{88} & 0 & \cos\theta_{88} & 0 \\ 0 & 0 & 0 & 1 \end{bmatrix}$$

$$\begin{bmatrix} 1 & 0 & 0 & 0 \\ 0 & \cos\psi_{88} & -\sin\varphi_{88} & 0 \\ 0 & \sin\varphi_{88} & \cos\varphi_{88} & 0 \\ 0 & 0 & 0 & 1 \end{bmatrix}$$

$$A_{88} = \begin{bmatrix} \cos\theta_{88} & -\sin\theta_{88}\cos\alpha_{88} & \sin\theta_{88}\sin\alpha_{88} & a_{88}\cos\theta_{88} \\ \sin\theta_{88} & \cos\theta_{88}\cos\alpha_{88} & -\cos\theta_{88}\sin\alpha_{88} & a_{88}\sin\theta_{88} \\ 0 & \sin\alpha_{88} & \cos\alpha_{88} & d_{88} \\ 0 & 0 & 0 & 1 \end{bmatrix}$$

Joint 89 connects the 4$^{th}$ cervical vertebra to the 5$^{th}$ cervical vertebra. The $d_{89}$ link length of the C3 vertebra runs collinear with the C0 vertebra running from the head of the C5 vertebra to the base of the C4 vertebra along the X axis.

$$A_{89} = \begin{bmatrix} \cos\varphi_{89} & -\sin\varphi_{89} & 0 & 0 \\ \sin\varphi_{89} & \cos\varphi_{89} & 0 & 0 \\ 0 & 0 & 1 & d_{89} \\ 0 & 0 & 0 & 1 \end{bmatrix} \begin{bmatrix} \cos\theta_{89} & 0 & \sin\theta_{89} & 0 \\ 0 & 1 & 0 & 0 \\ -\sin\theta_{89} & 0 & \cos\theta_{89} & 0 \\ 0 & 0 & 0 & 1 \end{bmatrix}$$

$$\begin{bmatrix} 1 & 0 & 0 & 0 \\ 0 & \cos\psi_{89} & -\sin\varphi_{89} & 0 \\ 0 & \sin\varphi_{89} & \cos\varphi_{89} & 0 \\ 0 & 0 & 0 & 1 \end{bmatrix}$$

$$A_{89} = \begin{bmatrix} \cos\theta_{89} & -\sin\theta_{89}\cos\alpha_{89} & \sin\theta_{89}\sin\alpha_{89} & a_{89}\cos\theta_{89} \\ \sin\theta_{89} & \cos\theta_{89}\cos\alpha_{89} & -\cos\theta_{89}\sin\alpha_{89} & a_{89}\sin\theta_{89} \\ 0 & \sin\alpha_{89} & \cos\alpha_{89} & d_{89} \\ 0 & 0 & 0 & 1 \end{bmatrix}$$

Joint 90 connects the 5$^{th}$ Cervical Vertebra to the 6$^{th}$ Cervical Vertebra. The $d_{90}$ link length of the C5 vertebra runs collinear with the C5 vertebra running from the head of the C6 vertebra to the base of the C5 vertebra along the X axis.

$$A_{90} = \begin{bmatrix} \cos\varphi_{90} & -\sin\varphi_{90} & 0 & 0 \\ \sin\varphi_{90} & \cos\varphi_{90} & 0 & 0 \\ 0 & 0 & 1 & d_{90} \\ 0 & 0 & 0 & 1 \end{bmatrix} \begin{bmatrix} \cos\theta_{90} & 0 & \sin\theta_{90} & 0 \\ 0 & 1 & 0 & 0 \\ -\sin\theta_{90} & 0 & \cos\theta_{90} & 0 \\ 0 & 0 & 0 & 1 \end{bmatrix}$$

$$\begin{bmatrix} 1 & 0 & 0 & 0 \\ 0 & \cos\psi_{90} & -\sin\varphi_{90} & 0 \\ 0 & \sin\varphi_{90} & \cos\varphi_{90} & 0 \\ 0 & 0 & 0 & 1 \end{bmatrix}$$

$$A_{90} = \begin{bmatrix} \cos\theta_{90} & -\sin\theta_{90}\cos\alpha_{90} & \sin\theta_{90}\sin\alpha_{90} & a_{90}\cos\theta_{90} \\ \sin\theta_{90} & \cos\theta_{90}\cos\alpha_{90} & -\cos\theta_{90}\sin\alpha_{90} & a_{90}\sin\theta_{90} \\ 0 & \sin\alpha_{90} & \cos\alpha_{90} & d_{90} \\ 0 & 0 & 0 & 1 \end{bmatrix}$$

Joint 91 connects the 6th Cervical Vertebra to the 7th Cervical Vertebra. The $d_{91}$ link length of the C6 vertebra runs collinear with the C6 vertebra running from the head of the C7 vertebra to the base of the C6 vertebra along the X axis.

$$A_{91} = \begin{bmatrix} \cos\varphi_{91} & -\sin\varphi_{91} & 0 & 0 \\ \sin\varphi_{91} & \cos\varphi_{91} & 0 & 0 \\ 0 & 0 & 1 & d_{91} \\ 0 & 0 & 0 & 1 \end{bmatrix} \begin{bmatrix} \cos\theta_{91} & 0 & \sin\theta_{91} & 0 \\ 0 & 1 & 0 & 0 \\ -\sin\theta_{91} & 0 & \cos\theta_{91} & 0 \\ 0 & 0 & 0 & 1 \end{bmatrix}$$

$$\begin{bmatrix} 1 & 0 & 0 & 0 \\ 0 & \cos\psi_{91} & -\sin\varphi_{91} & 0 \\ 0 & \sin\varphi_{91} & \cos\varphi_{91} & 0 \\ 0 & 0 & 0 & 1 \end{bmatrix}$$

$$A_{91} = \begin{bmatrix} \cos\theta_{91} & -\sin\theta_{91}\cos\alpha_{91} & \sin\theta_{91}\sin\alpha_{91} & a_{91}\cos\theta_{91} \\ \sin\theta_{91} & \cos\theta_{91}\cos\alpha_{91} & -\cos\theta_{91}\sin\alpha_{91} & a_{91}\sin\theta_{91} \\ 0 & \sin\alpha_{91} & \cos\alpha_{91} & d_{91} \\ 0 & 0 & 0 & 1 \end{bmatrix}$$

Joint 92 connects the 7$^{th}$ cervical vertebra to the 1$^{st}$ thoracic vertebra. The $d_{92}$ link length of the C7 vertebra runs collinear with the C7 vertebra running from the head of the T1 vertebra to the base of the C7 vertebra along the X axis.

$$A_{92} = \begin{bmatrix} \cos\varphi_{92} & -\sin\varphi_{92} & 0 & 0 \\ \sin\varphi_{92} & \cos\varphi_{92} & 0 & 0 \\ 0 & 0 & 1 & d_{92} \\ 0 & 0 & 0 & 1 \end{bmatrix} \begin{bmatrix} \cos\theta_{92} & 0 & \sin\theta_{92} & 0 \\ 0 & 1 & 0 & 0 \\ -\sin\theta_{92} & 0 & \cos\theta_{92} & 0 \\ 0 & 0 & 0 & 1 \end{bmatrix}$$

$$\begin{bmatrix} 1 & 0 & 0 & 0 \\ 0 & \cos\psi_{92} & -\sin\varphi_{92} & 0 \\ 0 & \sin\varphi_{92} & \cos\varphi_{92} & 0 \\ 0 & 0 & 0 & 1 \end{bmatrix}$$

$$A_{92} = \begin{bmatrix} \cos\theta_{92} & -\sin\theta_{92}\cos\alpha_{92} & \sin\theta_{92}\sin\alpha_{92} & a_{92}\cos\theta_{92} \\ \sin\theta_{92} & \cos\theta_{92}\cos\alpha_{92} & -\cos\theta_{92}\sin\alpha_{92} & a_{92}\sin\theta_{92} \\ 0 & \sin\alpha_{92} & \cos\alpha_{92} & d_{92} \\ 0 & 0 & 0 & 1 \end{bmatrix}$$

Joint 93 connects the 1$^{st}$ Thoracic Vertebra to the 2nd Thoracic Vertebra. The d$_{93}$ link length of the T1 vertebra runs collinear with the T1 vertebra running from the head of the T2 vertebra to the base of the T1 vertebra along the X axis.

$$A_{93} = \begin{bmatrix} \cos\varphi_{93} & -\sin\varphi_{93} & 0 & 0 \\ \sin\varphi_{93} & \cos\varphi_{93} & 0 & 0 \\ 0 & 0 & 1 & d_{93} \\ 0 & 0 & 0 & 1 \end{bmatrix} \begin{bmatrix} \cos\theta_{93} & 0 & \sin\theta_{93} & 0 \\ 0 & 1 & 0 & 0 \\ -\sin\theta_{93} & 0 & \cos\theta_{93} & 0 \\ 0 & 0 & 0 & 1 \end{bmatrix}$$

$$\begin{bmatrix} 1 & 0 & 0 & 0 \\ 0 & \cos\psi_{93} & -\sin\varphi_{93} & 0 \\ 0 & \sin\varphi_{93} & \cos\varphi_{93} & 0 \\ 0 & 0 & 0 & 1 \end{bmatrix}$$

$$A_{93} = \begin{bmatrix} \cos\theta_{93} & -\sin\theta_{93}\cos\alpha_{93} & \sin\theta_{93}\sin\alpha_{93} & a_{93}\cos\theta_{93} \\ \sin\theta_{93} & \cos\theta_{93}\cos\alpha_{93} & -\cos\theta_{93}\sin\alpha_{93} & a_{93}\sin\theta_{93} \\ 0 & \sin\alpha_{93} & \cos\alpha_{93} & d_{93} \\ 0 & 0 & 0 & 1 \end{bmatrix}$$

Joint 94 connects the 2$^{nd}$ Thoracic Vertebra to the 3rd Thoracic Vertebra. The d$_{94}$ link length of the T2 vertebra runs collinear with the T2 vertebra running from the head of the T3 vertebra to the base of the T2 vertebra along the X axis.

$$A_{94} = \begin{bmatrix} \cos\varphi_{94} & -\sin\varphi_{94} & 0 & 0 \\ \sin\varphi_{94} & \cos\varphi_{94} & 0 & 0 \\ 0 & 0 & 1 & d_{94} \\ 0 & 0 & 0 & 1 \end{bmatrix} \begin{bmatrix} \cos\theta_{94} & 0 & \sin\theta_{94} & 0 \\ 0 & 1 & 0 & 0 \\ -\sin\theta_{94} & 0 & \cos\theta_{94} & 0 \\ 0 & 0 & 0 & 1 \end{bmatrix}$$

$$\begin{bmatrix} 1 & 0 & 0 & 0 \\ 0 & \cos\psi_{94} & -\sin\varphi_{94} & 0 \\ 0 & \sin\varphi_{94} & \cos\varphi_{94} & 0 \\ 0 & 0 & 0 & 1 \end{bmatrix}$$

$$A_{94} = \begin{bmatrix} \cos\theta_{94} & -\sin\theta_{94}\cos\alpha_{94} & \sin\theta_{94}\sin\alpha_{94} & a_{94}\cos\theta_{94} \\ \sin\theta_{94} & \cos\theta_{94}\cos\alpha_{94} & -\cos\theta_{94}\sin\alpha_{94} & a_{94}\sin\theta_{94} \\ 0 & \sin\alpha_{94} & \cos\alpha_{94} & d_{94} \\ 0 & 0 & 0 & 1 \end{bmatrix}$$

Joint 95 connects the 3$^{rd}$ Thoracic Vertebra to the 4th Thoracic Vertebra. The d$_{95}$ link length of the T3 vertebra runs collinear with the T3 vertebra running from the head of the T4 vertebra to the base of the T3 vertebra along the X axis.

$$A_{95} = \begin{bmatrix} \cos\varphi_{95} & -\sin\varphi_{95} & 0 & 0 \\ \sin\varphi_{95} & \cos\varphi_{95} & 0 & 0 \\ 0 & 0 & 1 & d_{95} \\ 0 & 0 & 0 & 1 \end{bmatrix} \begin{bmatrix} \cos\theta_{95} & 0 & \sin\theta_{95} & 0 \\ 0 & 1 & 0 & 0 \\ -\sin\theta_{95} & 0 & \cos\theta_{95} & 0 \\ 0 & 0 & 0 & 1 \end{bmatrix}$$

$$\begin{bmatrix} 1 & 0 & 0 & 0 \\ 0 & \cos\psi_{95} & -\sin\varphi_{95} & 0 \\ 0 & \sin\varphi_{95} & \cos\varphi_{95} & 0 \\ 0 & 0 & 0 & 1 \end{bmatrix}$$

$$A_{95} = \begin{bmatrix} \cos\theta_{95} & -\sin\theta_{95}\cos\alpha_{95} & \sin\theta_{95}\sin\alpha_{95} & a_{95}\cos\theta_{95} \\ \sin\theta_{95} & \cos\theta_{95}\cos\alpha_{95} & -\cos\theta_{95}\sin\alpha_{95} & a_{95}\sin\theta_{95} \\ 0 & \sin\alpha_{95} & \cos\alpha_{95} & d_{95} \\ 0 & 0 & 0 & 1 \end{bmatrix}$$

Joint 96 connects the 4$^{th}$ thoracic vertebra to the 5$^{th}$ thoracic vertebra. The d$_{96}$ link length of the T4 vertebra runs collinear with the T4 vertebra running from the head of the T5 vertebra to the base of the T4 vertebra along the X axis.

$$A_{96} = \begin{bmatrix} \cos\varphi_{96} & -\sin\varphi_{96} & 0 & 0 \\ \sin\varphi_{96} & \cos\varphi_{96} & 0 & 0 \\ 0 & 0 & 1 & d_{96} \\ 0 & 0 & 0 & 1 \end{bmatrix} \begin{bmatrix} \cos\varphi_{96} & 0 & \sin\varphi_{96} & 0 \\ 0 & 1 & 0 & 0 \\ -\sin\varphi_{96} & 0 & \cos\varphi_{96} & 0 \\ 0 & 0 & 0 & 1 \end{bmatrix}$$

$$\begin{bmatrix} 1 & 0 & 0 & 0 \\ 0 & \cos\psi_{96} & -\sin\varphi_{96} & 0 \\ 0 & \sin\varphi_{96} & \cos\varphi_{96} & 0 \\ 0 & 0 & 0 & 1 \end{bmatrix}$$

$$A_{96} = \begin{bmatrix} \cos\theta_{96} & -\sin\theta_{96}\cos\alpha_{96} & \sin\theta_{96}\sin\alpha_{96} & a_{96}\cos\theta_{96} \\ \sin\theta_{96} & \cos\theta_{96}\cos\alpha_{96} & -\cos\theta_{96}\sin\alpha_{96} & a_{96}\sin\theta_{96} \\ 0 & \sin\alpha_{96} & \cos\alpha_{96} & d_{96} \\ 0 & 0 & 0 & 1 \end{bmatrix}$$

Joint 97 connects the 5$^{th}$ Thoracic Vertebra to the 6$^{th}$ Thoracic Vertebra. The d$_{97}$ link length of the T5 vertebra runs collinear with the T5 vertebra running from the head of the T6 vertebra to the base of the T5 vertebra along the X axis.

$$A_{97} = \begin{bmatrix} \cos\varphi_{97} & -\sin\varphi_{97} & 0 & 0 \\ \sin\varphi_{97} & \cos\varphi_{97} & 0 & 0 \\ 0 & 0 & 1 & d_{97} \\ 0 & 0 & 0 & 1 \end{bmatrix} \begin{bmatrix} \cos\varphi_{97} & 0 & \sin\varphi_{97} & 0 \\ 0 & 1 & 0 & 0 \\ -\sin\varphi_{97} & 0 & \cos\varphi_{97} & 0 \\ 0 & 0 & 0 & 1 \end{bmatrix}$$

$$\begin{bmatrix} 1 & 0 & 0 & 0 \\ 0 & \cos\psi_{97} & -\sin\varphi_{97} & 0 \\ 0 & \sin\varphi_{97} & \cos\varphi_{97} & 0 \\ 0 & 0 & 0 & 1 \end{bmatrix}$$

$$A_{97} = \begin{bmatrix} \cos\theta_{97} & -\sin\theta_{97}\cos\alpha_{97} & \sin\theta_{97}\sin\alpha_{97} & a_{96}\cos\theta_{97} \\ \sin\theta_{97} & \cos\theta_{97}\cos\alpha_{97} & -\cos\theta_{97}\sin\alpha_{97} & a_{96}\sin\theta_{97} \\ 0 & \sin\alpha_{96} & \cos\alpha_{97} & d_{97} \\ 0 & 0 & 0 & 1 \end{bmatrix}$$

Joint 98 connects the 6$^{th}$ Thoracic Vertebra to the 7$^{th}$ Thoracic Vertebra. The d$_{98}$ link length of the T6 vertebra runs collinear with the T6 vertebra running from the head of the T7 vertebra to the base of the T6 vertebra along the X axis.

$$A_{98} = \begin{bmatrix} \cos\varphi_{98} & -\sin\varphi_{98} & 0 & 0 \\ \sin\varphi_{98} & \cos\varphi_{98} & 0 & 0 \\ 0 & 0 & 1 & d_{98} \\ 0 & 0 & 0 & 1 \end{bmatrix} \begin{bmatrix} \cos\varphi_{98} & 0 & \sin\varphi_{98} & 0 \\ 0 & 1 & 0 & 0 \\ -\sin\varphi_{98} & 0 & \cos\varphi_{98} & 0 \\ 0 & 0 & 0 & 1 \end{bmatrix}$$

-continued $$\begin{bmatrix} 1 & 0 & 0 & 0 \\ 0 & \cos\psi_{98} & -\sin\varphi_{98} & 0 \\ 0 & \sin\varphi_{98} & \cos\varphi_{98} & 0 \\ 0 & 0 & 0 & 1 \end{bmatrix}$$

$$A_{98} = \begin{bmatrix} \cos\theta_{98} & -\sin\theta_{98}\cos\alpha_{98} & \sin\theta_{98}\sin\alpha_{98} & a_{98}\cos\theta_{98} \\ \sin\theta_{98} & \cos\theta_{98}\cos\alpha_{98} & -\cos\theta_{98}\sin\alpha_{98} & a_{98}\sin\theta_{98} \\ 0 & \sin\alpha_{98} & \cos\alpha_{98} & d_{98} \\ 0 & 0 & 0 & 1 \end{bmatrix}$$

Joint 99 connects the $7^{th}$ Thoracic Vertebra to the $8^{th}$ Thoracic Vertebra. The $d_{99}$ link length of the T7 vertebra runs collinear with the T7 vertebra running from the head of the T8 vertebra to the base of the T7 vertebra along the X axis.

$$A_{99} = \begin{bmatrix} \cos\varphi_{99} & -\sin\varphi_{99} & 0 & 0 \\ \sin\varphi_{99} & \cos\varphi_{99} & 0 & 0 \\ 0 & 0 & 1 & d_{99} \\ 0 & 0 & 0 & 1 \end{bmatrix} \begin{bmatrix} \cos\varphi_{99} & 0 & \sin\varphi_{99} & 0 \\ 0 & 1 & 0 & 0 \\ -\sin\varphi_{99} & 0 & \cos\varphi_{99} & 0 \\ 0 & 0 & 0 & 1 \end{bmatrix}$$

$$\begin{bmatrix} 1 & 0 & 0 & 0 \\ 0 & \cos\psi_{99} & -\sin\varphi_{99} & 0 \\ 0 & \sin\varphi_{99} & \cos\varphi_{99} & 0 \\ 0 & 0 & 0 & 1 \end{bmatrix}$$

$$A_{99} = \begin{bmatrix} \cos\theta_{99} & -\sin\theta_{99}\cos\alpha_{99} & \sin\theta_{99}\sin\alpha_{99} & a_{99}\cos\theta_{99} \\ \sin\theta_{99} & \cos\theta_{99}\cos\alpha_{99} & -\cos\theta_{99}\sin\alpha_{99} & a_{99}\sin\theta_{99} \\ 0 & \sin\alpha_{99} & \cos\alpha_{99} & d_{99} \\ 0 & 0 & 0 & 1 \end{bmatrix}$$

Joint 100 connects the $8^{th}$ Thoracic Vertebra to the $9^{th}$ Thoracic Vertebra. The $d_{100}$ link length of the T8 vertebra runs collinear with the T8 vertebra running from the head of the T9 vertebra to the base of the T8 vertebra along the X axis.

$$A_{100} = \begin{bmatrix} \cos\varphi_{100} & -\sin\varphi_{100} & 0 & 0 \\ \sin\varphi_{100} & \cos\varphi_{100} & 0 & 0 \\ 0 & 0 & 1 & d_{100} \\ 0 & 0 & 0 & 1 \end{bmatrix} \begin{bmatrix} \cos\varphi_{100} & 0 & \sin\varphi_{100} & 0 \\ 0 & 1 & 0 & 0 \\ -\sin\varphi_{100} & 0 & \cos\varphi_{100} & 0 \\ 0 & 0 & 0 & 1 \end{bmatrix}$$

$$\begin{bmatrix} 1 & 0 & 0 & 0 \\ 0 & \cos\psi_{100} & -\sin\varphi_{100} & 0 \\ 0 & \sin\varphi_{100} & \cos\varphi_{100} & 0 \\ 0 & 0 & 0 & 1 \end{bmatrix}$$

$$A_{100} = \begin{bmatrix} \cos\theta_{100} & -\sin\theta_{100}\cos\alpha_{100} & \sin\theta_{100}\sin\alpha_{100} & a_{100}\cos\theta_{100} \\ \sin\theta_{100} & \cos\theta_{100}\cos\alpha_{100} & -\cos\theta_{100}\sin\alpha_{100} & a_{100}\sin\theta_{100} \\ 0 & \sin\alpha_{100} & \cos\alpha_{100} & d_{100} \\ 0 & 0 & 0 & 1 \end{bmatrix}$$

Joint 101 connects the $9^{th}$ Thoracic Vertebra to the $10^{th}$ Thoracic Vertebra. The $d_{101}$ link length of the T8 vertebra runs collinear with the T8 vertebra running from the head of the T9 vertebra to the base of the T8 vertebra along the X axis.

$$A_{101} = \begin{bmatrix} \cos\varphi_{101} & -\sin\varphi_{101} & 0 & 0 \\ \sin\varphi_{101} & \cos\varphi_{101} & 0 & 0 \\ 0 & 0 & 1 & d_{101} \\ 0 & 0 & 0 & 1 \end{bmatrix} \begin{bmatrix} \cos\varphi_{101} & 0 & \sin\varphi_{101} & 0 \\ 0 & 1 & 0 & 0 \\ -\sin\varphi_{101} & 0 & \cos\varphi_{101} & 0 \\ 0 & 0 & 0 & 1 \end{bmatrix}$$

$$\begin{bmatrix} 1 & 0 & 0 & 0 \\ 0 & \cos\psi_{101} & -\sin\varphi_{101} & 0 \\ 0 & \sin\varphi_{101} & \cos\varphi_{101} & 0 \\ 0 & 0 & 0 & 1 \end{bmatrix}$$

$$A_{101} = \begin{bmatrix} \cos\theta_{101} & -\sin\theta_{101}\cos\alpha_{101} & \sin\theta_{101}\sin\alpha_{101} & a_{101}\cos\theta_{101} \\ \sin\theta_{101} & \cos\theta_{101}\cos\alpha_{101} & -\cos\theta_{101}\sin\alpha_{101} & a_{101}\sin\theta_{101} \\ 0 & \sin\alpha_{101} & \cos\alpha_{101} & d_{101} \\ 0 & 0 & 0 & 1 \end{bmatrix}$$

Joint 102 connects the 10th Thoracic Vertebra to the $11^{th}$ Thoracic Vertebra. The $d_{98}$ link length of the T10 vertebra runs collinear with the T10 vertebra running from the head of the T11 vertebra to the base of the T10 vertebra along the X axis.

$$A_{102} = \begin{bmatrix} \cos\varphi_{102} & -\sin\varphi_{102} & 0 & 0 \\ \sin\varphi_{102} & \cos\varphi_{102} & 0 & 0 \\ 0 & 0 & 1 & d_{102} \\ 0 & 0 & 0 & 1 \end{bmatrix} \begin{bmatrix} \cos\varphi_{102} & 0 & \sin\varphi_{102} & 0 \\ 0 & 1 & 0 & 0 \\ -\sin\varphi_{102} & 0 & \cos\varphi_{102} & 0 \\ 0 & 0 & 0 & 1 \end{bmatrix}$$

$$\begin{bmatrix} 1 & 0 & 0 & 0 \\ 0 & \cos\psi_{102} & -\sin\varphi_{102} & 0 \\ 0 & \sin\varphi_{102} & \cos\varphi_{102} & 0 \\ 0 & 0 & 0 & 1 \end{bmatrix}$$

$$A_{102} = \begin{bmatrix} \cos\theta_{102} & -\sin\theta_{102}\cos\alpha_{102} & \sin\theta_{102}\sin\alpha_{102} & a_{102}\cos\theta_{102} \\ \sin\theta_{102} & \cos\theta_{102}\cos\alpha_{102} & -\cos\theta_{102}\sin\alpha_{102} & a_{102}\sin\theta_{102} \\ 0 & \sin\alpha_{102} & \cos\alpha_{102} & d_{102} \\ 0 & 0 & 0 & 1 \end{bmatrix}$$

Joint 103 connects the 11th Thoracic Vertebra to the $12^{th}$ Thoracic Vertebra. The $d_{103}$ link length of the T11 vertebra runs collinear with the T11 vertebra running from the head of the T12 vertebra to the base of the T11 vertebra along the X axis.

$$A_{103} = \begin{bmatrix} \cos\varphi_{103} & -\sin\varphi_{103} & 0 & 0 \\ \sin\varphi_{103} & \cos\varphi_{103} & 0 & 0 \\ 0 & 0 & 1 & d_{103} \\ 0 & 0 & 0 & 1 \end{bmatrix} \begin{bmatrix} \cos\varphi_{103} & 0 & \sin\varphi_{103} & 0 \\ 0 & 1 & 0 & 0 \\ -\sin\varphi_{103} & 0 & \cos\varphi_{103} & 0 \\ 0 & 0 & 0 & 1 \end{bmatrix}$$

$$\begin{bmatrix} 1 & 0 & 0 & 0 \\ 0 & \cos\psi_{103} & -\sin\varphi_{103} & 0 \\ 0 & \sin\varphi_{103} & \cos\varphi_{103} & 0 \\ 0 & 0 & 0 & 1 \end{bmatrix}$$

$$A_{103} = \begin{bmatrix} \cos\theta_{103} & -\sin\theta_{103}\cos\alpha_{103} & \sin\theta_{103}\sin\alpha_{103} & a_{103}\cos\theta_{103} \\ \sin\theta_{103} & \cos\theta_{103}\cos\alpha_{103} & -\cos\theta_{103}\sin\alpha_{103} & a_{103}\sin\theta_{103} \\ 0 & \sin\alpha_{103} & \cos\alpha_{103} & d_{103} \\ 0 & 0 & 0 & 1 \end{bmatrix}$$

Joint 104 connects the 12th Thoracic Vertebra to the $1^{st}$ Lumbar Vertebra. The $d_{104}$ link length of the T12 vertebra runs collinear with the T12 vertebra running from the head of the T12 vertebra to the base of the L1 vertebra along the X axis.

$$A_{104} = \begin{bmatrix} \cos\varphi_{104} & -\sin\varphi_{104} & 0 & 0 \\ \sin\varphi_{104} & \cos\varphi_{104} & 0 & 0 \\ 0 & 0 & 1 & d_{104} \\ 0 & 0 & 0 & 1 \end{bmatrix} \begin{bmatrix} \cos\varphi_{104} & 0 & \sin\varphi_{104} & 0 \\ 0 & 1 & 0 & 0 \\ -\sin\varphi_{104} & 0 & \cos\varphi_{104} & 0 \\ 0 & 0 & 0 & 1 \end{bmatrix}$$

$$\begin{bmatrix} 1 & 0 & 0 & 0 \\ 0 & \cos\psi_{104} & -\sin\varphi_{104} & 0 \\ 0 & \sin\varphi_{104} & \cos\varphi_{104} & 0 \\ 0 & 0 & 0 & 1 \end{bmatrix}$$

$$A_{104} = \begin{bmatrix} \cos\theta_{104} & -\sin\theta_{104}\cos\alpha_{104} & \sin\theta_{104}\sin\alpha_{104} & a_{104}\cos\theta_{104} \\ \sin\theta_{104} & \cos\theta_{104}\cos\alpha_{104} & -\cos\theta_{104}\sin\alpha_{104} & a_{104}\sin\theta_{104} \\ 0 & \sin\alpha_{104} & \cos\alpha_{104} & d_{104} \\ 0 & 0 & 0 & 1 \end{bmatrix}$$

Joint 105 connects the 1st lumbar vertebra to the $2^{nd}$ lumbar vertebra. The $d_{105}$ link length of the L2 vertebra runs collinear with the L2 vertebra running from the head of the L2 vertebra to the base of the L1 vertebra along the X axis.

$$A_{105} = \begin{bmatrix} \cos\varphi_{105} & -\sin\varphi_{105} & 0 & 0 \\ \sin\varphi_{105} & \cos\varphi_{105} & 0 & 0 \\ 0 & 0 & 1 & d_{105} \\ 0 & 0 & 0 & 1 \end{bmatrix} \begin{bmatrix} \cos\varphi_{105} & 0 & \sin\varphi_{105} & 0 \\ 0 & 1 & 0 & 0 \\ -\sin\varphi_{105} & 0 & \cos\varphi_{105} & 0 \\ 0 & 0 & 0 & 1 \end{bmatrix}$$

$$\begin{bmatrix} 1 & 0 & 0 & 0 \\ 0 & \cos\psi_{105} & -\sin\varphi_{105} & 0 \\ 0 & \sin\varphi_{105} & \cos\varphi_{105} & 0 \\ 0 & 0 & 0 & 1 \end{bmatrix}$$

$$A_{105} = \begin{bmatrix} \cos\theta_{105} & -\sin\theta_{105}\cos\alpha_{105} & \sin\theta_{105}\sin\alpha_{105} & a_{105}\cos\theta_{105} \\ \sin\theta_{105} & \cos\theta_{105}\cos\alpha_{105} & -\cos\theta_{105}\sin\alpha_{105} & a_{105}\sin\theta_{105} \\ 0 & \sin\alpha_{105} & \cos\alpha_{105} & d_{105} \\ 0 & 0 & 0 & 1 \end{bmatrix}$$

Joint 106 connects the $2^{nd}$ Lumbar Vertebra to the $3^{rd}$ Lumbar Vertebra. The $d_{106}$ link length of the L2 vertebra runs collinear with the L2 vertebra running from the head of the L3 vertebra to the base of the L2 vertebra along the X axis.

$$A_{106} = \begin{bmatrix} \cos\varphi_{106} & -\sin\varphi_{106} & 0 & 0 \\ \sin\varphi_{106} & \cos\varphi_{106} & 0 & 0 \\ 0 & 0 & 1 & d_{106} \\ 0 & 0 & 0 & 1 \end{bmatrix} \begin{bmatrix} \cos\varphi_{106} & 0 & \sin\varphi_{106} & 0 \\ 0 & 1 & 0 & 0 \\ -\sin\varphi_{106} & 0 & \cos\varphi_{106} & 0 \\ 0 & 0 & 0 & 1 \end{bmatrix}$$

$$\begin{bmatrix} 1 & 0 & 0 & 0 \\ 0 & \cos\psi_{106} & -\sin\varphi_{106} & 0 \\ 0 & \sin\varphi_{106} & \cos\varphi_{106} & 0 \\ 0 & 0 & 0 & 1 \end{bmatrix}$$

$$A_{106} = \begin{bmatrix} \cos\theta_{106} & -\sin\theta_{106}\cos\alpha_{106} & \sin\theta_{106}\sin\alpha_{106} & a_{106}\cos\theta_{106} \\ \sin\theta_{106} & \cos\theta_{106}\cos\alpha_{106} & -\cos\theta_{106}\sin\alpha_{106} & a_{106}\sin\theta_{106} \\ 0 & \sin\alpha_{106} & \cos\alpha_{106} & d_{106} \\ 0 & 0 & 0 & 1 \end{bmatrix}$$

Joint 107 connects the $3^{rd}$ Lumbar Vertebra to the $4^{th}$ Lumbar Vertebra. The $d_{107}$ link length of the L3 vertebra runs collinear with the L3 vertebra running from the head of the L4 vertebra to the base of the L3 vertebra along the X axis.

$$A_{107} = \begin{bmatrix} \cos\varphi_{107} & -\sin\varphi_{107} & 0 & 0 \\ \sin\varphi_{107} & \cos\varphi_{107} & 0 & 0 \\ 0 & 0 & 1 & d_{107} \\ 0 & 0 & 0 & 1 \end{bmatrix} \begin{bmatrix} \cos\varphi_{107} & 0 & \sin\varphi_{107} & 0 \\ 0 & 1 & 0 & 0 \\ -\sin\varphi_{107} & 0 & \cos\varphi_{107} & 0 \\ 0 & 0 & 0 & 1 \end{bmatrix}$$

$$\begin{bmatrix} 1 & 0 & 0 & 0 \\ 0 & \cos\psi_{107} & -\sin\varphi_{107} & 0 \\ 0 & \sin\varphi_{107} & \cos\varphi_{107} & 0 \\ 0 & 0 & 0 & 1 \end{bmatrix}$$

$$A_{107} = \begin{bmatrix} \cos\theta_{107} & -\sin\theta_{107}\cos\alpha_{107} & \sin\theta_{107}\sin\alpha_{107} & a_{107}\cos\theta_{107} \\ \sin\theta_{107} & \cos\theta_{107}\cos\alpha_{107} & -\cos\theta_{107}\sin\alpha_{107} & a_{107}\sin\theta_{107} \\ 0 & \sin\alpha_{107} & \cos\alpha_{107} & d_{107} \\ 0 & 0 & 0 & 1 \end{bmatrix}$$

Joint 108 connects the $4^{th}$ Lumbar Vertebra to the $5^{th}$ Lumbar Vertebra. The $d_{108}$ link length of the L4 vertebra runs collinear with the L4 vertebra running from the head of the L5 vertebra to the base of the L4 vertebra along the X axis.

$$A_{108} = \begin{bmatrix} \cos\varphi_{108} & -\sin\varphi_{108} & 0 & 0 \\ \sin\varphi_{108} & \cos\varphi_{108} & 0 & 0 \\ 0 & 0 & 1 & d_{108} \\ 0 & 0 & 0 & 1 \end{bmatrix} \begin{bmatrix} \cos\varphi_{108} & 0 & \sin\varphi_{108} & 0 \\ 0 & 1 & 0 & 0 \\ -\sin\varphi_{108} & 0 & \cos\varphi_{108} & 0 \\ 0 & 0 & 0 & 1 \end{bmatrix}$$

$$\begin{bmatrix} 1 & 0 & 0 & 0 \\ 0 & \cos\psi_{108} & -\sin\varphi_{108} & 0 \\ 0 & \sin\varphi_{108} & \cos\varphi_{108} & 0 \\ 0 & 0 & 0 & 1 \end{bmatrix}$$

$$A_{108} = \begin{bmatrix} \cos\theta_{108} & -\sin\theta_{108}\cos\alpha_{108} & \sin\theta_{108}\sin\alpha_{108} & a_{108}\cos\theta_{108} \\ \sin\theta_{108} & \cos\theta_{108}\cos\alpha_{108} & -\cos\theta_{108}\sin\alpha_{108} & a_{108}\sin\theta_{108} \\ 0 & \sin\alpha_{108} & \cos\alpha_{108} & d_{108} \\ 0 & 0 & 0 & 1 \end{bmatrix}$$

Joint 109 connects the $5^{th}$ Lumbar Vertebra to the $2^{nd}$ Lumbar Vertebra. The $d_{109}$ link length of the L5 vertebra runs collinear with the L5 vertebra running from the head of the Si sacrum to the base of the L5 vertebra along the X axis.

$$A_{109} = \begin{bmatrix} \cos\varphi_{109} & -\sin\varphi_{109} & 0 & 0 \\ \sin\varphi_{109} & \cos\varphi_{109} & 0 & 0 \\ 0 & 0 & 1 & d_{109} \\ 0 & 0 & 0 & 1 \end{bmatrix} \begin{bmatrix} \cos\varphi_{109} & 0 & \sin\varphi_{109} & 0 \\ 0 & 1 & 0 & 0 \\ -\sin\varphi_{109} & 0 & \cos\varphi_{109} & 0 \\ 0 & 0 & 0 & 1 \end{bmatrix}$$

$$\begin{bmatrix} 1 & 0 & 0 & 0 \\ 0 & \cos\psi_{109} & -\sin\varphi_{109} & 0 \\ 0 & \sin\varphi_{109} & \cos\varphi_{109} & 0 \\ 0 & 0 & 0 & 1 \end{bmatrix}$$

$$A_{109} = \begin{bmatrix} \cos\theta_{109} & -\sin\theta_{109}\cos\alpha_{109} & \sin\theta_{109}\sin\alpha_{109} & a_{109}\cos\theta_{109} \\ \sin\theta_{109} & \cos\theta_{109}\cos\alpha_{109} & -\cos\theta_{109}\sin\alpha_{109} & a_{109}\sin\theta_{109} \\ 0 & \sin\alpha_{109} & \cos\alpha_{109} & d_{109} \\ 0 & 0 & 0 & 1 \end{bmatrix}$$

Joint 110 connects the right thumb Distal Phalanx to the right thumb Proximal Phalanx, forming the $1^{st}$ distal interphalangeal joint (DIP). The duo length of the right Distal Phalanx runs through the centroid of the Distal Phalanx from the head of the right Proximal Phalanx to the head of the right distal phalanx $$A_{110} = \begin{bmatrix} \cos\varphi_{110} & -\sin\varphi_{110} & 0 & 0 \\ \sin\varphi_{110} & \cos\varphi_{110} & 0 & 0 \\ 0 & 0 & 1 & d_{110} \\ 0 & 0 & 0 & 1 \end{bmatrix} \begin{bmatrix} \cos\varphi_{110} & 0 & \sin\varphi_{110} & 0 \\ 0 & 1 & 0 & 0 \\ -\sin\varphi_{110} & 0 & \cos\varphi_{110} & 0 \\ 0 & 0 & 0 & 1 \end{bmatrix}$$

$$\begin{bmatrix} 1 & 0 & 0 & 0 \\ 0 & \cos\psi_{110} & -\sin\varphi_{110} & 0 \\ 0 & \sin\varphi_{110} & \cos\varphi_{110} & 0 \\ 0 & 0 & 0 & 1 \end{bmatrix}$$

$$A_{110} = \begin{bmatrix} \cos\theta_{110} & -\sin\theta_{110}\cos\alpha_{110} & \sin\theta_{110}\sin\alpha_{110} & a_{110}\cos\theta_{110} \\ \sin\theta_{110} & \cos\theta_{110}\cos\alpha_{110} & -\cos\theta_{110}\sin\alpha_{110} & a_{110}\sin\theta_{110} \\ 0 & \sin\alpha_{110} & \cos\alpha_{110} & d_{110} \\ 0 & 0 & 0 & 1 \end{bmatrix}$$

Joint 111 connects the right index finger Distal Phalanx to the right index finger Middle Phalanx, forming the $2^{nd}$ distal interphalangeal joint (DIP) The $d_{ill}$ length of the right index finger Digital Phalanx runs through the centroid of the Distal Phalanx from the head of the right index finger Proximal Phalanx to the head of the right index finger Distal Phalanx.

$$A_{111} = \begin{bmatrix} \cos\theta_{111} & -\sin\theta_{111} & 0 & 0 \\ \sin\theta_{111} & \cos\theta_{111} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{111} \\ 0 & 0 & 0 & 1 \end{bmatrix} \begin{bmatrix} 1 & 0 & 0 & a_{111} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{111} & -\sin\alpha_{111} & 0 \\ 0 & \sin\alpha_{111} & \cos\alpha_{111} & 0 \\ 0 & 0 & 0 & 1 \end{bmatrix}$$

$$A_{111} = \begin{bmatrix} \cos\theta_{111} & -\sin\theta_{111}\cos\alpha_{111} & \sin\theta_{111}\sin\alpha_{111} & a_{111}\cos\theta_{111} \\ \sin\theta_{111} & \cos\theta_{111}\cos\alpha_{111} & -\cos\theta_{111}\sin\alpha_{111} & a_{111}\sin\theta_{111} \\ 0 & \sin\alpha_{111} & \cos\alpha_{111} & d_{111} \\ 0 & 0 & 0 & 1 \end{bmatrix}$$

Joint 112 connects the right middle finger Distal Phalanx to the right middle finger Middle Phalanx, forming the $3^{rd}$ distal interphalangeal joint (DIP). The $d_{112}$ length of the right middle finger Digital Phalanx runs through the centroid of the Distal Phalanx from the head of the right index finger Proximal Phalanx to the dead of the right middle finger Distal Phalanx.

$$A_{112} = \begin{bmatrix} \cos\theta_{112} & -\sin\theta_{112} & 0 & 0 \\ \sin\theta_{112} & \cos\theta_{112} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{112} \\ 0 & 0 & 0 & 1 \end{bmatrix} \begin{bmatrix} 1 & 0 & 0 & a_{112} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{112} & -\sin\alpha_{112} & 0 \\ 0 & \sin\alpha_{112} & \cos\alpha_{112} & 0 \\ 0 & 0 & 0 & 1 \end{bmatrix}$$

$$A_{112} = \begin{bmatrix} \cos\theta_{112} & -\sin\theta_{112}\cos\alpha_{112} & \sin\theta_{112}\sin\alpha_{112} & a_{112}\cos\theta_{112} \\ \sin\theta_{112} & \cos\theta_{112}\cos\alpha_{112} & -\cos\theta_{112}\sin\alpha_{112} & a_{112}\sin\theta_{112} \\ 0 & \sin\alpha_{112} & \cos\alpha_{112} & d_{112} \\ 0 & 0 & 0 & 1 \end{bmatrix}$$

Joint 113 connects the right ring finger Distal Phalanx to the right ring finger Middle Phalanx, forming the $4^{th}$ distal interphalangeal joint (DIP). The $d_{113}$ length of the right ring finger Digital Phalanx runs through the centroid of the Distal Phalanx from the head of the right ring finger Proximal Phalanx to the head of the right ring finger Distal Phalanx.

$$A_{113} = \begin{bmatrix} \cos\theta_{113} & -\sin\theta_{113} & 0 & 0 \\ \sin\theta_{113} & \cos\theta_{113} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{113} \\ 0 & 0 & 0 & 1 \end{bmatrix} \begin{bmatrix} 1 & 0 & 0 & a_{113} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{113} & -\sin\alpha_{113} & 0 \\ 0 & \sin\alpha_{113} & \cos\alpha_{113} & 0 \\ 0 & 0 & 0 & 1 \end{bmatrix}$$

$$A_{113} = \begin{bmatrix} \cos\theta_{113} & -\sin\theta_{113}\cos\alpha_{113} & \sin\theta_{113}\sin\alpha_{113} & a_{113}\cos\theta_{113} \\ \sin\theta_{113} & \cos\theta_{113}\cos\alpha_{113} & -\cos\theta_{113}\sin\alpha_{113} & a_{113}\sin\theta_{113} \\ 0 & \sin\alpha_{113} & \cos\alpha_{113} & d_{113} \\ 0 & 0 & 0 & 1 \end{bmatrix}$$

Joint 114 connects the right little finger Distal Phalanx to the right little finger Middle Phalanx, forming the $5^{th}$ distal interphalangeal joint (DIP). The $d_{114}$ length of the right little finger Digital Phalanx runs through the centroid of the Distal Phalanx from the head of the right little finger Proximal Phalanx to the head of the right little finger Distal Phalanx.

$$A_{114} = \begin{bmatrix} \cos\theta_{114} & -\sin\theta_{114} & 0 & 0 \\ \sin\theta_{114} & \cos\theta_{114} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{114} \\ 0 & 0 & 0 & 1 \end{bmatrix} \begin{bmatrix} 1 & 0 & 0 & a_{114} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{114} & -\sin\alpha_{114} & 0 \\ 0 & \sin\alpha_{114} & \cos\alpha_{114} & 0 \\ 0 & 0 & 0 & 1 \end{bmatrix}$$

$$A_{114} = \begin{bmatrix} \cos\theta_{114} & -\sin\theta_{114}\cos\alpha_{114} & \sin\theta_{114}\sin\alpha_{114} & a_{113}\cos\theta_{114} \\ \sin\theta_{114} & \cos\theta_{114}\cos\alpha_{114} & -\cos\theta_{114}\sin\alpha_{114} & a_{113}\sin\theta_{114} \\ 0 & \sin\alpha_{114} & \cos\alpha_{114} & d_{114} \\ 0 & 0 & 0 & 1 \end{bmatrix}$$

Joint 115 connects the right index finger Middle Phalanx to the right index finger Proximal Phalanx forming the $2^{nd}$ proximal interphalangeal joint (PIP). The $d_{115}$ length of the right index finger Middle Phalanx runs through the centroid of the Middle Phalanx from the head of the right index finger Proximal Phalanx to the head of the right index finger middle phalanx.

$$A_{115} = \begin{bmatrix} \cos\theta_{115} & -\sin\theta_{115} & 0 & 0 \\ \sin\theta_{115} & \cos\theta_{115} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{115} \\ 0 & 0 & 0 & 1 \end{bmatrix} \begin{bmatrix} 1 & 0 & 0 & a_{115} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{115} & -\sin\alpha_{115} & 0 \\ 0 & \sin\alpha_{115} & \cos\alpha_{115} & 0 \\ 0 & 0 & 0 & 1 \end{bmatrix}$$

$$A_{115} = \begin{bmatrix} \cos\theta_{115} & -\sin\theta_{115}\cos\alpha_{115} & \sin\theta_{115}\sin\alpha_{115} & a_{115}\cos\theta_{115} \\ \sin\theta_{115} & \cos\theta_{115}\cos\alpha_{115} & -\cos\theta_{115}\sin\alpha_{115} & a_{115}\sin\theta_{115} \\ 0 & \sin\alpha_{115} & \cos\alpha_{115} & d_{115} \\ 0 & 0 & 0 & 1 \end{bmatrix}$$

Joint 116 connects the right middle finger Middle Phalanx to the right middle finger Proximal Phalanx, forming the 3$^{rd}$ proximal interphalangeal joint (PIP).

The $d_{116}$ length of the right middle finger Middle Phalanx runs through the centroid of the Middle Phalanx from the head of the right middle finger Proximal Phalanx to the head of the right middle finger Middle Phalanx.

$$A_{116} = \begin{bmatrix} \cos\theta_{116} & -\sin\theta_{116} & 0 & 0 \\ \sin\theta_{116} & \cos\theta_{116} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{116} \\ 0 & 0 & 0 & 1 \end{bmatrix} \begin{bmatrix} 1 & 0 & 0 & a_{116} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{116} & -\sin\alpha_{116} & 0 \\ 0 & \sin\alpha_{116} & \cos\alpha_{116} & 0 \\ 0 & 0 & 0 & 1 \end{bmatrix}$$

$$A_{116} = \begin{bmatrix} \cos\theta_{116} & -\sin\theta_{116}\cos\alpha_{116} & \sin\theta_{116}\sin\alpha_{116} & a_{116}\cos\theta_{116} \\ \sin\theta_{116} & \cos\theta_{116}\cos\alpha_{116} & -\cos\theta_{116}\sin\alpha_{116} & a_{116}\sin\theta_{116} \\ 0 & \sin\alpha_{116} & \cos\alpha_{116} & d_{116} \\ 0 & 0 & 0 & 1 \end{bmatrix}$$

Joint 117 connects the right ring finger Middle Phalanx to the right ring finger Proximal Phalanx, forming the 4$^{th}$ proximal interphalangeal joint (PIP). The $d_{117}$ length of the right ring finger Middle Phalanx runs through the centroid of the Middle Phalanx from the head of the right ring finger Proximal Phalanx to the head of the right ring finger Middle Phalanx.

$$A_{117} = \begin{bmatrix} \cos\theta_{117} & -\sin\theta_{117} & 0 & 0 \\ \sin\theta_{117} & \cos\theta_{117} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{117} \\ 0 & 0 & 0 & 1 \end{bmatrix} \begin{bmatrix} 1 & 0 & 0 & a_{117} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{117} & -\sin\alpha_{117} & 0 \\ 0 & \sin\alpha_{117} & \cos\alpha_{117} & 0 \\ 0 & 0 & 0 & 1 \end{bmatrix}$$

$$A_{117} = \begin{bmatrix} \cos\theta_{117} & -\sin\theta_{117}\cos\alpha_{117} & \sin\theta_{117}\sin\alpha_{117} & a_{117}\cos\theta_{117} \\ \sin\theta_{117} & \cos\theta_{117}\cos\alpha_{117} & -\cos\theta_{117}\sin\alpha_{117} & a_{117}\sin\theta_{117} \\ 0 & \sin\alpha_{117} & \cos\alpha_{117} & d_{117} \\ 0 & 0 & 0 & 1 \end{bmatrix}$$

Joint 118 connects the right little finger Middle Phalanx to the right little finger Proximal Phalanx, forming the 5$^{th}$ proximal interphalangeal joint (PIP). The $d_{117}$ length of the right little finger Middle Phalanx runs through the centroid of the Middle Phalanx from the head of the right little finger Proximal Phalanx to the head of the right little finger Middle Phalanx.

$$A_{118} = \begin{bmatrix} \cos\theta_{118} & -\sin\theta_{118} & 0 & 0 \\ \sin\theta_{118} & \cos\theta_{118} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{118} \\ 0 & 0 & 0 & 1 \end{bmatrix} \begin{bmatrix} 1 & 0 & 0 & a_{118} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{118} & -\sin\alpha_{118} & 0 \\ 0 & \sin\alpha_{118} & \cos\alpha_{118} & 0 \\ 0 & 0 & 0 & 1 \end{bmatrix}$$

$$A_{118} = \begin{bmatrix} \cos\theta_{118} & -\sin\theta_{118}\cos\alpha_{118} & \sin\theta_{118}\sin\alpha_{118} & a_{118}\cos\theta_{118} \\ \sin\theta_{118} & \cos\theta_{118}\cos\alpha_{118} & -\cos\theta_{118}\sin\alpha_{118} & a_{118}\sin\theta_{118} \\ 0 & \sin\alpha_{118} & \cos\alpha_{118} & d_{118} \\ 0 & 0 & 0 & 1 \end{bmatrix}$$

Joint 119 connects the right thumb Proximal Phalanx to the right thumb Metacarpal in the 1$^{st}$ metacarpophalangeal joint (MCP). The $d_{119}$ length of the right thumb Middle Phalanx runs through the centroid of the Middle Proximal Phalanx from the head of the thumb Metacarpal to the head of the thumb Proximal Phalanx.

$$A_{119} = \begin{bmatrix} \cos\theta_{119} & -\sin\theta_{119} & 0 & 0 \\ \sin\theta_{119} & \cos\theta_{119} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{119} \\ 0 & 0 & 0 & 1 \end{bmatrix} \begin{bmatrix} 1 & 0 & 0 & a_{119} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{119} & -\sin\alpha_{119} & 0 \\ 0 & \sin\alpha_{119} & \cos\alpha_{119} & 0 \\ 0 & 0 & 0 & 1 \end{bmatrix}$$

$$A_{119} = \begin{bmatrix} \cos\theta_{119} & -\sin\theta_{119}\cos\alpha_{119} & \sin\theta_{119}\sin\alpha_{119} & a_{119}\cos\theta_{119} \\ \sin\theta_{119} & \cos\theta_{119}\cos\alpha_{119} & -\cos\theta_{119}\sin\alpha_{119} & a_{119}\sin\theta_{119} \\ 0 & \sin\alpha_{119} & \cos\alpha_{119} & d_{119} \\ 0 & 0 & 0 & 1 \end{bmatrix}$$

Joint 120 connects the right index finger Proximal Phalanx to the right index finger Metacarpal in the 2$^{nd}$ metacarpophalangeal joint (MCP). The $d_{120}$ length of the right index finger Proximal Phalanx runs through the centroid of the index finger Proximal Phalanx from the head of the index finger Metacarpus to the head of the index finger Proximal Phalanx.

$$A_{120} = \begin{bmatrix} \cos\theta_{120} & -\sin\theta_{120} & 0 & 0 \\ \sin\theta_{120} & \cos\theta_{120} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{120} \\ 0 & 0 & 0 & 1 \end{bmatrix} \begin{bmatrix} 1 & 0 & 0 & a_{120} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{120} & -\sin\alpha_{120} & 0 \\ 0 & \sin\alpha_{120} & \cos\alpha_{120} & 0 \\ 0 & 0 & 0 & 1 \end{bmatrix}$$

$$A_{120} = \begin{bmatrix} \cos\theta_{120} & -\sin\theta_{120}\cos\alpha_{120} & \sin\theta_{120}\sin\alpha_{120} & a_{120}\cos\theta_{120} \\ \sin\theta_{120} & \cos\theta_{120}\cos\alpha_{120} & -\cos\theta_{120}\sin\alpha_{120} & a_{120}\sin\theta_{120} \\ 0 & \sin\alpha_{120} & \cos\alpha_{120} & d_{120} \\ 0 & 0 & 0 & 1 \end{bmatrix}$$

Joint 121 connects the right middle finger Proximal Phalanx to the right middle finger Metacarpal in the 3$^{rd}$ metacarpophalangeal joint (MCP). The $d_{121}$ length of the right middle finger Proximal Phalanx runs through the centroid of the right middle finger Proximal Phalanx from the head of the middle finger Metacarpus to the head of the middle finger Proximal Phalanx.

$$A_{121} = \begin{bmatrix} \cos\theta_{121} & -\sin\theta_{121} & 0 & 0 \\ \sin\theta_{121} & \cos\theta_{121} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{121} \\ 0 & 0 & 0 & 1 \end{bmatrix} \begin{bmatrix} 1 & 0 & 0 & a_{121} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{121} & -\sin\alpha_{121} & 0 \\ 0 & \sin\alpha_{121} & \cos\alpha_{121} & 0 \\ 0 & 0 & 0 & 1 \end{bmatrix}$$

$$A_{121} = \begin{bmatrix} \cos\theta_{121} & -\sin\theta_{121}\cos\alpha_{121} & \sin\theta_{121}\sin\alpha_{121} & a_{121}\cos\theta_{121} \\ \sin\theta_{121} & \cos\theta_{121}\cos\alpha_{121} & -\cos\theta_{121}\sin\alpha_{121} & a_{121}\sin\theta_{121} \\ 0 & \sin\alpha_{121} & \cos\alpha_{121} & d_{121} \\ 0 & 0 & 0 & 1 \end{bmatrix}$$

Joint 122 connects the right ring finger Proximal Phalanx to the right ring finger Metacarpal in the $4^{th}$ metacarpophalangeal joint (MCP). The $d_{122}$ length of the right ring finger Proximal Phalanx runs through the centroid of the right ring finger Proximal Phalanx from the head of the ring finger Metacarpus to the head of the ring finger Proximal Phalanx.

$$A_{122} = \begin{bmatrix} \cos\theta_{122} & -\sin\theta_{122} & 0 & 0 \\ \sin\theta_{122} & \cos\theta_{122} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{122} \\ 0 & 0 & 0 & 1 \end{bmatrix} \begin{bmatrix} 1 & 0 & 0 & a_{122} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{122} & -\sin\alpha_{122} & 0 \\ 0 & \sin\alpha_{122} & \cos\alpha_{122} & 0 \\ 0 & 0 & 0 & 1 \end{bmatrix}$$

$$A_{122} = \begin{bmatrix} \cos\theta_{122} & -\sin\theta_{122}\cos\alpha_{122} & \sin\theta_{122}\sin\alpha_{122} & a_{122}\cos\theta_{122} \\ \sin\theta_{122} & \cos\theta_{122}\cos\alpha_{122} & -\cos\theta_{122}\sin\alpha_{122} & a_{122}\sin\theta_{122} \\ 0 & \sin\alpha_{122} & \cos\alpha_{122} & d_{122} \\ 0 & 0 & 0 & 1 \end{bmatrix}$$

Joint 123 connects the right little finger Proximal Phalanx to the right little finger Metacarpal in the $5^{th}$ metacarpophalangeal joint (MCP). The $d_{123}$ length of the right little finger Proximal Phalanx runs through the centroid of the right little finger Proximal Phalanx from the head of the little finger Metacarpus to the head of the little finger Proximal Phalanx.

$$A_{123} = \begin{bmatrix} \cos\theta_{123} & -\sin\theta_{123} & 0 & 0 \\ \sin\theta_{123} & \cos\theta_{123} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{123} \\ 0 & 0 & 0 & 1 \end{bmatrix} \begin{bmatrix} 1 & 0 & 0 & a_{123} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{123} & -\sin\alpha_{123} & 0 \\ 0 & \sin\alpha_{123} & \cos\alpha_{123} & 0 \\ 0 & 0 & 0 & 1 \end{bmatrix}$$

$$A_{123} = \begin{bmatrix} \cos\theta_{123} & -\sin\theta_{123}\cos\alpha_{123} & \sin\theta_{123}\sin\alpha_{123} & a_{123}\cos\theta_{123} \\ \sin\theta_{123} & \cos\theta_{123}\cos\alpha_{123} & -\cos\theta_{123}\sin\alpha_{123} & a_{123}\sin\theta_{123} \\ 0 & \sin\alpha_{123} & \cos\alpha_{123} & d_{123} \\ 0 & 0 & 0 & 1 \end{bmatrix}$$

Joint 124 connects the right thumb Metacarpal to the right Trapezium. The $d_{124}$ length of the right thumb Metacarpal runs through the centroid of the right thumb Metacarpal.

$$A_{124} = \begin{bmatrix} \cos\theta_{124} & -\sin\theta_{124} & 0 & 0 \\ \sin\theta_{124} & \cos\theta_{124} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{124} \\ 0 & 0 & 0 & 1 \end{bmatrix} \begin{bmatrix} 1 & 0 & 0 & a_{124} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{124} & -\sin\alpha_{124} & 0 \\ 0 & \sin\alpha_{124} & \cos\alpha_{124} & 0 \\ 0 & 0 & 0 & 1 \end{bmatrix}$$

$$A_{124} = \begin{bmatrix} \cos\theta_{124} & -\sin\theta_{124}\cos\alpha_{124} & \sin\theta_{124}\sin\alpha_{124} & a_{124}\cos\theta_{124} \\ \sin\theta_{124} & \cos\theta_{124}\cos\alpha_{124} & -\cos\theta_{124}\sin\alpha_{124} & a_{124}\sin\theta_{124} \\ 0 & \sin\alpha_{124} & \cos\alpha_{124} & d_{124} \\ 0 & 0 & 0 & 1 \end{bmatrix}$$

Joint 125 connects the right thumb Metacarpal to the right Index finger Metacarpal. The $d_{125}$ length of the right thumb Metacarpal runs through the centroid of the right thumb Metacarpal, beginning at the head of the right Trapezium, and extending to the head of the right thumb Metacarpal.

$$A_{125} = \begin{bmatrix} \cos\theta_{125} & -\sin\theta_{125} & 0 & 0 \\ \sin\theta_{125} & \cos\theta_{125} & 0 & 0 \\ 0 & 0 & 1 & 0 \\ 0 & 0 & 0 & 1 \end{bmatrix} \text{middle}$$

$$\text{finger} \begin{bmatrix} 1 & 0 & 0 & 0 \\ 0 & 1 & 0 & 0 \\ 0 & 0 & 1 & d_{125} \\ 0 & 0 & 0 & 1 \end{bmatrix} \begin{bmatrix} 1 & 0 & 0 & a_{125} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{125} & -\sin\alpha_{125} & 0 \\ 0 & \sin\alpha_{125} & \cos\alpha_{125} & 0 \\ 0 & 0 & 0 & 1 \end{bmatrix}$$

$$A_{125} = \begin{bmatrix} \cos\theta_{125} & -\sin\theta_{125}\cos\alpha_{125} & \sin\theta_{125}\sin\alpha_{125} & a_{125}\cos\theta_{125} \\ \sin\theta_{125} & \cos\theta_{125}\cos\alpha_{125} & -\cos\theta_{125}\sin\alpha_{125} & a_{125}\sin\theta_{125} \\ 0 & \sin\alpha_{125} & \cos\alpha_{125} & d_{125} \\ 0 & 0 & 0 & 1 \end{bmatrix}$$

Joint 126 connects the right index finger Metacarpal to the right middle finger Metacarpal. The $d_{126}$ length of the right index finger Metacarpal runs through the centroid of the right index finger Metacarpal beginning at the side of the right middle finger Metacarpal.

$$A_{126} =$$
$$\begin{bmatrix} \cos\theta_{126} & -\sin\theta_{126} & 0 & 0 \\ \sin\theta_{126} & \cos\theta_{126} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{126} \\ 0 & 0 & 0 & 1 \end{bmatrix} \begin{bmatrix} 1 & 0 & 0 & a_{126} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{126} & -\sin\alpha_{126} & 0 \\ 0 & \sin\alpha_{126} & \cos\alpha_{126} & 0 \\ 0 & 0 & 0 & 1 \end{bmatrix}$$

$$A_{126} = \begin{bmatrix} \cos\theta_{126} & -\sin\theta_{126}\cos\alpha_{126} & \sin\theta_{126}\sin\alpha_{126} & a_{126}\cos\theta_{126} \\ \sin\theta_{126} & \cos\theta_{126}\cos\alpha_{126} & -\cos\theta_{126}\sin\alpha_{126} & a_{126}\sin\theta_{126} \\ 0 & \sin\alpha_{126} & \cos\alpha_{126} & d_{126} \\ 0 & 0 & 0 & 1 \end{bmatrix}$$

Joint 127 connects the right middle finger Metacarpal to the right ring finger Metacarpal. The $d_{127}$ length of the right middle finger Metacarpal runs through the right middle finger Metacarpal beginning at the side of the right middle finger Metacarpal to the head of the right middle finger Metacarpal.

$$A_{127} = \begin{bmatrix} \cos\theta_{127} & -\sin\theta_{127} & 0 & 0 \\ \sin\theta_{127} & \cos\theta_{127} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{127} \\ 0 & 0 & 0 & 1 \end{bmatrix} \begin{bmatrix} 1 & 0 & 0 & a_{127} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{127} & -\sin\alpha_{127} & 0 \\ 0 & \sin\alpha_{127} & \cos\alpha_{127} & 0 \\ 0 & 0 & 0 & 1 \end{bmatrix}$$

$$A_{127} = \begin{bmatrix} \cos\theta_{127} & -\sin\theta_{127}\cos\alpha_{127} & \sin\theta_{127}\sin\alpha_{127} & a_{127}\cos\theta_{127} \\ \sin\theta_{127} & \cos\theta_{127}\cos\alpha_{127} & -\cos\theta_{127}\sin\alpha_{127} & a_{127}\sin\theta_{127} \\ 0 & \sin\alpha_{127} & \cos\alpha_{127} & d_{127} \\ 0 & 0 & 0 & 1 \end{bmatrix}$$

Joint 128 connects the right index finger Metacarpal to the Right Trapezium. The $d_{128}$ length of the right index finger Metacarpal runs through the right index finger Metacarpal beginning at the head of the right trapezium to the head of the right index finger Metacarpal.

$$A_{128} = \begin{bmatrix} \cos\theta_{128} & -\sin\theta_{128} & 0 & 0 \\ \sin\theta_{128} & \cos\theta_{128} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{128} \\ 0 & 0 & 0 & 1 \end{bmatrix} \begin{bmatrix} 1 & 0 & 0 & a_{128} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{128} & -\sin\alpha_{128} & 0 \\ 0 & \sin\alpha_{128} & \cos\alpha_{128} & 0 \\ 0 & 0 & 0 & 1 \end{bmatrix}$$

$$A_{128} = \begin{bmatrix} \cos\theta_{128} & -\sin\theta_{128}\cos\alpha_{128} & \sin\theta_{128}\sin\alpha_{128} & a_{128}\cos\theta_{128} \\ \sin\theta_{128} & \cos\theta_{128}\cos\alpha_{128} & -\cos\theta_{128}\sin\alpha_{128} & a_{128}\sin\theta_{128} \\ 0 & \sin\alpha_{128} & \cos\alpha_{128} & d_{128} \\ 0 & 0 & 0 & 1 \end{bmatrix}$$

Joint 129 connects the right index finger Metacarpal to the right Trapezoid. The $d_{128}$ length of the right index finger Metacarpal runs through the right index finger Metacarpal beginning at the head of the right trapezoid to the head of the right index finger Metacarpal.

$$A_{129} = \begin{bmatrix} \cos\theta_{129} & -\sin\theta_{129} & 0 & 0 \\ \sin\theta_{129} & \cos\theta_{129} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{129} \\ 0 & 0 & 0 & 1 \end{bmatrix} \begin{bmatrix} 1 & 0 & 0 & a_{129} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{129} & -\sin\alpha_{129} & 0 \\ 0 & \sin\alpha_{129} & \cos\alpha_{129} & 0 \\ 0 & 0 & 0 & 1 \end{bmatrix}$$

-continued $$A_{129} = \begin{bmatrix} \cos\theta_{129} & -\sin\theta_{129}\cos\alpha_{129} & \sin\theta_{129}\sin\alpha_{129} & a_{129}\cos\theta_{129} \\ \sin\theta_{129} & \cos\theta_{129}\cos\alpha_{129} & -\cos\theta_{129}\sin\alpha_{129} & a_{129}\sin\theta_{129} \\ 0 & \sin\alpha_{129} & \cos\alpha_{129} & d_{129} \\ 0 & 0 & 0 & 1 \end{bmatrix}$$

Joint 130 connects the right middle finger to the right Trapezoid. The $d_{130}$ length of the right index finger Metacarpal runs through the right index finger Metacarpal beginning at the head of the right trapezoid to the head of the right index finger Metacarpal.

$$A_{130} = \begin{bmatrix} \cos\theta_{130} & -\sin\theta_{130} & 0 & 0 \\ \sin\theta_{130} & \cos\theta_{130} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{130} \\ 0 & 0 & 0 & 1 \end{bmatrix} \begin{bmatrix} 1 & 0 & 0 & a_{130} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{130} & -\sin\alpha_{130} & 0 \\ 0 & \sin\alpha_{130} & \cos\alpha_{130} & 0 \\ 0 & 0 & 0 & 1 \end{bmatrix}$$

$$A_{130} = \begin{bmatrix} \cos\theta_{130} & -\sin\theta_{130}\cos\alpha_{130} & \sin\theta_{130}\sin\alpha_{130} & a_{130}\cos\theta_{130} \\ \sin\theta_{130} & \cos\theta_{130}\cos\alpha_{130} & -\cos\theta_{130}\sin\alpha_{130} & a_{130}\sin\theta_{130} \\ 0 & \sin\alpha_{130} & \cos\alpha_{130} & d_{130} \\ 0 & 0 & 0 & 1 \end{bmatrix}$$

Joint 131 connects the right middle finger Metacarpal to the right Capitate. The $d_{131}$ length of the right index finger Metacarpal runs through the right index finger Metacarpal beginning at the head of the right Capitate to the head of the right index finger Metacarpal.

$$A_{131} = \begin{bmatrix} \cos\theta_{131} & -\sin\theta_{131} & 0 & 0 \\ \sin\theta_{131} & \cos\theta_{131} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{131} \\ 0 & 0 & 0 & 1 \end{bmatrix} \begin{bmatrix} 1 & 0 & 0 & a_{131} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{131} & -\sin\alpha_{131} & 0 \\ 0 & \sin\alpha_{131} & \cos\alpha_{131} & 0 \\ 0 & 0 & 0 & 1 \end{bmatrix}$$

$$A_{131} = \begin{bmatrix} \cos\theta_{131} & -\sin\theta_{131}\cos\alpha_{131} & \sin\theta_{131}\sin\alpha_{131} & a_{131}\cos\theta_{131} \\ \sin\theta_{131} & \cos\theta_{131}\cos\alpha_{131} & -\cos\theta_{131}\sin\alpha_{131} & a_{131}\sin\theta_{131} \\ 0 & \sin\alpha_{131} & \cos\alpha_{131} & d_{131} \\ 0 & 0 & 0 & 1 \end{bmatrix}$$

Joint 132 connects the right middle finger Metacarpal to the right ring finger Metacarpal. The $d_{132}$ length of the right middle finger Metacarpal runs through the right middle finger Metacarpal beginning at the head of the right Metacarpal to the head of the right middle finger Metacarpal.

$$A_{132} = \begin{bmatrix} \cos\theta_{132} & -\sin\theta_{132} & 0 & 0 \\ \sin\theta_{132} & \cos\theta_{132} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{132} \\ 0 & 0 & 0 & 1 \end{bmatrix} \begin{bmatrix} 1 & 0 & 0 & a_{132} \\ 0 & 1 & 0 & 0 \\ 0 & 0 & 1 & 0 \\ 0 & 0 & 0 & 1 \end{bmatrix}$$

$$A_{132} = \begin{bmatrix} 1 & 0 & 0 & 0 \\ 0 & \cos\alpha_{132} & -\sin\alpha_{132} & 0 \\ 0 & \sin\alpha_{132} & \cos\alpha_{132} & 0 \\ 0 & 0 & 0 & 1 \end{bmatrix}$$

$$A_{132} = \begin{bmatrix} \cos\theta_{132} & -\sin\theta_{132}\cos\alpha_{132} & \sin\theta_{132}\sin\alpha_{132} & a_{132}\cos\theta_{132} \\ \sin\theta_{132} & \cos\theta_{132}\cos\alpha_{132} & -\cos\theta_{132}\sin\alpha_{132} & a_{132}\sin\theta_{132} \\ 0 & \sin\alpha_{132} & \cos\alpha_{132} & d_{132} \\ 0 & 0 & 0 & 1 \end{bmatrix}$$

Joint 133 connects the right ring finger Metacarpal to the Right Capitate. The $d_{133}$ length of the right ring finger Metacarpal runs through the right middle finger Metacarpal beginning at the head of the right Metacarpal to the head of the right Capitate.

$$A_{133} = \begin{bmatrix} \cos\theta_{133} & -\sin\theta_{133} & 0 & 0 \\ \sin\theta_{133} & \cos\theta_{133} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{133} \\ 0 & 0 & 0 & 1 \end{bmatrix} \begin{bmatrix} 1 & 0 & 0 & a_{133} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{133} & -\sin\alpha_{133} & 0 \\ 0 & \sin\alpha_{133} & \cos\alpha_{133} & 0 \\ 0 & 0 & 0 & 1 \end{bmatrix}$$

$$A_{133} = \begin{bmatrix} \cos\theta_{133} & -\sin\theta_{133}\cos\alpha_{133} & \sin\theta_{133}\sin\alpha_{133} & a_{133}\cos\theta_{133} \\ \sin\theta_{133} & \cos\theta_{133}\cos\alpha_{133} & -\cos\theta_{133}\sin\alpha_{133} & a_{133}\sin\theta_{133} \\ 0 & \sin\alpha_{133} & \cos\alpha_{133} & d_{133} \\ 0 & 0 & 0 & 1 \end{bmatrix}$$

Joint 134 connects the right ring finger Metacarpal to the right little finger Metacarpal. The $d_{134}$ length of the right ring finger Metacarpal runs through the right middle finger Metacarpal beginning at the touchpoint of the right little finger Metacarpal to the touchpoint on the little finger Metacarpal.

$$A_{134} = \begin{bmatrix} \cos\theta_{134} & -\sin\theta_{134} & 0 & 0 \\ \sin\theta_{134} & \cos\theta_{134} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{134} \\ 0 & 0 & 0 & 1 \end{bmatrix} \begin{bmatrix} 1 & 0 & 0 & a_{134} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{134} & -\sin\alpha_{134} & 0 \\ 0 & \sin\alpha_{134} & \cos\alpha_{134} & 0 \\ 0 & 0 & 0 & 1 \end{bmatrix}$$

$$A_{134} = \begin{bmatrix} \cos\theta_{134} & -\sin\theta_{134}\cos\alpha_{134} & \sin\theta_{134}\sin\alpha_{134} & a_{134}\cos\theta_{134} \\ \sin\theta_{134} & \cos\theta_{134}\cos\alpha_{134} & -\cos\theta_{134}\sin\alpha_{134} & a_{134}\sin\theta_{134} \\ 0 & \sin\alpha_{134} & \cos\alpha_{134} & d_{134} \\ 0 & 0 & 0 & 1 \end{bmatrix}$$

Joint 135 connects the right ring finger Metacarpal to the right Hamate. The $d_{135}$ length of the right ring finger Metacarpal runs through the right middle finger Metacarpal beginning at the touchpoint of the right little finger Metacarpal to the touchpoint on the right Hamate.

$$A_{135} = \begin{bmatrix} \cos\theta_{135} & -\sin\theta_{135} & 0 & 0 \\ \sin\theta_{135} & \cos\theta_{135} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{135} \\ 0 & 0 & 0 & 1 \end{bmatrix} \begin{bmatrix} 1 & 0 & 0 & a_{135} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{135} & -\sin\alpha_{135} & 0 \\ 0 & \sin\alpha_{135} & \cos\alpha_{135} & 0 \\ 0 & 0 & 0 & 1 \end{bmatrix}$$

$$A_{135} = \begin{bmatrix} \cos\theta_{135} & -\sin\theta_{135}\cos\alpha_{135} & \sin\theta_{135}\sin\alpha_{135} & a_{135}\cos\theta_{135} \\ \sin\theta_{135} & \cos\theta_{135}\cos\alpha_{135} & -\cos\theta_{135}\sin\alpha_{135} & a_{135}\sin\theta_{135} \\ 0 & \sin\alpha_{135} & \cos\alpha_{135} & d_{135} \\ 0 & 0 & 0 & 1 \end{bmatrix}$$

Joint 136 connects the right little finger Metacarpal to the right Hamate. The $d_{136}$ length of the right little finger Metacarpal runs through the right little finger Metacarpal beginning at the touchpoint of the right little finger Metacarpal to the touchpoint on the right Hamate.

$$A_{136} = \begin{bmatrix} \cos\theta_{136} & -\sin\theta_{136} & 0 & 0 \\ \sin\theta_{136} & \cos\theta_{136} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{136} \\ 0 & 0 & 0 & 1 \end{bmatrix} \begin{bmatrix} 1 & 0 & 0 & a_{136} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{136} & -\sin\alpha_{136} & 0 \\ 0 & \sin\alpha_{136} & \cos\alpha_{136} & 0 \\ 0 & 0 & 0 & 1 \end{bmatrix}$$

$$A_{136} = \begin{bmatrix} \cos\theta_{136} & -\sin\theta_{136}\cos\alpha_{136} & \sin\theta_{136}\sin\alpha_{136} & a_{136}\cos\theta_{136} \\ \sin\theta_{136} & \cos\theta_{136}\cos\alpha_{136} & -\cos\theta_{136}\sin\alpha_{136} & a_{136}\sin\theta_{136} \\ 0 & \sin\alpha_{136} & \cos\alpha_{136} & d_{136} \\ 0 & 0 & 0 & 1 \end{bmatrix}$$

Joint 137 connects the right Trapezium to the right Trapezoid. The $d_{137}$ length of the right Trapezium runs through the right Trapezium beginning at the touchpoint of the right Trapezoid to the touchpoint on the right Trapezium.

$$A_{137} = \begin{bmatrix} \cos\theta_{137} & -\sin\theta_{137} & 0 & 0 \\ \sin\theta_{137} & \cos\theta_{137} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{137} \\ 0 & 0 & 0 & 1 \end{bmatrix} \begin{bmatrix} 1 & 0 & 0 & a_{137} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{137} & -\sin\alpha_{137} & 0 \\ 0 & \sin\alpha_{137} & \cos\alpha_{137} & 0 \\ 0 & 0 & 0 & 1 \end{bmatrix}$$

$$A_{137} = \begin{bmatrix} \cos\theta_{137} & -\sin\theta_{137}\cos\alpha_{137} & \sin\theta_{137}\sin\alpha_{137} & a_{137}\cos\theta_{137} \\ \sin\theta_{137} & \cos\theta_{137}\cos\alpha_{137} & -\cos\theta_{137}\sin\alpha_{137} & a_{137}\sin\theta_{137} \\ 0 & \sin\alpha_{137} & \cos\alpha_{137} & d_{137} \\ 0 & 0 & 0 & 1 \end{bmatrix}$$

Joint 138 connects the right Trapezium to the right Scaphoid. The $d_{138}$ length of the right Trapezium runs from the left head of the Scaphoid to the left head of the Trapezium.

$$A_{138} = \begin{bmatrix} \cos\theta_{138} & -\sin\theta_{138} & 0 & 0 \\ \sin\theta_{138} & \cos\theta_{138} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{138} \\ 0 & 0 & 0 & 1 \end{bmatrix} \begin{bmatrix} 1 & 0 & 0 & a_{138} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{138} & -\sin\alpha_{138} & 0 \\ 0 & \sin\alpha_{138} & \cos\alpha_{138} & 0 \\ 0 & 0 & 0 & 1 \end{bmatrix}$$

$$A_{138} = \begin{bmatrix} \cos\theta_{138} & -\sin\theta_{138}\cos\alpha_{138} & \sin\theta_{138}\sin\alpha_{138} & a_{138}\cos\theta_{138} \\ \sin\theta_{138} & \cos\theta_{138}\cos\alpha_{138} & -\cos\theta_{138}\sin\alpha_{138} & a_{138}\sin\theta_{138} \\ 0 & \sin\alpha_{138} & \cos\alpha_{138} & d_{138} \\ 0 & 0 & 0 & 1 \end{bmatrix}$$

Joint 139 connects the right Trapezoid to the right Capitate. The $d_{139}$ length of the right Trapezoid runs from the left head of the Capitate to the left head of the Trapezoid.

$$A_{139} = \begin{bmatrix} \cos\theta_{139} & -\sin\theta_{139} & 0 & 0 \\ \sin\theta_{139} & \cos\theta_{139} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{139} \\ 0 & 0 & 0 & 1 \end{bmatrix} \begin{bmatrix} 1 & 0 & 0 & a_{139} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{139} & -\sin\alpha_{139} & 0 \\ 0 & \sin\alpha_{139} & \cos\alpha_{139} & 0 \\ 0 & 0 & 0 & 1 \end{bmatrix}$$

$$A_{139} = \begin{bmatrix} \cos\theta_{139} & -\sin\theta_{139}\cos\alpha_{139} & \sin\theta_{139}\sin\alpha_{139} & a_{139}\cos\theta_{139} \\ \sin\theta_{139} & \cos\theta_{139}\cos\alpha_{139} & -\cos\theta_{139}\sin\alpha_{139} & a_{139}\sin\theta_{139} \\ 0 & \sin\alpha_{139} & \cos\alpha_{139} & d_{139} \\ 0 & 0 & 0 & 1 \end{bmatrix}$$

Joint 140 connects the right Trapezoid to the right Scaphoid. The $d_{140}$ length of the right Trapezoid runs from the left head of the Scaphoid to the left head of the Trapezoid.

$$A_{140} = \begin{bmatrix} \cos\theta_{140} & -\sin\theta_{140} & 0 & 0 \\ \sin\theta_{140} & \cos\theta_{140} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{140} \\ 0 & 0 & 0 & 1 \end{bmatrix} \begin{bmatrix} 1 & 0 & 0 & a_{140} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{140} & -\sin\alpha_{140} & 0 \\ 0 & \sin\alpha_{140} & \cos\alpha_{140} & 0 \\ 0 & 0 & 0 & 1 \end{bmatrix}$$

$$A_{140} = \begin{bmatrix} \cos\theta_{140} & -\sin\theta_{140}\cos\alpha_{140} & \sin\theta_{140}\sin\alpha_{140} & a_{140}\cos\theta_{140} \\ \sin\theta_{140} & \cos\theta_{140}\cos\alpha_{140} & -\cos\theta_{140}\sin\alpha_{140} & a_{140}\sin\theta_{140} \\ 0 & \sin\alpha_{140} & \cos\alpha_{140} & d_{140} \\ 0 & 0 & 0 & 1 \end{bmatrix}$$

Joint 141 connects the right Capitate to the right Hamate. The $d_{141}$ length of the right Capitate runs from the left head of the Capitate to the left head of the Hamate.

$$A_{141} = \begin{bmatrix} \cos\theta_{141} & -\sin\theta_{141} & 0 & 0 \\ \sin\theta_{141} & \cos\theta_{141} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{141} \\ 0 & 0 & 0 & 1 \end{bmatrix} \begin{bmatrix} 1 & 0 & 0 & a_{141} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{141} & -\sin\alpha_{141} & 0 \\ 0 & \sin\alpha_{141} & \cos\alpha_{141} & 0 \\ 0 & 0 & 0 & 1 \end{bmatrix}$$

$$A_{141} = \begin{bmatrix} \cos\theta_{141} & -\sin\theta_{141}\cos\alpha_{141} & \sin\theta_{141}\sin\alpha_{141} & a_{141}\cos\theta_{141} \\ \sin\theta_{141} & \cos\theta_{141}\cos\alpha_{141} & -\cos\theta_{141}\sin\alpha_{141} & a_{141}\sin\theta_{141} \\ 0 & \sin\alpha_{141} & \cos\alpha_{141} & d_{141} \\ 0 & 0 & 0 & 1 \end{bmatrix}$$

Joint 142 connects the right Hamate to the right Triquetral. The $d_{142}$ length of the right Hamate runs from the left head of the Triquetral to the left head of the Hamate.

$$A_{142} = \begin{bmatrix} \cos\varphi_{142} & -\sin\varphi_{142} & 0 & 0 \\ \sin\varphi_{142} & \cos\varphi_{142} & 0 & 0 \\ 0 & 0 & 1 & 0 \\ 0 & 0 & 0 & 1 \end{bmatrix} \begin{bmatrix} \cos\theta_{142} & 0 & \sin\theta_{142} & 0 \\ 0 & 1 & 0 & 0 \\ -\sin\theta_{142} & 0 & \cos\theta_{142} & 0 \\ 0 & 0 & 0 & 1 \end{bmatrix}$$

$$\begin{bmatrix} 1 & 0 & 0 & 0 \\ 0 & \cos\varphi_{142} & -\sin\varphi_{142} & 0 \\ 0 & \sin\varphi_{142} & \cos\varphi_{142} & 0 \\ 0 & 0 & 0 & 1 \end{bmatrix}$$

$$A_{142} = \begin{bmatrix} \cos\theta_{142} & -\sin\theta_{142}\cos\alpha_{142} & \sin\theta_{142}\sin\alpha_{142} & a_{142}\cos\theta_{142} \\ \sin\theta_{142} & \cos\theta_{142}\cos\alpha_{142} & -\cos\theta_{142}\sin\alpha_{142} & a_{142}\sin\theta_{142} \\ 0 & \sin\alpha_{142} & \cos\alpha_{142} & d_{142} \\ 0 & 0 & 0 & 1 \end{bmatrix}$$

Joint 143 connects the right Triquetral to the right Lunate. The $d_{143}$ length of the right Lunate runs from the right head of the Scaphoid to the left head of the Lunate.

$$A_{143} = \begin{bmatrix} \cos\varphi_{143} & -\sin\varphi_{143} & 0 & 0 \\ \sin\varphi_{143} & \cos\varphi_{143} & 0 & 0 \\ 0 & 0 & 1 & 0 \\ 0 & 0 & 0 & 1 \end{bmatrix} \begin{bmatrix} \cos\theta_{143} & 0 & \sin\theta_{143} & 0 \\ 0 & 1 & 0 & 0 \\ -\sin\theta_{143} & 0 & \cos\theta_{143} & 0 \\ 0 & 0 & 0 & 1 \end{bmatrix}$$

$$\begin{bmatrix} 1 & 0 & 0 & 0 \\ 0 & \cos\varphi_{143} & -\sin\varphi_{143} & 0 \\ 0 & \sin\varphi_{143} & \cos\varphi_{143} & 0 \\ 0 & 0 & 0 & 1 \end{bmatrix}$$

$$A_{143} = \begin{bmatrix} \cos\theta_{143} & -\sin\theta_{143}\cos\alpha_{143} & \sin\theta_{143}\sin\alpha_{143} & a_{143}\cos\theta_{143} \\ \sin\theta_{143} & \cos\theta_{143}\cos\alpha_{143} & -\cos\theta_{143}\sin\alpha_{143} & a_{143}\sin\theta_{143} \\ 0 & \sin\alpha_{143} & \cos\alpha_{143} & d_{143} \\ 0 & 0 & 0 & 1 \end{bmatrix}$$

Joint 144 connects the right Lunate to the right Capitate. The $d_{144}$ length of the right Lunate runs from the left head of the Lunate to the left head of the Capitate.

$$A_{144} = \begin{bmatrix} \cos\theta_{144} & -\sin_{144} & 0 & 0 \\ \sin\theta_{144} & \cos\theta_{144} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{144} \\ 0 & 0 & 0 & 1 \end{bmatrix} \begin{bmatrix} 1 & 0 & 0 & a_{144} \\ 0 & 1 & 0 & 0 \\ 0 & 0 & 1 & 0 \\ 0 & 0 & 0 & 1 \end{bmatrix}$$

$$A_{144} = \begin{bmatrix} 1 & 0 & 0 & 0 \\ 0 & \cos\alpha_{144} & -\sin\alpha_{144} & 0 \\ 0 & \sin\alpha_{144} & \cos\alpha_{144} & 0 \\ 0 & 0 & 0 & 1 \end{bmatrix}$$

$$A_{144} = \begin{bmatrix} \cos\theta_{144} & -\sin\theta_{144}\cos\alpha_{144} & \sin\theta_{144}\sin\alpha_{144} & a_{144}\cos\theta_{144} \\ \sin\theta_{144} & \cos\theta_{144}\cos\alpha_{144} & -\cos\theta_{144}\sin\alpha_{144} & a_{144}\sin\theta_{144} \\ 0 & \sin\alpha_{144} & \cos\alpha_{144} & d_{144} \\ 0 & 0 & 0 & 1 \end{bmatrix}$$

Joint 145 connects the right Capitate to the right Scaphoid. The $d_{145}$ length of the right Capitate runs from the right head of the Scaphoid to the head of the Scaphoid.

$$A_{145} = \begin{bmatrix} \cos\varphi_{145} & -\sin\varphi_{145} & 0 & 0 \\ \sin\varphi_{145} & \cos\varphi_{145} & 0 & 0 \\ 0 & 0 & 1 & 0 \\ 0 & 0 & 0 & 1 \end{bmatrix} \begin{bmatrix} \cos\theta_{145} & 0 & \sin\theta_{145} & 0 \\ 0 & 1 & 0 & 0 \\ -\sin\theta_{145} & 0 & \cos\theta_{145} & 0 \\ 0 & 0 & 0 & 1 \end{bmatrix}$$

$$\begin{bmatrix} 1 & 0 & 0 & 0 \\ 0 & \cos\varphi_{145} & -\sin\varphi_{145} & 0 \\ 0 & \sin\varphi_{145} & \cos\varphi_{145} & 0 \\ 0 & 0 & 0 & 1 \end{bmatrix}$$

$$A_{145} = \begin{bmatrix} \cos\theta_{145} & -\sin\theta_{145}\cos\alpha_{145} & \sin\theta_{145}\sin\alpha_{145} & a_{145}\cos\theta_{145} \\ \sin\theta_{145} & \cos\theta_{145}\cos\alpha_{145} & -\cos\theta_{145}\sin\alpha_{145} & a_{145}\sin\theta_{145} \\ 0 & \sin\alpha_{145} & \cos\alpha_{145} & d_{145} \\ 0 & 0 & 0 & 1 \end{bmatrix}$$

Joint 146 connects the right Scaphoid to the right Radius. The $d_{146}$ length of the right Scaphoid runs from the left head of the right Radius to the head of the Radius.

$$A_{146} = \begin{bmatrix} \cos\theta_{146} & -\sin\theta_{146} & 0 & 0 \\ \sin\theta_{146} & \cos\theta_{146} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{146} \\ 0 & 0 & 0 & 1 \end{bmatrix} \begin{bmatrix} 1 & 0 & 0 & a_{146} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{146} & -\sin\alpha_{146} & 0 \\ 0 & \sin\alpha_{146} & \cos\alpha_{146} & 0 \\ 0 & 0 & 0 & 1 \end{bmatrix}$$

$$A_{146} = \begin{bmatrix} \cos\theta_{146} & -\sin\theta_{146}\cos\alpha_{146} & \sin\theta_{146}\sin\alpha_{146} & a_{146}\cos\theta_{146} \\ \sin\theta_{146} & \cos\theta_{146}\cos\alpha_{146} & -\cos\theta_{146}\sin\alpha_{146} & a_{146}\sin\theta_{146} \\ 0 & \sin\alpha_{146} & \cos\alpha_{146} & d_{146} \\ 0 & 0 & 0 & 1 \end{bmatrix}$$

Joint 147 connects the right Radius to the right Ulna. The $d_{147}$ length of the right Radius runs from the left head of the Scaphoid to the left head of the Trapezium.

$$A_{147} = \begin{bmatrix} \cos\theta_{147} & -\sin\theta_{147} & 0 & 0 \\ \sin\theta_{147} & \cos\theta_{147} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{147} \\ 0 & 0 & 0 & 1 \end{bmatrix} \begin{bmatrix} 1 & 0 & 0 & a_{147} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{147} & -\sin\alpha_{147} & 0 \\ 0 & \sin\alpha_{147} & \cos\alpha_{147} & 0 \\ 0 & 0 & 0 & 1 \end{bmatrix}$$

$$A_{147} = \begin{bmatrix} \cos\theta_{147} & -\sin\theta_{147}\cos\alpha_{147} & \sin\theta_{147}\sin\alpha_{147} & a_{147}\cos\theta_{147} \\ \sin\theta_{147} & \cos\theta_{147}\cos\alpha_{147} & -\cos\theta_{147}\sin\alpha_{147} & a_{147}\sin\theta_{147} \\ 0 & \sin\alpha_{147} & \cos\alpha_{147} & d_{147} \\ 0 & 0 & 0 & 1 \end{bmatrix}$$

Joint 148 connects the right Ulna to the right Lunate. The $d_{148}$ length of the right Ulna runs from the left head of the Ulna to the right head of the Lunate.

$$A_{148} = \begin{bmatrix} \cos\varphi_{148} & -\sin\varphi_{148} & 0 & 0 \\ \sin\varphi_{148} & \cos\varphi_{148} & 0 & 0 \\ 0 & 0 & 1 & 0 \\ 0 & 0 & 0 & 1 \end{bmatrix} \begin{bmatrix} \cos\theta_{148} & 0 & \sin\theta_{148} & 0 \\ 0 & 1 & 0 & 0 \\ -\sin\theta_{148} & 0 & \cos\theta_{148} & 0 \\ 0 & 0 & 0 & 1 \end{bmatrix}$$

$$\begin{bmatrix} 1 & 0 & 0 & 0 \\ 0 & \cos\varphi_{148} & -\sin\varphi_{148} & 0 \\ 0 & \sin\varphi_{148} & \cos\varphi_{148} & 0 \\ 0 & 0 & 0 & 1 \end{bmatrix}$$

$$A_{148} = \begin{bmatrix} \cos\theta_{148} & -\sin\theta_{148}\cos\alpha_{148} & \sin\theta_{148}\sin\alpha_{148} & a_{148}\cos\theta_{148} \\ \sin_{148} & \cos\theta_{148}\cos\alpha_{148} & -\cos\theta_{148}\sin\alpha_{148} & a_{148}\sin\theta_{148} \\ 0 & \sin\alpha_{148} & \cos\alpha_{148} & d_{148} \\ 0 & 0 & 0 & 1 \end{bmatrix}$$

Joint 149 connects the left thumb Distal Phalanx to the left thumb Proximal Phalanx, forming the $1^{st}$ distal interphalangeal joint (DIP). The $d_{149}$ length of the left Distal Phalanx runs through the centroid of the Distal Phalanx from the head of the left Proximal Phalanx to the head of the left distal phalanx $$A_{149} = \begin{bmatrix} \cos\theta_{149} & -\sin\theta_{149} & 0 & 0 \\ \sin\theta_{149} & \cos\theta_{149} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 0 & d_{149} \\ 0 & 0 & 0 & 1 \end{bmatrix} \begin{bmatrix} 1 & 0 & 0 & a_{149} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{149} & -\sin\alpha_{149} & 0 \\ 0 & \sin\alpha_{149} & \cos\alpha_{149} & 0 \\ 0 & 0 & 0 & 1 \end{bmatrix}$$

$$A_{149} = \begin{bmatrix} \cos\theta_{149} & -\sin\theta_{149}\cos\alpha_{149} & \sin\theta_{149}\sin\alpha_{149} & a_{149}\cos\theta_{149} \\ \sin\theta_{149} & \cos\theta_{149}\cos\alpha_{149} & -\cos\theta_{149}\sin\alpha_{149} & a_{149}\sin\theta_{149} \\ 0 & \sin\alpha_{149} & \cos\alpha_{149} & d_{149} \\ 0 & 0 & 0 & 1 \end{bmatrix}$$

Joint 150 connects the left index finger Distal Phalanx to the left index finger Middle Phalanx, forming the $2^{nd}$ distal interphalangeal joint (DIP) The $d_{150}$ length of the left index finger Digital Phalanx runs through the centroid of the Distal Phalanx from the head of the left index finger Proximal Phalanx to the head of the left index finger Distal Phalanx.

$$A_{150} = \begin{bmatrix} \cos\theta_{150} & -\sin\theta_{150} & 0 & 0 \\ \sin\theta_{150} & \cos\theta_{150} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{150} \\ 0 & 0 & 0 & 1 \end{bmatrix} \begin{bmatrix} 1 & 0 & 0 & a_{150} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{150} & -\sin\alpha_{150} & 0 \\ 0 & \sin\alpha_{150} & \cos\alpha_{150} & 0 \\ 0 & 0 & 0 & 1 \end{bmatrix}$$

$$A_{150} = \begin{bmatrix} \cos\theta_{150} & -\sin\theta_{150}\cos\alpha_{150} & \sin\theta_{150}\sin\alpha_{150} & a_{150}\cos\theta_{150} \\ \sin\theta_{150} & \cos\theta_{150}\cos\alpha_{150} & -\cos\theta_{150}\sin\alpha_{150} & a_{150}\sin\theta_{150} \\ 0 & \sin\alpha_{150} & \cos\alpha_{150} & d_{150} \\ 0 & 0 & 0 & 1 \end{bmatrix}$$

Joint 151 connects the left middle finger Distal Phalanx to the left middle finger Middle Phalanx, forming the $3^{rd}$ distal interphalangeal joint (DIP). The $d_{151}$ length of the left middle finger Digital Phalanx runs through the centroid of the Distal Phalanx from the head of the left index finger Proximal Phalanx to the dead of the left middle finger Distal Phalanx.

$$A_{151} = \begin{bmatrix} \cos\theta_{151} & -\sin\theta_{151} & 0 & 0 \\ \sin\theta_{151} & \cos\theta_{151} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{151} \\ 0 & 0 & 0 & 1 \end{bmatrix} \begin{bmatrix} 1 & 0 & 0 & a_{151} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{151} & -\sin\alpha_{151} & 0 \\ 0 & \sin\alpha_{151} & \cos\alpha_{151} & 0 \\ 0 & 0 & 0 & 1 \end{bmatrix}$$

$$A_{151} = \begin{bmatrix} \cos\theta_{151} & -\sin\theta_{151}\cos\alpha_{151} & \sin\theta_{151}\sin\alpha_{151} & a_{151}\cos\theta_{151} \\ \sin\theta_{151} & \cos\theta_{151}\cos\alpha_{151} & -\cos\theta_{151}\sin\alpha_{151} & a_{151}\sin\theta_{151} \\ 0 & \sin\alpha_{151} & \cos\alpha_{151} & d_{151} \\ 0 & 0 & 0 & 1 \end{bmatrix}$$

Joint 152 connects the left ring finger Distal Phalanx to the left ring finger Middle Phalanx, forming the $4^{th}$ distal interphalangeal joint (DIP). The $d_{152}$ length of the left ring finger Digital Phalanx runs through the centroid of the Distal Phalanx from the head of the left ring finger Proximal Phalanx to the head of the left ring finger Distal Phalanx.

$$A_{152} = \begin{bmatrix} \cos\theta_{152} & -\sin\theta_{152} & 0 & 0 \\ \sin\theta_{152} & \cos\theta_{152} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{152} \\ 0 & 0 & 0 & 1 \end{bmatrix} \begin{bmatrix} 1 & 0 & 0 & a_{152} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{152} & -\sin\alpha_{152} & 0 \\ 0 & \sin\alpha_{152} & \cos\alpha_{152} & 0 \\ 0 & 0 & 0 & 1 \end{bmatrix}$$

$$A_{152} = \begin{bmatrix} \cos\theta_{152} & -\sin\theta_{152}\cos\alpha_{152} & \sin\theta_{152}\sin\alpha_{152} & a_{152}\cos\theta_{152} \\ \sin\theta_{152} & \cos\theta_{152}\cos\alpha_{152} & -\cos\theta_{152}\sin\alpha_{152} & a_{152}\sin\theta_{152} \\ 0 & \sin\alpha_{152} & \cos\alpha_{152} & d_{152} \\ 0 & 0 & 0 & 1 \end{bmatrix}$$

Joint 153 connects the left little finger Distal Phalanx to the left little finger Middle Phalanx, forming the $5^{th}$ distal interphalangeal joint (DIP). The $d_{153}$ length of the left little finger Digital Phalanx runs through the centroid of the Distal Phalanx from the head of the left little finger Proximal Phalanx to the head of the left little finger Distal Phalanx.

$$A_{153} = \begin{bmatrix} \cos\theta_{153} & -\sin\theta_{153} & 0 & 0 \\ \sin\theta_{153} & \cos\theta_{153} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{153} \\ 0 & 0 & 0 & 1 \end{bmatrix} \begin{bmatrix} 1 & 0 & 0 & a_{153} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{153} & -\sin\alpha_{153} & 0 \\ 0 & \sin\alpha_{153} & \cos\alpha_{153} & 0 \\ 0 & 0 & 0 & 1 \end{bmatrix}$$

$$A_{153} = \begin{bmatrix} \cos\theta_{153} & -\sin\theta_{153}\cos\alpha_{153} & \sin\theta_{153}\sin\alpha_{153} & a_{153}\cos\theta_{153} \\ \sin\theta_{153} & \cos\theta_{153}\cos\alpha_{153} & -\cos\theta_{153}\sin\alpha_{153} & a_{153}\sin\theta_{153} \\ 0 & \sin\alpha_{153} & \cos\alpha_{153} & d_{153} \\ 0 & 0 & 0 & 1 \end{bmatrix}$$

Joint 154 connects the left index finger Middle Phalanx to the left index finger Proximal Phalanx forming the $2^{nd}$ proximal interphalangeal joint (PIP). The $d_{154}$ length of the left index finger Middle Phalanx runs through the centroid of the Middle Phalanx from the head of the left index finger Proximal Phalanx to the head of the left index finger middle phalanx.

$$A_{154} = \begin{bmatrix} \cos\theta_{154} & -\sin\theta_{154} & 0 & 0 \\ \sin\theta_{154} & \cos\theta_{154} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{154} \\ 0 & 0 & 0 & 1 \end{bmatrix} \begin{bmatrix} 1 & 0 & 0 & a_{154} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{154} & -\sin\alpha_{154} & 0 \\ 0 & \sin\alpha_{154} & \cos\alpha_{154} & 0 \\ 0 & 0 & 0 & 1 \end{bmatrix}$$

$$A_{154} = \begin{bmatrix} \cos\theta_{154} & -\sin\theta_{154}\cos\alpha_{154} & \sin\theta_{154}\sin\alpha_{154} & a_{154}\cos\theta_{154} \\ \sin\theta_{154} & \cos\theta_{154}\cos\alpha_{154} & -\cos\theta_{154}\sin\alpha_{154} & a_{154}\sin\theta_{154} \\ 0 & \sin\alpha_{154} & \cos\alpha_{154} & d_{154} \\ 0 & 0 & 0 & 1 \end{bmatrix}$$

Joint 155 connects the left middle finger Middle Phalanx to the left middle finger Proximal Phalanx, forming the $3^{rd}$ proximal interphalangeal joint (PIP). The $d_{155}$ length of the left middle finger Middle Phalanx runs through the centroid of the Middle Phalanx from the head of the left middle finger Proximal Phalanx to the head of the left middle finger Middle Phalanx.

$$A_{155} = \begin{bmatrix} \cos\theta_{155} & -\sin\theta_{155} & 0 & 0 \\ \sin\theta_{155} & \cos\theta_{155} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{155} \\ 0 & 0 & 0 & 1 \end{bmatrix} \begin{bmatrix} 1 & 0 & 0 & a_{155} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{155} & -\sin\alpha_{155} & 0 \\ 0 & \sin\alpha_{155} & \cos\alpha_{155} & 0 \\ 0 & 0 & 0 & 1 \end{bmatrix}$$

$$A_{155} = \begin{bmatrix} \cos\theta_{155} & -\sin\theta_{155}\cos\alpha_{155} & \sin\theta_{155}\sin\alpha_{155} & a_{155}\cos\theta_{155} \\ \sin\theta_{155} & \cos\theta_{155}\cos\alpha_{155} & -\cos\theta_{155}\sin\alpha_{155} & a_{155}\sin\theta_{155} \\ 0 & \sin\alpha_{155} & \cos\alpha_{155} & d_{155} \\ 0 & 0 & 0 & 1 \end{bmatrix}$$

Joint 156 connects the left ring finger Middle Phalanx to the left ring finger Proximal Phalanx, forming the $4^{th}$ proximal interphalangeal joint (PIP). The $d_{156}$ length of the left ring finger Middle Phalanx runs through the centroid of the Middle Phalanx from the head of the left ring finger Proximal Phalanx to the head of the left ring finger Middle Phalanx.

$$A_{156} = \begin{bmatrix} \cos\theta_{156} & -\sin\theta_{156} & 0 & 0 \\ \sin\theta_{156} & \cos\theta_{156} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{156} \\ 0 & 0 & 0 & 1 \end{bmatrix} \begin{bmatrix} 1 & 0 & 0 & a_{156} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{156} & -\sin\alpha_{156} & 0 \\ 0 & \sin\alpha_{156} & \cos\alpha_{156} & 0 \\ 0 & 0 & 0 & 1 \end{bmatrix}$$

$$A_{156} = \begin{bmatrix} \cos\theta_{156} & -\sin\theta_{156}\cos\alpha_{156} & \sin\theta_{156}\sin\alpha_{156} & a_{156}\cos\theta_{156} \\ \sin\theta_{156} & \cos\theta_{156}\cos\alpha_{156} & -\cos\theta_{156}\sin\alpha_{156} & a_{156}\sin\theta_{156} \\ 0 & \sin\alpha_{156} & \cos\alpha_{156} & d_{156} \\ 0 & 0 & 0 & 1 \end{bmatrix}$$

Joint 157 connects the left little finger Middle Phalanx to the left little finger Proximal Phalanx, forming the $5^{th}$ proximal interphalangeal joint (PIP). The $d_{156}$ length of the left little finger Middle Phalanx runs through the centroid of the Middle Phalanx from the head of the left little finger Proximal Phalanx to the head of the left little finger Middle Phalanx.

$$A_{157} = \begin{bmatrix} \cos\theta_{157} & -\sin\theta_{157} & 0 & 0 \\ \sin\theta_{157} & \cos\theta_{157} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{157} \\ 0 & 0 & 0 & 1 \end{bmatrix} \begin{bmatrix} 1 & 0 & 0 & a_{157} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{157} & -\sin\alpha_{157} & 0 \\ 0 & \sin\alpha_{157} & \cos\alpha_{157} & 0 \\ 0 & 0 & 0 & 1 \end{bmatrix}$$

$$A_{157} = \begin{bmatrix} \cos\theta_{157} & -\sin\theta_{157}\cos\alpha_{157} & \sin\theta_{157}\sin\alpha_{157} & a_{157}\cos\theta_{157} \\ \sin\theta_{157} & \cos\theta_{157}\cos\alpha_{157} & -\cos\theta_{157}\sin\alpha_{157} & a_{157}\sin\theta_{157} \\ 0 & \sin\alpha_{157} & \cos\alpha_{157} & d_{157} \\ 0 & 0 & 0 & 1 \end{bmatrix}$$

Joint 158 connects the left thumb Proximal Phalanx to the left thumb Metacarpal in the $1^{st}$ metacarpophalangeal joint (MCP) The $d_{158}$ length of the left thumb Middle Phalanx runs through the centroid of the Middle Proximal Phalanx from the head of the thumb Metacarpal to the head of the thumb Proximal Phalanx.

$$A_{158} = \begin{bmatrix} \cos\theta_{158} & -\sin\theta_{158} & 0 & 0 \\ \sin\theta_{158} & \cos\theta_{158} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{158} \\ 0 & 0 & 0 & 1 \end{bmatrix} \begin{bmatrix} 1 & 0 & 0 & a_{158} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{158} & -\sin\alpha_{158} & 0 \\ 0 & \sin\alpha_{158} & \cos\alpha_{158} & 0 \\ 0 & 0 & 0 & 1 \end{bmatrix}$$

$$A_{158} = \begin{bmatrix} \cos\theta_{158} & -\sin\theta_{158}\cos\alpha_{158} & \sin\theta_{158}\sin\alpha_{158} & a_{158}\cos\theta_{158} \\ \sin\theta_{158} & \cos\theta_{158}\cos\alpha_{158} & -\cos\theta_{158}\sin\alpha_{158} & a_{158}\sin\theta_{158} \\ 0 & \sin\alpha_{158} & \cos\alpha_{158} & d_{158} \\ 0 & 0 & 0 & 1 \end{bmatrix}$$

Joint 159 connects the left index finger Proximal Phalanx to the left index finger Metacarpal in the $2^{nd}$ metacarpophalangeal joint (MCP). The $d_{159}$ length of the left index finger Proximal Phalanx runs through the centroid of the index finger Proximal Phalanx from the head of the index finger Metacarpus to the head of the index finger Proximal Phalanx.

$$A_{159} = \begin{bmatrix} \cos\theta_{159} & -\sin\theta_{159} & 0 & 0 \\ \sin\theta_{159} & \cos\theta_{159} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{159} \\ 0 & 0 & 0 & 1 \end{bmatrix} \begin{bmatrix} 1 & 0 & 0 & a_{159} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{159} & -\sin\alpha_{159} & 0 \\ 0 & \sin\alpha_{159} & \cos\alpha_{159} & 0 \\ 0 & 0 & 0 & 1 \end{bmatrix}$$

$$A_{159} = \begin{bmatrix} \cos\theta_{159} & -\sin\theta_{159}\cos\alpha_{159} & \sin\theta_{159}\sin\alpha_{159} & a_{159}\cos\theta_{159} \\ \sin\theta_{159} & \cos\theta_{159}\cos\alpha_{159} & -\cos\theta_{159}\sin\alpha_{159} & a_{159}\sin\theta_{159} \\ 0 & \sin\alpha_{159} & \cos\alpha_{159} & d_{159} \\ 0 & 0 & 0 & 1 \end{bmatrix}$$

Joint 160 connects the left middle finger Proximal Phalanx to the left middle finger Metacarpal in the $3^{rd}$ metacarpophalangeal joint (MCP). The $d_{160}$ length of the left middle finger Proximal Phalanx runs through the centroid of the left middle finger Proximal Phalanx from the head of the middle finger Metacarpus to the head of the middle finger Proximal Phalanx.

$$A_{160} = \begin{bmatrix} \cos\theta_{160} & -\sin\theta_{160} & 0 & 0 \\ \sin\theta_{160} & \cos\theta_{160} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{160} \\ 0 & 0 & 0 & 1 \end{bmatrix} \begin{bmatrix} 1 & 0 & 0 & a_{160} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{160} & -\sin\alpha_{160} & 0 \\ 0 & \sin\alpha_{160} & \cos\alpha_{160} & 0 \\ 0 & 0 & 0 & 1 \end{bmatrix}$$

$$A_{160} = \begin{bmatrix} \cos\theta_{160} & -\sin\theta_{160}\cos\alpha_{160} & \sin\theta_{160}\sin\alpha_{160} & a_{160}\cos\theta_{160} \\ \sin\theta_{160} & \cos\theta_{160}\cos\alpha_{160} & -\cos\theta_{160}\sin\alpha_{160} & a_{160}\sin\theta_{160} \\ 0 & \sin\alpha_{160} & \cos\alpha_{160} & d_{160} \\ 0 & 0 & 0 & 1 \end{bmatrix}$$

Joint 161 connects the left ring finger Proximal Phalanx to the left ring finger Metacarpal in the $4^{th}$ metacarpophalangeal joint (MCP). The $d_{161}$ length of the left ring finger Proximal Phalanx runs through the centroid of the left ring finger Proximal Phalanx from the head of the ring finger Metacarpus to the head of the ring finger Proximal Phalanx.

$$A_{161} = \begin{bmatrix} \cos\theta_{161} & -\sin\theta_{161} & 0 & 0 \\ \sin\theta_{161} & \cos\theta_{161} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{161} \\ 0 & 0 & 0 & 1 \end{bmatrix} \begin{bmatrix} 1 & 0 & 0 & a_{161} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{161} & -\sin\alpha_{161} & 0 \\ 0 & \sin\alpha_{161} & \cos\alpha_{161} & 0 \\ 0 & 0 & 0 & 1 \end{bmatrix}$$

$$A_{161} = \begin{bmatrix} \cos\theta_{161} & -\sin\theta_{161}\cos\alpha_{161} & \sin\theta_{161}\sin\alpha_{161} & a_{161}\cos\theta_{161} \\ \sin\theta_{161} & \cos\theta_{161}\cos\alpha_{161} & -\cos\theta_{161}\sin\alpha_{161} & a_{161}\sin\theta_{161} \\ 0 & \sin\alpha_{161} & \cos\alpha_{161} & d_{161} \\ 0 & 0 & 0 & 1 \end{bmatrix}$$

Joint 162 connects the left little finger Proximal Phalanx to the left little finger Metacarpal in the $5^{th}$ metacarpophalangeal joint (MCP). The $d_{162}$ length of the left little finger Proximal Phalanx runs through the centroid of the left little finger Proximal Phalanx from the head of the little finger Metacarpus to the head of the little finger Proximal Phalanx.

$$A_{162} = \begin{bmatrix} \cos\theta_{162} & -\sin\theta_{162} & 0 & 0 \\ \sin\theta_{162} & \cos\theta_{162} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{162} \\ 0 & 0 & 0 & 1 \end{bmatrix} \begin{bmatrix} 1 & 0 & 0 & a_{162} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{162} & -\sin\alpha_{162} & 0 \\ 0 & \sin\alpha_{162} & \cos\alpha_{162} & 0 \\ 0 & 0 & 0 & 1 \end{bmatrix}$$

$$A_{162} = \begin{bmatrix} \cos\theta_{162} & -\sin\theta_{162}\cos\alpha_{162} & \sin\theta_{162}\sin\alpha_{162} & a_{162}\cos\theta_{162} \\ \sin\theta_{162} & \cos\theta_{162}\cos\alpha_{162} & -\cos\theta_{162}\sin\alpha_{162} & a_{162}\sin\theta_{162} \\ 0 & \sin\alpha_{162} & \cos\alpha_{162} & d_{162} \\ 0 & 0 & 0 & 1 \end{bmatrix}$$

Joint 163 connects the left thumb Metacarpal to the left Trapezium. The $d_{163}$ length of the left thumb Metacarpal runs through the centroid of the left thumb Metacarpal.

$$A_{163} = \begin{bmatrix} \cos\theta_{163} & -\sin\theta_{163} & 0 & 0 \\ \sin\theta_{163} & \cos\theta_{163} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{163} \\ 0 & 0 & 0 & 1 \end{bmatrix} \begin{bmatrix} 1 & 0 & 0 & a_{163} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{163} & -\sin\alpha_{163} & 0 \\ 0 & \sin\alpha_{163} & \cos\alpha_{163} & 0 \\ 0 & 0 & 0 & 1 \end{bmatrix}$$

$$A_{163} = \begin{bmatrix} \cos\theta_{163} & -\sin\theta_{163}\cos\alpha_{163} & \sin\theta_{163}\sin\alpha_{163} & a_{163}\cos\theta_{163} \\ \sin\theta_{163} & \cos\theta_{163}\cos\alpha_{163} & -\cos\theta_{163}\sin\alpha_{163} & a_{163}\sin\theta_{163} \\ 0 & \sin\alpha_{163} & \cos\alpha_{163} & d_{163} \\ 0 & 0 & 0 & 1 \end{bmatrix}$$

Joint 164 connects the left thumb Metacarpal to the left Index finger Metacarpal. The $d_{164}$ length of the left thumb Metacarpal runs through the centroid of the left thumb Metacarpal, beginning at the head of the left Trapezium, and extending to the head of the left thumb Metacarpal.

$$A_{164} = \begin{bmatrix} \cos\theta_{164} & -\sin\theta_{164} & 0 & 0 \\ \sin\theta_{164} & \cos\theta_{164} & 0 & 0 \\ 0 & 0 & 1 & 0 \\ 0 & 0 & 0 & 1 \end{bmatrix} \text{middle}$$

$$\text{finger} \begin{bmatrix} 1 & 0 & 0 & 0 \\ 0 & 1 & 0 & 0 \\ 0 & 0 & 1 & d_{164} \\ 0 & 0 & 0 & 1 \end{bmatrix} \begin{bmatrix} 1 & 0 & 0 & a_{164} \\ 0 & 1 & 0 & 0 \\ 0 & 0 & 1 & 0 \\ 0 & 0 & 0 & 1 \end{bmatrix} \begin{bmatrix} 1 & 0 & 0 & 0 \\ 0 & \cos\alpha_{164} & -\sin\alpha_{164} & 0 \\ 0 & \sin\alpha_{164} & \cos\alpha_{164} & 0 \\ 0 & 0 & 0 & 1 \end{bmatrix}$$

$$A_{164} = \begin{bmatrix} \cos\theta_{164} & -\sin\theta_{164}\cos\alpha_{164} & \sin\theta_{164}\sin\alpha_{164} & a_{164}\cos\theta_{164} \\ \sin\theta_{164} & \cos\theta_{164}\cos\alpha_{164} & -\cos\theta_{164}\sin\alpha_{164} & a_{164}\sin\theta_{164} \\ 0 & \sin\alpha_{164} & \cos\alpha_{164} & d_{164} \\ 0 & 0 & 0 & 1 \end{bmatrix}$$

Joint 165 connects the left index finger Metacarpal to the left middle finger Metacarpal. The $d_{165}$ length of the left index finger Metacarpal runs through the centroid of the left index finger Metacarpal beginning at the side of the left middle finger Metacarpal.

$$A_{165} = \begin{bmatrix} \cos\theta_{165} & -\sin\theta_{165} & 0 & 0 \\ \sin\theta_{165} & \cos\theta_{165} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{165} \\ 0 & 0 & 0 & 1 \end{bmatrix} \begin{bmatrix} 1 & 0 & 0 & a_{165} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{165} & -\sin\alpha_{165} & 0 \\ 0 & \sin\alpha_{165} & \cos\alpha_{165} & 0 \\ 0 & 0 & 0 & 1 \end{bmatrix}$$

$$A_{165} = \begin{bmatrix} \cos\theta_{165} & -\sin\theta_{165}\cos\alpha_{165} & \sin\theta_{165}\sin\alpha_{165} & a_{165}\cos\theta_{165} \\ \sin\theta_{165} & \cos\theta_{165}\cos\alpha_{165} & -\cos\theta_{165}\sin\alpha_{165} & a_{165}\sin\theta_{165} \\ 0 & \sin\alpha_{165} & \cos\alpha_{165} & d_{165} \\ 0 & 0 & 0 & 1 \end{bmatrix}$$

Joint 166 connects the left middle finger Metacarpal to the left ring finger Metacarpal. The $d_{166}$ length of the left middle finger Metacarpal runs through the left middle finger Metacarpal beginning at the side of the left ring finger Metacarpal to the head of the left middle finger Metacarpal.

$$A_{166} = \begin{bmatrix} \cos\theta_{166} & -\sin\theta_{166} & 0 & 0 \\ \sin\theta_{166} & \cos\theta_{166} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{166} \\ 0 & 0 & 0 & 1 \end{bmatrix} \begin{bmatrix} 1 & 0 & 0 & a_{166} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{166} & -\sin\alpha_{166} & 0 \\ 0 & \sin\alpha_{166} & \cos\alpha_{166} & 0 \\ 0 & 0 & 0 & 1 \end{bmatrix}$$

$$A_{166} = \begin{bmatrix} \cos\theta_{166} & -\sin\theta_{166}\cos\alpha_{166} & \sin\theta_{166}\sin\alpha_{166} & a_{166}\cos\theta_{166} \\ \sin\theta_{166} & \cos\theta_{166}\cos\alpha_{166} & -\cos\theta_{166}\sin\alpha_{166} & a_{166}\sin\theta_{166} \\ 0 & \sin\alpha_{166} & \cos\alpha_{166} & d_{166} \\ 0 & 0 & 0 & 1 \end{bmatrix}$$

Joint 167 connects the left index finger Metacarpal to the Left Trapezium. The $d_{167}$ length of the left index finger Metacarpal runs through the left index finger Metacarpal beginning at the head of the left trapezium to the head of the left index finger Metacarpal.

$$A_{167} = \begin{bmatrix} \cos\theta_{167} & -\sin\theta_{167} & 0 & 0 \\ \sin\theta_{167} & \cos\theta_{167} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{167} \\ 0 & 0 & 0 & 1 \end{bmatrix} \begin{bmatrix} 1 & 0 & 0 & a_{167} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{167} & -\sin\alpha_{167} & 0 \\ 0 & \sin\alpha_{167} & \cos\alpha_{167} & 0 \\ 0 & 0 & 0 & 1 \end{bmatrix}$$

$$A_{167} = \begin{bmatrix} \cos\theta_{167} & -\sin\theta_{167}\cos\alpha_{167} & \sin\theta_{167}\sin\alpha_{167} & a_{167}\cos\theta_{167} \\ \sin\theta_{167} & \cos\theta_{167}\cos\alpha_{167} & -\cos\theta_{167}\sin\alpha_{167} & a_{167}\sin\theta_{167} \\ 0 & \sin\alpha_{167} & \cos\alpha_{167} & d_{167} \\ 0 & 0 & 0 & 1 \end{bmatrix}$$

Joint 168 connects the left index finger Metacarpal to the left Trapezoid. The $d_{167}$ length of the left index finger Metacarpal runs through the left index finger Metacarpal beginning at the head of the left trapezoid to the head of the left index finger Metacarpal.

$$A_{168} = \begin{bmatrix} \cos\theta_{168} & -\sin\theta_{168} & 0 & 0 \\ \sin\theta_{168} & \cos\theta_{168} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{168} \\ 0 & 0 & 0 & 1 \end{bmatrix} \begin{bmatrix} 1 & 0 & 0 & a_{168} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{168} & -\sin\alpha_{168} & 0 \\ 0 & \sin\alpha_{168} & \cos\alpha_{168} & 0 \\ 0 & 0 & 0 & 1 \end{bmatrix}$$

$$A_{168} = \begin{bmatrix} \cos\theta_{168} & -\sin\theta_{168}\cos\alpha_{168} & \sin\theta_{168}\sin\alpha_{168} & a_{168}\cos\theta_{168} \\ \sin\theta_{168} & \cos\theta_{168}\cos\alpha_{168} & -\cos\theta_{168}\sin\alpha_{168} & a_{168}\sin\theta_{168} \\ 0 & \sin\alpha_{168} & \cos\alpha_{168} & d_{168} \\ 0 & 0 & 0 & 1 \end{bmatrix}$$

Joint 169 connects the left middle finger to the left Trapezoid. The $d_{169}$ length of the left index finger Metacarpal runs through the left index finger Metacarpal beginning at the head of the left trapezoid to the head of the left index finger Metacarpal.

$$A_{169} = \begin{bmatrix} \cos\theta_{169} & -\sin\theta_{169} & 0 & 0 \\ \sin\theta_{169} & \cos\theta_{169} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{169} \\ 0 & 0 & 0 & 1 \end{bmatrix} \begin{bmatrix} 1 & 0 & 0 & a_{169} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{169} & -\sin\alpha_{169} & 0 \\ 0 & \sin\alpha_{169} & \cos\alpha_{169} & 0 \\ 0 & 0 & 0 & 1 \end{bmatrix}$$

$$A_{169} = \begin{bmatrix} \cos\theta_{169} & -\sin\theta_{169}\cos\alpha_{169} & \sin\theta_{169}\sin\alpha_{169} & a_{169}\cos\theta_{169} \\ \sin\theta_{169} & \cos\theta_{169}\cos\alpha_{169} & -\cos\theta_{169}\sin\alpha_{169} & a_{169}\sin\theta_{169} \\ 0 & \sin\alpha_{169} & \cos\alpha_{169} & d_{169} \\ 0 & 0 & 0 & 1 \end{bmatrix}$$

Joint 170 connects the left middle finger Metacarpal to the left Capitate. The $d_{170}$ length of the left index finger Metacarpal runs through the left index finger Metacarpal beginning at the head of the left Capitate to the head of the left index finger Metacarpal.

$$A_{170} = \begin{bmatrix} \cos\theta_{170} & -\sin\theta_{170} & 0 & 0 \\ \sin\theta_{170} & \cos\theta_{170} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{170} \\ 0 & 0 & 0 & 1 \end{bmatrix} \begin{bmatrix} 1 & 0 & 0 & a_{170} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{170} & -\sin\alpha_{170} & 0 \\ 0 & \sin\alpha_{170} & \cos\alpha_{170} & 0 \\ 0 & 0 & 0 & 1 \end{bmatrix}$$

$$A_{170} = \begin{bmatrix} \cos\theta_{170} & -\sin\theta_{170}\cos\alpha_{170} & \sin\theta_{170}\sin\alpha_{170} & a_{170}\cos\theta_{170} \\ \sin\theta_{170} & \cos\theta_{170}\cos\alpha_{170} & -\cos\theta_{170}\sin\alpha_{170} & a_{170}\sin\theta_{170} \\ 0 & \sin\alpha_{170} & \cos\alpha_{170} & d_{170} \\ 0 & 0 & 0 & 1 \end{bmatrix}$$

Joint 171 connects the left middle finger Metacarpal to the left ring finger Metacarpal. The $d_{171}$ length of the left middle finger Metacarpal runs through the left middle finger Metacarpal beginning at the head of the left Metacarpal to the head of the left middle finger Metacarpal.

$$A_{171} = \begin{bmatrix} \cos\theta_{171} & -\sin\theta_{171} & 0 & 0 \\ \sin\theta_{171} & \cos\theta_{171} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{171} \\ 0 & 0 & 0 & 1 \end{bmatrix} \begin{bmatrix} 1 & 0 & 0 & a_{171} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{171} & -\sin\alpha_{171} & 0 \\ 0 & \sin\alpha_{171} & \cos\alpha_{171} & 0 \\ 0 & 0 & 0 & 1 \end{bmatrix}$$

$$A_{171} = \begin{bmatrix} \cos\theta_{171} & -\sin\theta_{171}\cos\alpha_{171} & \sin\theta_{171}\sin\alpha_{171} & a_{171}\cos\theta_{171} \\ \sin\theta_{171} & \cos\theta_{171}\cos\alpha_{171} & -\cos\theta_{171}\sin\alpha_{171} & a_{171}\sin\theta_{171} \\ 0 & \sin\alpha_{171} & \cos\alpha_{171} & d_{171} \\ 0 & 0 & 0 & 1 \end{bmatrix}$$

Joint 172 connects the left ring finger Metacarpal to the Left Capitate. The $d_{172}$ length of the left ring finger Metacarpal runs through the left middle finger Metacarpal beginning at the head of the left Metacarpal to the head of the left Capitate.

$$A_{172} = \begin{bmatrix} \cos\theta_{172} & -\sin\theta_{172} & 0 & 0 \\ \sin\theta_{172} & \cos\theta_{172} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{172} \\ 0 & 0 & 0 & 1 \end{bmatrix} \begin{bmatrix} 1 & 0 & 0 & a_{172} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{172} & -\sin\alpha_{172} & 0 \\ 0 & \sin\alpha_{172} & \cos\alpha_{172} & 0 \\ 0 & 0 & 0 & 1 \end{bmatrix}$$

$$A_{172} = \begin{bmatrix} \cos\theta_{172} & -\sin\theta_{172}\cos\alpha_{172} & \sin\theta_{172}\sin\alpha_{172} & a_{172}\cos\theta_{172} \\ \sin\theta_{172} & \cos\theta_{172}\cos\alpha_{172} & -\cos\theta_{172}\sin\alpha_{172} & a_{172}\sin\theta_{172} \\ 0 & \sin\alpha_{172} & \cos\alpha_{172} & d_{172} \\ 0 & 0 & 0 & 1 \end{bmatrix}$$

Joint 173 connects the left ring finger Metacarpal to the left little finger Metacarpal. The $d_{173}$ length of the left ring finger Metacarpal runs through the left middle finger Metacarpal beginning at the touchpoint of the left little finger Metacarpal to the touchpoint on the little finger Metacarpal.

$$A_{173} = \begin{bmatrix} \cos\theta_{173} & -\sin\theta_{173} & 0 & 0 \\ \sin\theta_{173} & \cos\theta_{173} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{173} \\ 0 & 0 & 0 & 1 \end{bmatrix} \begin{bmatrix} 1 & 0 & 0 & a_{173} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{173} & -\sin\alpha_{173} & 0 \\ 0 & \sin\alpha_{173} & \cos\alpha_{173} & 0 \\ 0 & 0 & 0 & 1 \end{bmatrix}$$

$$A_{173} = \begin{bmatrix} \cos\theta_{173} & -\sin\theta_{173}\cos\alpha_{173} & \sin\theta_{173}\sin\alpha_{173} & a_{173}\cos\theta_{173} \\ \sin\theta_{173} & \cos\theta_{173}\cos\alpha_{173} & -\cos\theta_{173}\sin\alpha_{173} & a_{173}\sin\theta_{173} \\ 0 & \sin\alpha_{173} & \cos\alpha_{173} & d_{173} \\ 0 & 0 & 0 & 1 \end{bmatrix}$$

Joint 174 connects the left ring finger Metacarpal to the left Hamate. The $d_{174}$ length of the left ring finger Metacarpal runs through the left middle finger Metacarpal beginning at the touchpoint of the left little finger Metacarpal to the touchpoint on the left Hamate.

$$A_{174} = \begin{bmatrix} \cos\theta_{174} & -\sin\theta_{174} & 0 & 0 \\ \sin\theta_{174} & \cos\theta_{174} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{174} \\ 0 & 0 & 0 & 1 \end{bmatrix} \begin{bmatrix} 1 & 0 & 0 & a_{174} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{174} & -\sin\alpha_{174} & 0 \\ 0 & \sin\alpha_{174} & \cos\alpha_{174} & 0 \\ 0 & 0 & 0 & 1 \end{bmatrix}$$

$$A_{174} = \begin{bmatrix} \cos\theta_{174} & -\sin\theta_{174}\cos\alpha_{174} & \sin\theta_{174}\sin\alpha_{174} & a_{173}\cos\theta_{174} \\ \sin\theta_{174} & \cos\theta_{174}\cos\alpha_{174} & -\cos\theta_{173}\sin\alpha_{174} & a_{173}\sin\theta_{174} \\ 0 & \sin\alpha_{174} & \cos\alpha_{174} & d_{174} \\ 0 & 0 & 0 & 1 \end{bmatrix}$$

Joint 175 connects the left little finger Metacarpal to the left Hamate. The $d_{175}$ length of the left little finger Metacarpal runs through the left little finger Metacarpal beginning at the touchpoint of the left little finger Metacarpal to the touchpoint on the left Hamate.

$$A_{175} = \begin{bmatrix} \cos\theta_{175} & -\sin\theta_{175} & 0 & 0 \\ \sin\theta_{175} & \cos\theta_{175} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{175} \\ 0 & 0 & 0 & 1 \end{bmatrix} \begin{bmatrix} 1 & 0 & 0 & a_{175} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{175} & -\sin\alpha_{175} & 0 \\ 0 & \sin\alpha_{175} & \cos\alpha_{175} & 0 \\ 0 & 0 & 0 & 1 \end{bmatrix}$$

$$A_{175} = \begin{bmatrix} \cos\theta_{175} & -\sin\theta_{175}\cos\alpha_{175} & \sin\theta_{175}\sin\alpha_{175} & a_{175}\cos\theta_{175} \\ \sin\theta_{175} & \cos\theta_{175}\cos\alpha_{175} & -\cos\theta_{175}\sin\alpha_{175} & a_{175}\sin\theta_{175} \\ 0 & \sin\alpha_{175} & \cos\alpha_{175} & d_{175} \\ 0 & 0 & 0 & 1 \end{bmatrix}$$

Joint 176 connects the left Trapezium to the left Trapezoid. The $d_{176}$ length of the left Trapezium runs through the left Trapezium beginning at the touchpoint of the left Trapezoid to the touchpoint on the left Trapezium.

$$A_{176} = \begin{bmatrix} \cos\theta_{176} & -\sin\theta_{176} & 0 & 0 \\ \sin\theta_{176} & \cos\theta_{176} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{176} \\ 0 & 0 & 0 & 1 \end{bmatrix} \begin{bmatrix} 1 & 0 & 0 & a_{176} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{176} & -\sin\alpha_{176} & 0 \\ 0 & \sin\alpha_{176} & \cos\alpha_{176} & 0 \\ 0 & 0 & 0 & 1 \end{bmatrix}$$

$$A_{176} = \begin{bmatrix} \cos\theta_{176} & -\sin\theta_{176}\cos\alpha_{176} & \sin\theta_{176}\sin\alpha_{176} & a_{176}\cos\theta_{176} \\ \sin\theta_{176} & \cos\theta_{176}\cos\alpha_{176} & -\cos\theta_{176}\sin\alpha_{176} & a_{176}\sin\theta_{176} \\ 0 & \sin\alpha_{176} & \cos\alpha_{176} & d_{176} \\ 0 & 0 & 0 & 1 \end{bmatrix}$$

Joint 177 connects the left Trapezium to the left Scaphoid. The $d_{177}$ length of the left Trapezium runs from the left head of the Scaphoid to the left head of the Trapezium.

$$A_{177} = \begin{bmatrix} \cos\theta_{177} & -\sin\theta_{177} & 0 & 0 \\ \sin\theta_{177} & \cos\theta_{177} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{177} \\ 0 & 0 & 0 & 1 \end{bmatrix} \begin{bmatrix} 1 & 0 & 0 & a_{177} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{177} & -\sin\alpha_{177} & 0 \\ 0 & \sin\alpha_{177} & \cos\alpha_{177} & 0 \\ 0 & 0 & 0 & 1 \end{bmatrix}$$

$$A_{177} = \begin{bmatrix} \cos\theta_{177} & -\sin\theta_{177}\cos\alpha_{177} & \sin\theta_{177}\sin\alpha_{177} & a_{177}\cos\theta_{177} \\ \sin\theta_{177} & \cos\theta_{177}\cos\alpha_{177} & -\cos\theta_{177}\sin\alpha_{177} & a_{177}\sin\theta_{177} \\ 0 & \sin\alpha_{177} & \cos\alpha_{177} & d_{177} \\ 0 & 0 & 0 & 1 \end{bmatrix}$$

Joint 178 connects the left Trapezoid to the left Capitate. The $d_{178}$ length of the left Trapezoid runs from the left head of the Capitate to the left head of the Trapezoid.

$$A_{178} = \begin{bmatrix} \cos\theta_{178} & -\sin\theta_{178} & 0 & 0 \\ \sin\theta_{178} & \cos\theta_{178} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{178} \\ 0 & 0 & 0 & 1 \end{bmatrix} \begin{bmatrix} 1 & 0 & 0 & a_{178} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{178} & -\sin\alpha_{178} & 0 \\ 0 & \sin\alpha_{178} & \cos\alpha_{178} & 0 \\ 0 & 0 & 0 & 1 \end{bmatrix}$$

$$A_{178} = \begin{bmatrix} \cos\theta_{178} & -\sin\theta_{178}\cos\alpha_{178} & \sin\theta_{178}\sin\alpha_{178} & a_{178}\cos\theta_{178} \\ \sin\theta_{178} & \cos\theta_{175}\cos\alpha_{178} & -\cos\theta_{178}\sin\alpha_{178} & a_{178}\sin\theta_{178} \\ 0 & \sin\alpha_{178} & \cos\alpha_{178} & d_{178} \\ 0 & 0 & 0 & 1 \end{bmatrix}$$

Joint 179 connects the left Trapezoid to the left Scaphoid. The $d_{179}$ length of the left Trapezoid runs from the left head of the Scaphoid to the left head of the Trapezoid.

$$A_{179} = \begin{bmatrix} \cos\theta_{179} & -\sin\theta_{179} & 0 & 0 \\ \sin\theta_{179} & \cos\theta_{179} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{179} \\ 0 & 0 & 0 & 1 \end{bmatrix} \begin{bmatrix} 1 & 0 & 0 & a_{179} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{179} & -\sin\alpha_{179} & 0 \\ 0 & \sin\alpha_{179} & \cos\alpha_{179} & 0 \\ 0 & 0 & 0 & 1 \end{bmatrix}$$

$$A_{179} = \begin{bmatrix} \cos\theta_{179} & -\sin\theta_{179}\cos\alpha_{179} & \sin\theta_{179}\sin\alpha_{179} & a_{179}\cos\theta_{179} \\ \sin\theta_{179} & \cos\theta_{179}\cos\alpha_{179} & -\cos\theta_{179}\sin\alpha_{179} & a_{179}\sin\theta_{179} \\ 0 & \sin\alpha_{179} & \cos\alpha_{179} & d_{179} \\ 0 & 0 & 0 & 1 \end{bmatrix}$$

Joint 180 connects the left Capitate to the left Hamate. The $d_{180}$ length of the left Capitate runs from the left head of the Capitate to the left head of the Hamate.

$$A_{180} = \begin{bmatrix} \cos\theta_{180} & -\sin\theta_{180} & 0 & 0 \\ \sin\theta_{180} & \cos\theta_{180} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{180} \\ 0 & 0 & 0 & 1 \end{bmatrix} \begin{bmatrix} 1 & 0 & 0 & a_{180} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{180} & -\sin\alpha_{180} & 0 \\ 0 & \sin\alpha_{180} & \cos\alpha_{180} & 0 \\ 0 & 0 & 0 & 1 \end{bmatrix}$$

$$A_{180} = \begin{bmatrix} \cos\theta_{180} & -\sin\theta_{180}\cos\alpha_{180} & \sin\theta_{180}\sin\alpha_{180} & a_{180}\cos\theta_{180} \\ \sin\theta_{180} & \cos\theta_{180}\cos\alpha_{180} & -\cos\theta_{180}\sin\alpha_{180} & a_{180}\sin\theta_{180} \\ 0 & \sin\alpha_{180} & \cos\alpha_{180} & d_{180} \\ 0 & 0 & 0 & 1 \end{bmatrix}$$

Joint 181 connects the left Hamate to the left Triquetral. The $d_{181}$ length of the left Hamate runs from the left head of the Triquetral to the left head of the Hamate.

$$A_{181} = \begin{bmatrix} \cos\varphi_{181} & -\sin\varphi_{181} & 0 & 0 \\ \sin\varphi_{181} & \cos\varphi_{181} & 0 & 0 \\ 0 & 0 & 1 & 0 \\ 0 & 0 & 0 & 1 \end{bmatrix} \begin{bmatrix} \cos\theta_{181} & 0 & \sin\theta_{181} & 0 \\ 0 & 1 & 0 & 0 \\ -\sin\theta_{181} & 0 & \cos\theta_{181} & 0 \\ 0 & 0 & 0 & 1 \end{bmatrix}$$

$$\begin{bmatrix} 1 & 0 & 0 & 0 \\ 0 & \cos\psi_{181} & -\sin\varphi_{181} & 0 \\ 0 & \sin\varphi_{181} & \cos\varphi_{181} & 0 \\ 0 & 0 & 0 & 1 \end{bmatrix}$$

$$A_{181} = \begin{bmatrix} \cos\theta_{181} & -\sin\theta_{181}\cos\alpha_{181} & \sin\theta_{181}\sin\alpha_{181} & a_{181}\cos\theta_{181} \\ \sin\theta_{181} & \cos\theta_{181}\cos\alpha_{181} & -\cos\theta_{181}\sin\alpha_{181} & a_{181}\sin\theta_{181} \\ 0 & \sin\alpha_{181} & \cos\alpha_{181} & d_{181} \\ 0 & 0 & 0 & 1 \end{bmatrix}$$

Joint 182 connects the left Triquetral to the left Lunate. The $d_{182}$ length of the left Lunate runs from the left head of the Scaphoid to the left head of the Lunate.

$$A_{182} = \begin{bmatrix} \cos\varphi_{182} & -\sin\varphi_{182} & 0 & 0 \\ \sin\varphi_{182} & \cos\varphi_{182} & 0 & 0 \\ 0 & 0 & 1 & 0 \\ 0 & 0 & 0 & 1 \end{bmatrix} \begin{bmatrix} \cos\theta_{182} & 0 & \sin\theta_{182} & 0 \\ 0 & 1 & 0 & 0 \\ -\sin\theta_{182} & 0 & \cos\theta_{182} & 0 \\ 0 & 0 & 0 & 1 \end{bmatrix}$$

$$\begin{bmatrix} 1 & 0 & 0 & 0 \\ 0 & \cos\psi_{182} & -\sin\varphi_{182} & 0 \\ 0 & \sin\varphi_{182} & \cos\varphi_{182} & 0 \\ 0 & 0 & 0 & 1 \end{bmatrix}$$

$$A_{182} = \begin{bmatrix} \cos\theta_{182} & -\sin\theta_{182}\cos\alpha_{182} & \sin\theta_{182}\sin\alpha_{182} & a_{182}\cos\theta_{182} \\ \sin\theta_{182} & \cos\theta_{182}\cos\alpha_{182} & -\cos\theta_{182}\sin\alpha_{182} & a_{182}\sin\theta_{182} \\ 0 & \sin\alpha_{182} & \cos\alpha_{182} & d_{182} \\ 0 & 0 & 0 & 1 \end{bmatrix}$$

Joint 183 connects the left Lunate to the left Capitate. The $d_{183}$ length of the left Lunate runs from the left head of the Lunate to the left head of the Capitate.

$$A_{183} = \begin{bmatrix} \cos\theta_{183} & -\sin\theta_{183} & 0 & 0 \\ \sin\theta_{183} & \cos\theta_{183} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{183} \\ 0 & 0 & 0 & 1 \end{bmatrix} \begin{bmatrix} 1 & 0 & 0 & a_{183} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{183} & -\sin\alpha_{183} & 0 \\ 0 & \sin\alpha_{183} & \cos\alpha_{183} & 0 \\ 0 & 0 & 0 & 1 \end{bmatrix}$$

$$A_{183} = \begin{bmatrix} \cos\theta_{183} & -\sin\theta_{183}\cos\alpha_{183} & \sin\theta_{183}\sin\alpha_{183} & a_{183}\cos\theta_{183} \\ \sin\theta_{183} & \cos\theta_{183}\cos\alpha_{183} & -\cos\theta_{183}\sin\alpha_{183} & a_{183}\sin\theta_{183} \\ 0 & \sin\alpha_{183} & \cos\alpha_{183} & d_{183} \\ 0 & 0 & 0 & 1 \end{bmatrix}$$

Joint 184 connects the left Capitate to the left Scaphoid. The $d_{184}$ length of the left Capitate runs from the left head of the Scaphoid to the head of the Scaphoid.

$$A_{184} = \begin{bmatrix} \cos\varphi_{184} & -\sin\varphi_{184} & 0 & 0 \\ \sin\varphi_{184} & \cos\varphi_{184} & 0 & 0 \\ 0 & 0 & 1 & 0 \\ 0 & 0 & 0 & 1 \end{bmatrix} \begin{bmatrix} \cos\theta_{184} & 0 & \sin\theta_{184} & 0 \\ 0 & 1 & 0 & 0 \\ -\sin\theta_{184} & 0 & \cos\theta_{184} & 0 \\ 0 & 0 & 0 & 1 \end{bmatrix}$$

$$\begin{bmatrix} 1 & 0 & 0 & 0 \\ 0 & \cos\psi_{184} & -\sin\varphi_{184} & 0 \\ 0 & \sin\varphi_{184} & \cos\varphi_{184} & 0 \\ 0 & 0 & 0 & 1 \end{bmatrix}$$

$$A_{184} = \begin{bmatrix} \cos\theta_{184} & -\sin\theta_{184}\cos\alpha_{184} & \sin\theta_{184}\sin\alpha_{184} & a_{184}\cos\theta_{184} \\ \sin\theta_{184} & \cos\theta_{184}\cos\alpha_{184} & -\cos\theta_{184}\sin\alpha_{184} & a_{184}\sin\theta_{184} \\ 0 & \sin\alpha_{184} & \cos\alpha_{184} & d_{184} \\ 0 & 0 & 0 & 1 \end{bmatrix}$$

Joint 185 connects the left Scaphoid to the left Radius. The $d_{185}$ length of the left Scaphoid runs from the left head of the left Radius to the head of the Radius.

$$A_{185} = \begin{bmatrix} \cos\theta_{185} & -\sin\theta_{185} & 0 & 0 \\ \sin\theta_{185} & \cos\theta_{185} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{185} \\ 0 & 0 & 0 & 1 \end{bmatrix} \begin{bmatrix} 1 & 0 & 0 & a_{185} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{185} & -\sin\alpha_{185} & 0 \\ 0 & \sin\alpha_{185} & \cos\alpha_{185} & 0 \\ 0 & 0 & 0 & 1 \end{bmatrix}$$

$$A_{185} = \begin{bmatrix} \cos\theta_{185} & -\sin\theta_{185}\cos\alpha_{185} & \sin\theta_{185}\sin\alpha_{185} & a_{185}\cos\theta_{185} \\ \sin\theta_{185} & \cos\theta_{185}\cos\alpha_{185} & -\cos\theta_{185}\sin\alpha_{185} & a_{185}\sin\theta_{185} \\ 0 & \sin\alpha_{185} & \cos\alpha_{185} & d_{185} \\ 0 & 0 & 0 & 1 \end{bmatrix}$$

Joint 186 connects the left Radius to the left Ulna. The $d_{186}$ length of the left Radius runs from the left head of the Scaphoid to the left head of the Trapezium.

$$A_{186} = \begin{bmatrix} \cos\theta_{186} & -\sin\theta_{186} & 0 & 0 \\ \sin\theta_{186} & \cos\theta_{186} & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_{186} \\ 0 & 0 & 0 & 1 \end{bmatrix} \begin{bmatrix} 1 & 0 & 0 & a_{186} \\ 0 & 1 & 0 & 0 \\ 0 & 0 & 1 & 0 \\ 0 & 0 & 0 & 1 \end{bmatrix}$$

$$\begin{bmatrix} 1 & 0 & 0 & 0 \\ 0 & \cos\alpha_{186} & -\sin\alpha_{186} & 0 \\ 0 & \sin\alpha_{186} & \cos\alpha_{186} & 0 \\ 0 & 0 & 0 & 1 \end{bmatrix}$$

$$A_{186} = \begin{bmatrix} \cos\theta_{186} & -\sin\theta_{186}\cos\alpha_{186} & \sin\theta_{186}\sin\alpha_{186} & a_{186}\cos\theta_{186} \\ \sin\theta_{186} & \cos\theta_{186}\cos\alpha_{186} & -\cos\theta_{186}\sin\alpha_{186} & a_{186}\sin\theta_{186} \\ 0 & \sin\alpha_{186} & \cos\alpha_{186} & d_{186} \\ 0 & 0 & 0 & 1 \end{bmatrix}$$

Joint 187 connects the left Ulna to the left Lunate. The $d_{187}$ length of the left Ulna runs from the left head of the Ulna to the left head of the Lunate.

$$A_{187} = \begin{bmatrix} \cos\varphi_{187} & -\sin\varphi_{187} & 0 & 0 \\ \sin\varphi_{187} & \cos\varphi_{187} & 0 & 0 \\ 0 & 0 & 1 & 0 \\ 0 & 0 & 0 & 1 \end{bmatrix} \begin{bmatrix} \cos\theta_{187} & 0 & \sin\theta_{187} & 0 \\ 0 & 1 & 0 & 0 \\ -\sin\theta_{187} & 0 & \cos\theta_{187} & 0 \\ 0 & 0 & 0 & 1 \end{bmatrix}$$

$$\begin{bmatrix} 1 & 0 & 0 & 0 \\ 0 & \cos\psi_{187} & -\sin\varphi_{187} & 0 \\ 0 & \sin\varphi_{187} & \cos\varphi_{187} & 0 \\ 0 & 0 & 0 & 1 \end{bmatrix}$$

$$A_{187} = \begin{bmatrix} \cos\theta_{187} & -\sin\theta_{187}\cos\alpha_{187} & \sin\theta_{187}\sin\alpha_{187} & a_{187}\cos\theta_{187} \\ \sin\theta_{187} & \cos\theta_{187}\cos\alpha_{187} & -\cos\theta_{187}\sin\alpha_{187} & a_{187}\sin\theta_{187} \\ 0 & \sin\alpha_{187} & \cos\alpha_{187} & d_{187} \\ 0 & 0 & 0 & 1 \end{bmatrix}$$

The above matrices and the model that uses these can be stored in one or more databases of the system and can be used in the determination of a patient's condition or the progression of any conditions the patient may have. In addition, the above matrices and model can be used to determine, in conjunction with data from the foot based data gathering device(s), skeletal joint angles, force vectors, and the propagation of such force vectors through the various components of the skeletal/joint system. As well, the above model and matrices can be used to determine forces at each of the various joints and to interpret these forces into joint motions that indicate normalization of propagated force vectors through the kinematic chain. These can then be used to update/create/adjust a kinematic model specific to each individual/patient.

The system of the present invention can also use the above matrices and model to create and update a fully populated kinematic model for a specific user/patient. This can be done when the user/patient initially uses the system and baseline data for that user/patient is gathered. Information obtained during registration/initial use of the system may include the sensor data from the data collection sensors obtained when the user first activates the sensor package. As should be clear, to gather baseline/initial data for a user, the user takes a fixed number of steps and the data gathered for these steps can form the basis for a baseline data set or biometric loop signature.

The system can also include one or more mechanisms for ingesting pressure map data, pressure loop data, thermal map data, thermal loop data, GPS receiver data, and 9-degree of freedom Inertial Navigation System data. Such data can then be used with a pose estimation software module that may be internal or external to the system of the present invention.

Once the system has the baseline data and one or more data sets obtained subsequent to the gathering of the baseline data, the one or more data sets can be compared to the baseline data. This may involve comparing the original registration kinematic model (the base kinematic chain model for a specific individual) to a currently obtained kinematic model (for the same individual) to determine gait differences between the original baseline data and any subsequent data sets. Gait differences may include kinematic joint specific changes in rotation. These gait differences may be used to update the individual's kinematic model based on the gait-based sensor data interpreted as force vectors through the kinematic model.

It should be clear that loop data is reflective of all gait based biometric contributors including foot shape characteristics, foot type characteristic, foot placement characteristic, weight and load bearing weight, step count, step length, stride length, stride to stride variability, cadence, foot to floor forces, center of force, foot distance apart (instantaneous, average and standard deviation), plantar pressure distribution (instantaneous, average and standard deviation), and plantar peak pressure distribution (instantaneous, average and standard deviation). Loop data characteristics of the biometric signature includes hidden contributors such as those described in the kinematic chain model and any change in the kinematic chain (such as, for example, an ankle injury, toe, knee or hip injury or impairment from disease such as arthritis) will adversely affect the loop data formations of the biometric signature. Such adverse effects on the loop data formations will therefore signal an abnormality indicative of a regression or progression of a disease, injury, or sickness or the onset of a new condition. As noted in this disclosure, such disease, injury, sickness, or new condition would be provisioned by way of a distributed data analysis system using machine learning and artificial intelligence methods and techniques. An example of one human stride represents the correlation of loop biometric signature data (the resulting biometric loop signature data following the steps illustrated in FIGS. 3, 4, 5, 6, 7, and 8), and the kinematic chain model is described below:

(i) Movement during swing phase—the shoulder extends, the spine rotates right, the pelvis rotates left (passive), the hip flexes, the knee flexes, then extends, the ankle dorsiflexes, the foot supination (inversion) and the toes extend.

(ii) Static Position at initial swing—the shoulder is flexed, the spine is rotated left, the pelvis is rotated right, the hip is slightly extended and internally rotated, the knee is slightly flexed, the ankle is fully plantarflexed, the foot is supinated, and the toes are slightly flexed.

(iii) Static Position at Midswing—the shoulder is neutral, the spine is neutral, the pelvis is neutral, the hip is neutral, the knee is flexed 60-90°, the ankle is plantar flexed to neutral, the foot is neutral, and the toes are slightly extended.

(iv) Static Position at Terminal Swing—the shoulder is extended, the spine is rotated right, the pelvis is rotated left, the hip is flexed and externally rotated, the knee is fully extended, the ankle is fully dorsiflexed, the foot is neutral, and the toes are slightly extended.

(v) Static Position at Toe-Off—the shoulder is flexed, the pelvis is rotated right, the hip is fully extended and internally rotated, the knee is fully extended, the ankle is plantarflexed, the foot is fully supinated, and the toes are fully extended.

As noted in this disclosure, a gait-based data analysis system that includes the kinematic chain model explained and noted above allows for a continued and fulsome analysis of human movement and mobility. In addition, it also allows for a determination and monitoring of physiological and behavioral contributors to normal gait and to gait abnormalities, thereby leading to highly individualized gait-based biometric analysis.

The system may also provide some user interface enhancements to allow medical/health personnel to view any changes in the patient's gait/data. As an example, the user interface enhancements may include a color coding based mechanism that allows the medical/health personnel to observe/see a dynamic view of the original registration kinematic model (i.e., the base kinematic chain model) in conjunction with a current version of the individual's kinematic model (i.e., a kinematic chain model derived from a later received data set). The color coding based mechanism can then be used to highlight/identify differences between the two models.

The system may also include other user interface enhancements that allow health/medical personnel to view, dynamically, a current kinematic model for an individual with one or more gait-base kinematic models for specific gait types. These gait types may include: nominal gait models, pain models, injury models, surgery models, weakness models, balance deficit models, pronation models, supination models, over pronation models, and over supination models.

In addition to the above, the system may be used to assess a user/patient's gait pattern based on the current kinematic model. The gait pattern may be determined to be one of: Normal Gait Patterns, Spastic Paraparetic Gait Patterns, Cerebellar ataxias Gait Patterns, Parkinsonian Gait Patterns, Frontal Gait Patterns, Antalgic Gait Patterns, Trendelenburg Gait Patterns, Rheumatoid Gait Patterns, Sensory Gait Patterns, Hemiplegic Gait Patterns, Diplegic Gait Patterns, Myopathic Gait Patterns, Neuropathic Gait Patterns, Flexed Knee Gait Patterns, Cautious Gait Patterns, Hypotonic Gait Patterns, Spastic Gait Patterns, Dyskinetic Gait Disorder Patterns, Dementia Gait Patterns, Diabetic Gait Patterns, Flexed Knee Gait Patterns, Cautious Gait Patterns, Hypotonic Gait Patterns, Spastic Gait Patterns, Vestibular Gait Patterns, and Alzheimer's Gait Patterns.

It should be clear that the systems and methods of the present invention may use machine learning techniques and artificial intelligence techniques and subsystems to perform continuous analysis of kinematic contributors to a user/patient's gait. These kinematic contributors may include all 26 bones and 31 joints in each foot and ankle, up through the lower leg, upper leg, pelvis, sacral vertebrae, and lumbar vertebrae.

The user/patient's gait and the correlation of these contributors to multiple conditions, environments, and surrounding circumstances can be determined using the present invention's systems and methods. These conditions, environments, and surrounding circumstances may include disease, injury and sickness, rehabilitation, therapeutics, and effects of prescribed pharmacologies.

Regarding the programming or storage of the signature or characteristic data into the system, this is preferably done when the user first registers and wears the insole component of the system. This first data set can provide a baseline set of data to be used in comparison with subsequent data sets. This is done by having the user use the insole/sensor module by taking a specific number of normal steps. These steps are then captured in the system and are stored as signature/characteristic or baseline data. Once stored, the signature data can be retrieved and various characteristics of the signature data (by way of the signature loop) can be determined as described above. As described above, the signature data stored may take any number of forms. The signature data may be the raw data gathered from the user when s/he took the specific number of normal steps. Alternatively, the signature data may be the filtered version of the raw data or it may be the various characteristics of the various possible signature loops. Also, instead of the raw data which forms the waveforms, the waveforms themselves may be stored as signature data. The signature data may take any form as long as the characteristics of the signature loops may be derived from or be extracted from the signature/characteristic/baseline data.

Figure 9:
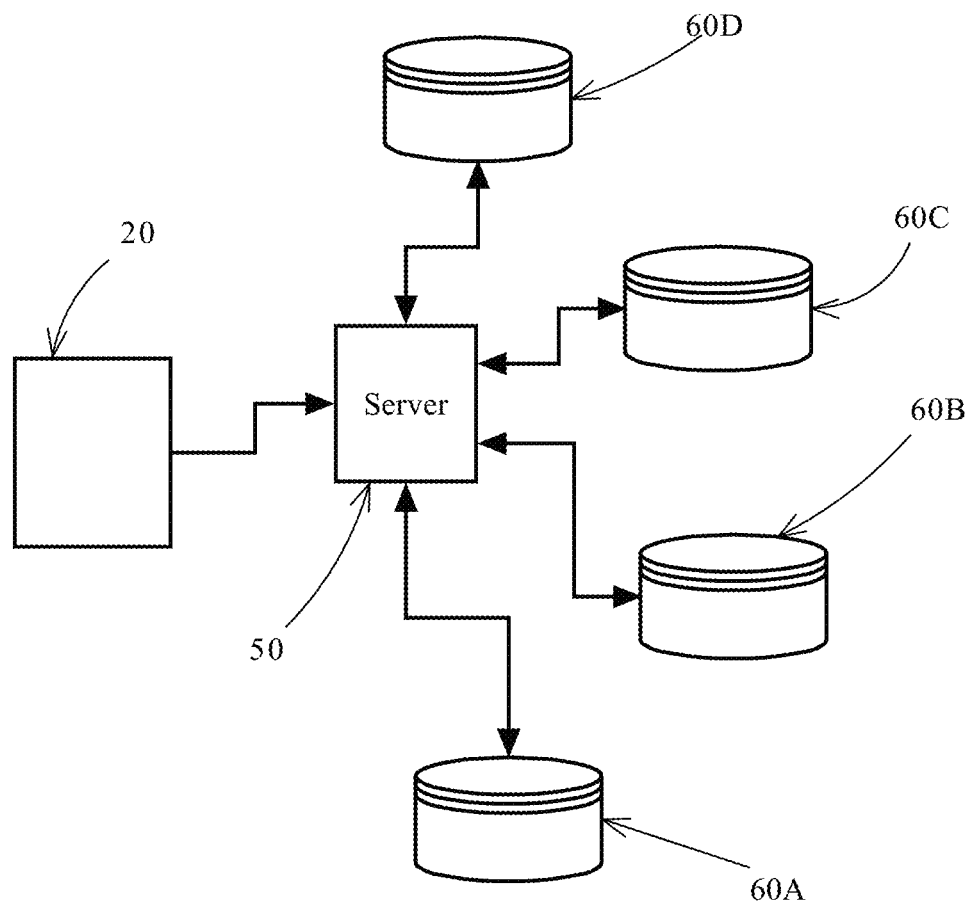
FIG. 9 is a block diagram illustrating the data connections between various components of the system according to another aspect of the invention.

As noted above, the system may include a server and a network of distributed databases connected to that server. The data gathered by the insole may be transmitted to either the server or to the databases. Such a server or its connected network of distributed databases may, to assist in the diagnosis of the user's condition for example, be used to consult with at least one medical or fitness database. Referring to FIG. 9, a block diagram illustrating the connections between the various parts of the system is illustrated. As can be seen from FIG. 9, the user's insole data gathering sub-system 20 communicates with a server 50. The server 50 serves as the main data processing and analytical unit to determine for example the user's physical or medical condition based, at least in part, on the data gathered from the user's gait. After the server receives gait data or the characteristic data from the insole 20 through communications module 50 (perhaps from two insoles), this data can be used by the server to determine the user's physical or medical condition. This includes determining the condition's progression, regression, or development. This may be performed by referring to one or more medical, fitness or kinematic reference model databases 60A, 60B, 60C, 60D. The server may receive both structured and unstructured data from the databases and/or from the user's insole. Preferably, the databases contain data relating to disease pathology, human performance, workforce industrial safety, human skeleton kinematics, sports performance, post-operative rehabilitation, therapeutics, pharmaceuticals prescribe and known side effects of such prescribed pharmaceuticals and/or gait-based biometric data relating to injury and disease pathologies including conditions such as diabetes, Parkinson's disease, dementia, aging, and other vestibular disorders.

To assist the server in determining a diagnosis and/or a determination of the progression, regression, or change in the user's condition, the following characteristics of the user may be entered into the server and may be taken into account in any analysis: a foot type, general health, fitness level, type of gait, height, weight, age, gender, and/or nationality. Data entry into the server may be performed using various well-known means. As an example, such data may be transferred from a user's profile on a connected mobile device to the server. The server may then take such user data, in conjunction with the gait-based and gait-derived data and analyze such data with data from the various databases. Then, based on the input from the various databases and the gathered data for the user, the server can produce its output.

The server's output may include an indication that the user's condition has regressed, progressed, is abnormal, or is normal. Similarly, the output may indicate the pathologies operative with the user as well as an indication if the user requires or is using corrective orthotics.

It should be noted that the user's foot characteristic may be one of: Egyptian, Roman, Greek, Germanic, or Celtic. Similarly, the user's foot type may be one of: flat arch, medium arch, or high arch. The user's type of gait may be one of: normal, toe in or toe out, knee in or knee out, lean forward or lean backward, posture easy or posture rigid, and trunk sway. The user's health and/or fitness may be categorized as one of: athletic, fit, average, below average, poor, or one where the user has a reported illness or disease.

Figure 10:
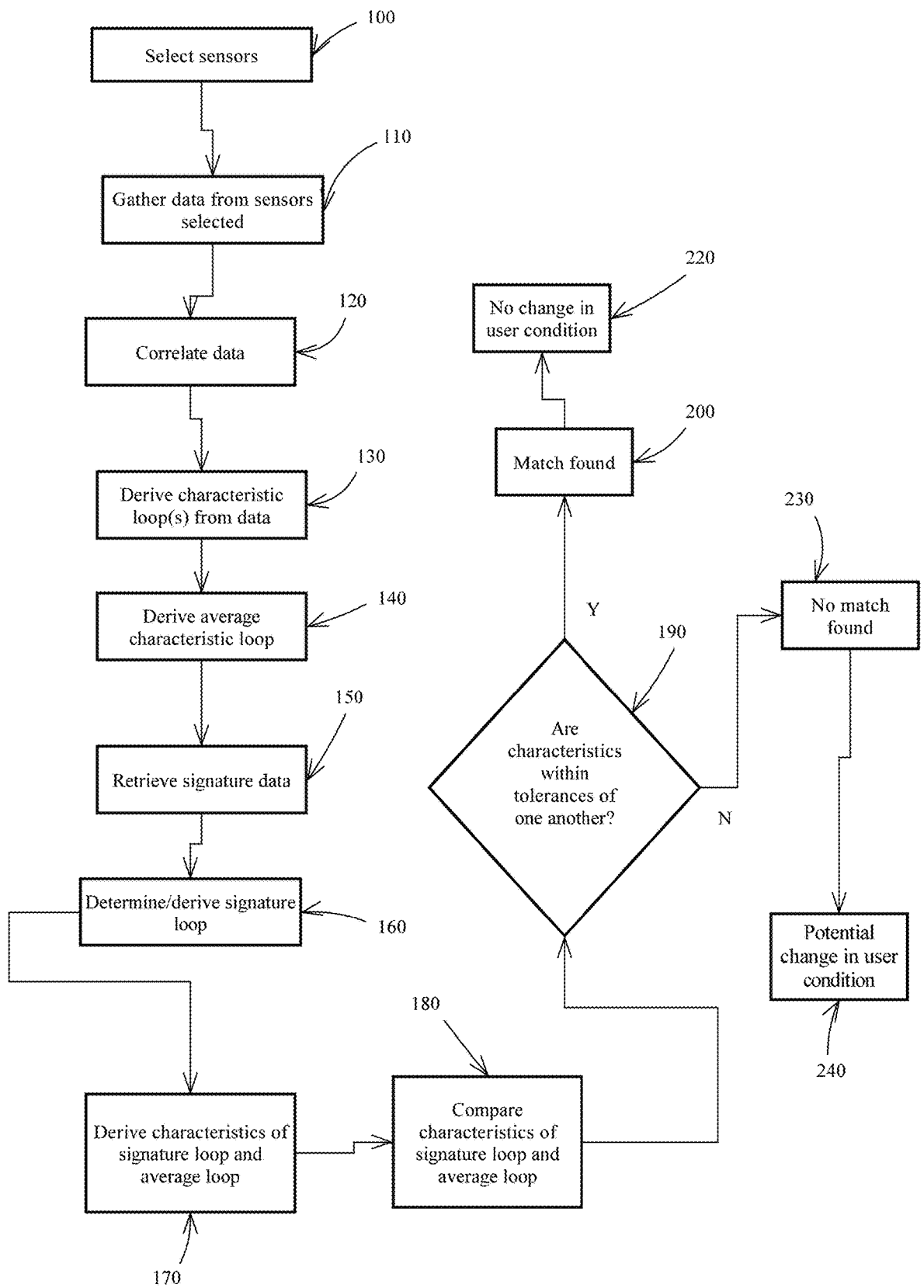
FIG. 10 is a flowchart illustrating the steps in a method according to another aspect of the invention.

Referring to FIG. 10, a flowchart of one aspect of the present invention is illustrated. The process illustrated in FIG. 10 details the steps in one variant of an aspect of the present invention. To store the signature data into the system, the initial step 100 in the process is that of selecting two of the sensors to be used in the comparison process. As noted above, the sensors are, in one embodiment, inserted or installed in a user's shoe. Once the sensors have been selected, data is gathered from these sensors as the user walks normally (step 110). Once gathered from the sensors, the data is then correlated with one another to form the data pairs noted above (step 120). This means that data points from one sensor is mated with data points from another sensor. With the data pairs in hand, at least one characteristic loop can then be created/derived from the data pairs (step 130). Depending on the configuration, discrete steps may be separated from one another so that each step may have its own characteristic loop. Alternatively, an average characteristic loop may be derived from the data values from the sensors. Once the average characteristic loop has been found (step 140), the signature data can be retrieved (step 150). The signature data, depending on configuration can then be used to determine the signature loop (step 160). The characteristics of both the average characteristic loop and the signature loop can then be calculated or derived from the two sets of data (step 170). The characteristics are then compared (step 180), taking into consideration the preprogrammed tolerances. If the characteristics from the two sets of data are the same (step 190) (within the preprogrammed tolerances) then a match is found (step 200) indicating no change in the user's condition (step 210). If they are not within the preprogrammed tolerances, then no match is found (step 220) and a potential change in the user's condition is indicated (step 230). The indication of whether a match is found or not found can then be communicated with the server 50. The server 50 may then communicate with the distributed databases to gather data and/or correlations between the user's characteristic data and potential/actual medical and/or physical conditions.

In another variant, the process according to one aspect of the invention may be seen as eight specific steps. These steps are described below.

The first processing step after retrieving the data is one where the pair sensor signals are filtered applying DFT (Discrete Fourier Transform) based low-pass filter. The cut-off frequency of the filter is defined taking into account a Nyquist frequency (related to the sampling rate) on the high end, and a main signal frequency (related to the walking speed of the individual) on the low end. Walking frequency estimation is also a part of the described processing step.

Using an FFT (Fast Fourier Transform) implementation technique and sync-filter as a benchmark, a low pass filter with flat pass-band (low ripple) high stop band attenuation may be used. Additional advantage is taken from the use of non-causal filters since the hard-real-time processing is not required (signals are registered first and then filters are applied).

The second processing step is a construction of the characteristic loop for the chosen pair of signals. The characteristic loop is an ordered set of points with coordinates (X(i),Y(i)) where X(i) is a first chosen signal and Y(i) is a second chosen signal, i is an index corresponding to the sample number.

An autonomous loop is constructed for the time period (subset of all samples) corresponding to the evolution of both signals from low level to maturity level and back to low level. Such a construction is possible since the low level of all signals have a non-empty intersection corresponding to the foot not contacting the ground.

Due to quasi-periodicity of all signals resulting from the nature of human walking, characteristic loops can be constructed autonomously for several periods in time.

Although initially defined for raw signals, autonomous loops can then be constructed for smoothed signals (obtained after the first step processing described above).

The third processing step is that of averaging the loops. Several loops are constructed according to the recording of several steps while the person is walking. Those steps and respectively those loops are subject to significant variations. It has been found that only the average loop provides a stable and robust characteristic of human walking.

Averaging of the loops is done by artificially synchronizing several loops (as corresponding to several steps) followed by weighted averaging of the synchronized loops. Weight factors are computed according to the phase shifts from an estimated reference signal (main walking frequency—as per first processing step).

The fourth processing step consists of extracting initial geometrical parameters from the average loop such as loop length, loop width, direction of longitudinal axes, loop directionality (clockwise or counterclockwise) and the area inside the loop. Other characteristics/parameters which can be used are the variance of each parameter listed above as computed for individual walking steps and as compared to the average value (computed from average loop).

Other parameters which can be extracted may use:
Geometrical method—identify a point on the loop farthest from the origin (e.g. referred to as M in this example) this point is further used to find the length (IOMI) and direction of the longitudinal axis (OM), the width is defined as maximal projection onto the line perpendicular to OM
Statistical approach—considering the loop as the cloud of points, the elliptical fit (correlation analysis) can be applied followed by extraction of the parameters of the fitted ellipse (major and minor axis length and orientation).

Regarding loop directionality, the directionality of the loop is related to the phase shift between signal Y and signal X. Namely, the loop is clockwise if Y signal grows from low level to maturity first, followed by the growth of X signal.

The fifth processing step consists of analysing special cases. It is worth noticing that in some cases, for some pairs of signals, the construction of the loop as described above might yield less than perfect results. This may result in a "degenerated loop" due to a high correlation between signals. The "loop" in such case is located very close to the diagonal. For this case only the point farthest from the origin is actually computed (corresponding to maximal amplitude of both signals).

The sixth processing step consists of comparing the loops computed from two separately recorded data sets. It has been found that the parametric representation of the pair-wise average loops have a high discrimination efficiency (see FIG. 8 as an example). Namely, for several pairs of signals/sensors extracted from the set of 8 signals/sensors, the average loops constructed from the smoothed signals stably demonstrate significant similarities when constructed from the data corresponding to the same individual as well as significant differences from average loops constructed for different individuals.

The seventh processing step consists of combining the results of the comparison of several (up to all 56 possible pairs from 8 different sensors/signals) pairs in order to produce a highly efficient discriminate function. Results from various pairs are first weighted according to the number of parameters that can be robustly estimated to support the comparison of the loops. Finally, the results from various pairs can be fused using a Dempster-Shaefer framework for an estimation of the likelihood that loops from the baseline data and the gathered data are similar or not.

In addition to the above processing steps, it should be noted that, for mobility-impaired-based applications, the data gathered can be expected to have a number of behaviours. The characteristics that are extracted when performing the loop signature computation (see above) can be divided in three classes:

A) (Class-1) Dimensionless parameters such as:
   (1) loop directionality,
   (2) direction of longitudinal axes of the loop,
   (3) loop elongation (e.g. major to minor axis ratio), etc., as well as standard deviations of those parameters computed over all of the collected data.

B) (Class-2) Size-type parameters having a single dimension such as:
   (1) loop length,
   (2) loop width,
   (3,4) major and minor axis of elliptical approximation of the loop (see above), etc. as well as standard deviations of those parameters computed over all of the collected data.

C) (Class-3) Area-type parameters having two dimensions such as:
   (1) area of the loop,
   (2) product of major and minor axis of elliptical approximation of the loop and variance of those parameters computed over all of the collected steps.

These 3 classes of the parameters can be used in different ways in determining the estimation of differences between data sets. For processing the data sets based on mobility impairments, factors such as stride length, stride to stride variability, cadence, and other movement data can affect class 1 and 2 data sets while factors such as weight, posture and other similar physiological changes can affect class 3 parameters.

As an example of how physical changes can affect the characteristics of the derived loops, one can look at the effects of weight-based differences. For such differences, dimensionless parameters (Class-1) are expected to be invariant to weight changes. Size-type parameters (Class-2) are expected to be proportional to the weight change, reflecting the fact that the loop is stretched or contracted according to the weight change factor (i.e. the ratio of newly estimated weight to the older one). Area-type parameters (Class-3) are expected to be proportional to the square of the weight change factor.

For processing of weight change-based data, the processing steps can be summarized as:
  1. Extraction of the data pairs that provide the robust estimation of relevant parameters;
  2. Estimation of the weight change factor from the class-2 (direct) and class-3 (as square root) parameters and verification of invariance of class-1 parameters;
  3. Determination of the hypothetical (average) value of the weight or physical characteristic factor;
  4. Analysis of the result based on Dempster-Shaefer framework in order to estimate the likelihood that the gathered data supports the determined value.

Of course, the above steps can also be used to process data to determine changes in gait-based data due to other physiological changes. In step 2, instead of estimating the weight change factor, the change factor due to the physiological change can be performed and verification that some other parameters are invariant can be performed.

It should also be noted that a data histogram of daily loop signatures can be stored in the storage module and can be periodically re-correlated to form a new biometric loop signature which reflects the user's weight gain or loss or the progression of regression of a disease, sickness, or injury.

Figure 11:
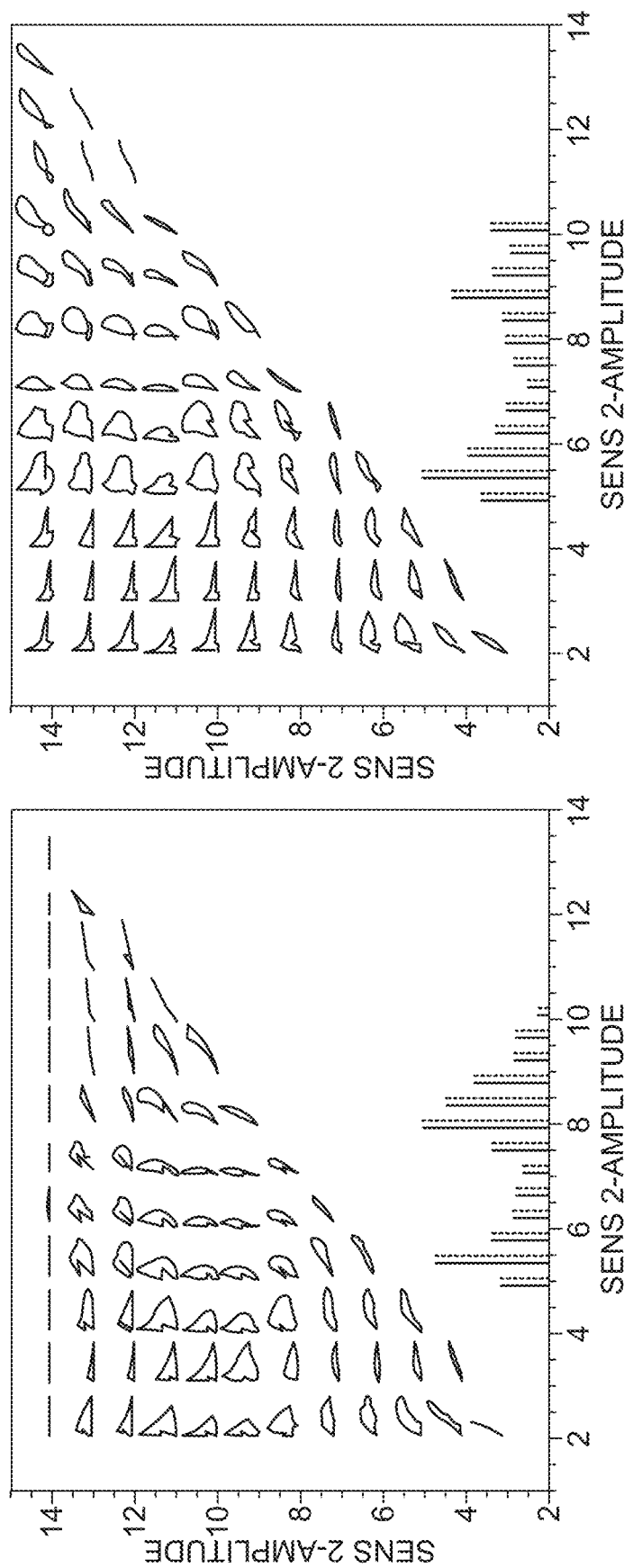
FIG. 11 is an illustration of an individual user's baseline loop signature for a left foot and a right foot.

To assist in the understanding of the present invention, FIG. 11 is provided. In FIG. 11 is illustrated the baseline or signature loops for a left foot (left image) and for a right foot (right image) for a user.

The system described above may be used in any number of ways. The system can be used to determine a user's physical or medical condition as well as whether a fitness program or treatment regimen is effective or not. As is well known, for some physical and medical conditions, the progression of the condition affects a person's gait. Similarly, the regression of the condition also affects the person's gait. As such, by comparing a user's baseline gait data with subsequently gathered gait data, the user's condition can be monitored. If no change in the user's gait is detected, then the physical or medical condition has neither progressed nor regressed. If there is a noticeable change in the user's gait (as evidenced by differences in the loops derived from the baseline gait data and the subsequent gait data) this may indicate progression, regression, efficacy of a fitness program or treatment regimen, or any number of health changes in the user. This determination can additionally be performed by the server, perhaps in conjunction with input from the various databases noted above. As well, the determination may be performed after human verification and checking of the data provided. This determination may be made in conjunction with other clinical tests so as to determine correlation between the loop differences, the types of differences, the amount of the difference, and the different conditions and changes in the condition.

In another embodiment, all of the data processed by the data processing module may be internally encrypted so that external systems would not be privy to the raw data transferred between the sensor module and the data processing module. Prior to transmitting the raw data from the sensor module to the data processing module, the data may be automatically encrypted. As can be understood, the data processing module may be physically remote from the sensor module and, as such, the data transmissions between these modules may be vulnerable to the outside. In another embodiment, the data processing module is contained within the insole to ensure that any data transfers between the modules are slightly more secure.

In another embodiment, any data transfers or communications between the system and any outside server or network systems are encrypted, preferably with one-time encryption schemes, to ensure that outsiders are not able to intercept any usable data. Such precautions would preserve the system user's privacy.

The system of the invention may be used to periodically determine if a user's physical or medical condition is progressing or regressing. As well, it may be used to determine if any fitness program or treatment regimen to which the user is being subjected to has had an effect on the user or on the user's gait. The user's baseline gait data may be gathered when the user first visits a facility properly equipped with the system of the invention. Subsequent visits by the user would entail gathering subsequent gait data sets. The loops derived from the baseline gait data set and the subsequent gait data sets can be compared with one another to view any variances between the user's gait data. The amount of change in the loop characteristics from the different data sets can provide an indication as to the degree of change in the user's condition. Large changes in the loop characteristics may indicate an acceleration in the user's condition and may also indicate whether the user's fitness program or treatment regimen (which may include pharmacological treatments) is effective or not.

It should be clear that the present invention may be used in multiple ways and may be used in different variants. In one variant, the data from the sensors are transmitted to an external device such as a smartphone, smart watch, or home-based computer system for further analysis. A further variant uses the force applied to different areas of the sensor module. The forces are used in the skeletal and joint models and are correlated with a range of disease related gait patterns using models and data stored in the distributed databases.

To assist in mapping the existing and possible biomarkers in the gait-based data stored in the distributed databases, the system may use machine learning and artificial intelligence algorithms to continuously search for existing and potential biomarkers that relate to disease pathologies, sicknesses, and injuries, as well as effects of prescribed pharmacologies.

It should also be clear that the system may use distributed databases that may be populated using patient data from medicine dispensing organizations (e.g. pharmacies), medical facilities (e.g., hospitals), and/or regulators. Regulators such as the USFDA may provide data as that data relates to published side effects of prescribed pharmaceuticals on the market and available to public consumers. The populated databases can then be mined for conclusions, trends, and insights into the health and wellness of the population using machine learning and artificial intelligence algorithms. These mined conclusions, trends and insights can then be applied to individual and population-based risk reduction models relating to health, medicine, product liability, online behaviors, as well as for insurance purposes. For such insurance uses, the data and the conclusions from the data can provide structured and verifiable data for personalized actuarial sciences and continuous underwriting of risk. As a further use for the system, portions of the system can form the basis of a gait-based identification system. This identification system can then be used to remove or reduce source data fraud. The identification system may be based on using a baseline gait based dataset for a user that is stored in a user device or on a server. When the user approaches a gateway or device where an identity needs to be verified (e.g. an ATM, a secure doorway/location, etc.), the baseline gait based dataset on the user device or server can be checked against the real-time or near real-time data produced by the gait based data gathering apparatus. If the data gathered is not within acceptable parameters, then the person approaching the gateway or device is not authenticated.

It should be clear that one or more of the databases of the present invention may be populated with pharmaceutical data from published records of one or more federal, state, provincial, or foreign regulator. This would enable the data processing module of the system to correlate biomarkers with known side effects of medications. These medications may, of course, be for existing conditions of users.

In addition to the above, one or more of the databases may be populated with kinematic data from representative mathematical models. This allows the data processing module to correlate the biomarkers with skeletal or joint abnormalities for the users' existing conditions.

Yet a further use for the present system is that of determining individualized and population insights derived from the distributed databases. These insights may be developed using machine learning and artificial intelligence algorithms and may be derived using patient data in the distributed databases, with the patient data being sourced from medical and pharmaceutical organizations.

It should also be clear that the skeletal and joint models used in the present invention may be used, in conjunction with machine learning and artificial intelligence algorithms, with assistive devices (such as exoskeletons) and with bipedal robotic systems to thereby provide for natural human movement, balance, and adaptive mobility.

The system and methods of the present invention may also be used determining athletic performance or in the gathering of athletic performance metrics. The data gathered while an athlete is training may be compared against a baseline dataset gathered prior to the commencement of training. Such comparisons between the baseline dataset or between different datasets taken during training can provide metrics of how an athlete's performance is progressing or regressing. Of course, other datasets (whether gathered in real-time or near real-time in training or during competitions) can also provide indications as to an athlete's performance. It should also be clear that the comparisons and the analysis may be performed in real-time or in near real-time depending on the configuration of the data processing system configured to receive and/or process the datasets. Depending on the configuration, real-time performance metrics or near real-time performance metrics may be obtained.

A further aspect of the present invention involves the format standardization of loop data characteristics such that the data may be used with the full range of foot size, shape and characteristic including age, gender and nationality for continued analysis and for individual and population generated insights.

It should be clear that the various aspects of the present invention may be implemented as software modules in an overall software system. As such, the present invention may thus take the form of computer executable instructions that, when executed, implements various software modules with predefined functions.

The embodiments of the invention may be executed by a computer processor or similar device programmed in the manner of method steps or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g., "C" or "Go") or an object-oriented language (e.g., "C++", "java", "PHP", "PYTHON" or "C #"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A system for determining at least one change in a user's condition, said system comprising:
    at least one sensor module comprising at least one sensor for gathering gait-based biometric data from said user, said at least one sensor module being in a single device comprising at least two sensors and said at least two sensors comprising force sensors, said device being an insole for placement within a shoe of said user;
    processing circuitry and at least one memory unit, said at least one memory unit having stored thereon computer-executable instructions that, when executed, implement:
        a data storage module for storing data relating to baseline data, said baseline data being derived from said gait-based biometric data gathered from said at least one sensor module when said user first uses said system; and
        a data processing module for receiving data from said at least one sensor module, said data processing module being for comparing characteristics of said baseline data with characteristics of said data received from said at least one sensor module; and
    at least one database in communication with said data processing module, said at least one database containing data relating to a base kinematic chain model specific to said user, said base kinematic chain model being derived from said baseline data,
    wherein:
        said data processing module derives a current kinematic chain model from said data received from said at least one sensor module;
        said data processing module compares characteristics of said current kinematic chain model with characteristics of said base kinematic chain model;
        a change in said user's condition is indicated when said characteristics of said data received from said at least one sensor module are not within predetermined limits of said characteristics of said baseline data;
        said insole is positioned at a single end of a kinematic chain of said user, such that said baseline data for said base kinematic chain model and said data for said current kinematic chain model are received only from said single end of said kinematic chain by way of said insole;
        said at least one database stores said gait-based biometric data from a plurality of users; and
        said data processing module continuously searches said gait-based biometric data to determine biomarkers for existing conditions of said users.

2. The system according to claim 1, wherein said at least one sensor is configured to detect and measure a force applied to said at least one sensor module by a foot of said user as said user is standing or walking.

3. The system according to claim 1, wherein said at least one sensor is configured to detect and measure pressure applied by said user's foot to said at least one sensor as said user is walking.

4. The system according to claim 1, wherein said at least one sensor is configured to detect a force applied to different areas of said at least one sensor module by said user's foot as said user is walking.

5. The system according to claim 1, wherein said at least one sensor comprises a plurality of sensors, each sensor being for detecting and measuring an amount of force applied to different areas of said sensor module by said user's foot.

6. The system according to claim 5, wherein said plurality of sensors transmits said gait-based biometric data to an external device.

7. The system according to claim 4, where data relating to said force applied to different areas of said at least one sensor module is compared by said data processing module to a plurality of models stored in said at least one database, each of said plurality of models being correlated to at least one of a range of disease related gait patterns.

8. The system according to claim 1, wherein said data processing module employs machine learning techniques to mine said at least one database of gait-based biometric data for next biomarkers related to existing conditions of said users.

9. The system according to claim 1, wherein said at least one database stores said gait-based biometric data from a plurality of users and said data processing module derives generalized population-based conclusions from said gait-based biometric data.

10. The system according to claim 1, wherein at least a portion of said system is used for a gait-based identification system.

11. The system according to claim 9, wherein said generalized population-based conclusions are used for insurance purposes.

12. The system according to claim 1, wherein said at least one database is further populated with patient data from at least one medical facility to thereby enable said data processing module to correlate said biomarkers with said existing conditions of said users.

13. The system according to claim 1, wherein said at least one database is populated with patient data from records of at least one medication dispensing facility to thereby enable said data processing module to correlate said biomarkers with medications for said existing conditions of said users.

14. The system according to claim 1, wherein said at least one database is populated with pharmaceutical data from published records of at least one regulator to thereby enable said data processing module to correlate said biomarkers with known side effects of medications for said existing conditions of said users.

15. The system according to claim 1, wherein said at least one database is populated with kinematic data from representative mathematical models to thereby enable said data processing module to correlate said biomarkers with skeletal or joint abnormalities for said existing conditions of said users.

* * * * *